US011638653B2

(12) United States Patent
Nayet et al.

(10) Patent No.: US 11,638,653 B2
(45) Date of Patent: May 2, 2023

(54) SURGERY INSTRUMENTS WITH A MOVABLE HANDLE

(71) Applicant: Warsaw Orthopedic, Inc., Warsaw, IN (US)

(72) Inventors: Jerome Nayet, Saint-Genis-Pouilly (FR); Loic Josse, Collierville, TN (US); Richard A. Hynes, Melbourne Beach, FL (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 0 days.

(21) Appl. No.: 17/185,062

(22) Filed: Feb. 25, 2021

(65) Prior Publication Data

US 2022/0133503 A1    May 5, 2022

Related U.S. Application Data

(63) Continuation-in-part of application No. 17/181,556, filed on Feb. 22, 2021, which is a continuation-in-part
(Continued)

(30) Foreign Application Priority Data

| Nov. 5, 2020 | (WO) | PCT/IB2020/000932 |
| Nov. 5, 2020 | (WO) | PCT/IB2020/000942 |
| Nov. 5, 2020 | (WO) | PCT/IB2020/000953 |

(51) Int. Cl.
*A61F 2/46* (2006.01)
*A61B 17/16* (2006.01)

(52) U.S. Cl.
CPC ........ *A61F 2/4603* (2013.01); *A61B 17/1624* (2013.01); *A61B 17/1671* (2013.01); *A61F 2/4611* (2013.01); *A61F 2002/4627* (2013.01)

(58) Field of Classification Search
CPC ..... A61F 2/4609; A61B 17/1666; A61B 1/32; A61B 1/303; A61B 17/1728; A61B 17/58;
(Continued)

(56) References Cited

U.S. PATENT DOCUMENTS 1,677,337 A * 7/1928 Grove ................ A61B 17/1688
                                                                606/180
3,847,154 A * 11/1974 Nordin ............... A61B 17/1622
                                                                606/180
(Continued)

FOREIGN PATENT DOCUMENTS

CN    107 137 166 A    9/2017
DE    44 16605 C1      6/1995
(Continued)

OTHER PUBLICATIONS

International Search Report, and Written Opinion for Application. No. PCT/US2019/019067, dated Jun. 3, 2019.
(Continued)

*Primary Examiner* — Matthew J Lawson
(74) *Attorney, Agent, or Firm* — Fox Rothschild LLP; P. Marshall Ticer

(57) ABSTRACT

Various surgical tools having a movable handle mechanism including a positioning handle are disclosed. The movable handle mechanism may be configured to move forward and backward in a longitudinal direction along the housing and rotate clockwise and counterclockwise around the housing. In various embodiments, the housing may include a plurality of channels and each channel may have at least one detent. The movable handle mechanism may be configured to securely couple to the housing via one channel of the plurality of channels and one detent of the plurality of detents. At least one surgical tool may include a drill having an angled tip portion and a sleeve configured to protect
(Continued)

adjacent structures from lateral edges of the drill bit when the drill bit is rotating. Another surgical tool may include a screwdriver having an elastic retaining clip configured to progressively release a bone screw therein at an extraction force.

10 Claims, 36 Drawing Sheets

Related U.S. Application Data of application No. 17/123,906, filed on Dec. 16, 2020, now Pat. No. 11,517,363.

(58) Field of Classification Search
CPC .......... A61B 17/17808; A61B 17/1624; A61B 17/1631; A61B 17/1633; A61B 17/1637; A61B 17/1642; A61B 17/1671
See application file for complete search history.

(56) References Cited

U.S. PATENT DOCUMENTS

| | | | |
|---|---|---|---|
| 4,401,112 A | 8/1983 | Rezaian | |
| 4,553,273 A | 11/1985 | Wu | |
| 4,636,217 A | 1/1987 | Ogilvie et al. | |
| 4,716,894 A * | 1/1988 | Lazzeri | A61F 2/4609 606/91 |
| 4,759,769 A | 7/1988 | Hedman et al. | |
| 5,059,193 A | 10/1991 | Kuslich | |
| 5,171,278 A | 12/1992 | Pisharodi | |
| 5,228,811 A * | 7/1993 | Potter | B23B 47/284 408/112 |
| 5,284,483 A * | 2/1994 | Johnson | A61F 2/4609 606/86 R |
| 5,336,223 A | 8/1994 | Rogers | |
| 5,390,683 A | 2/1995 | Pisharodi | |
| 5,522,899 A | 6/1996 | Michelson | |
| 5,554,191 A | 9/1996 | Lahille et al. | |
| 5,575,790 A | 11/1996 | Chen et al. | |
| 5,609,635 A | 3/1997 | Michelson | |
| 5,653,762 A | 8/1997 | Pisharodi | |
| 5,653,763 A | 8/1997 | Errico et al. | |
| 5,658,336 A | 8/1997 | Pisharodi | |
| 5,665,122 A | 9/1997 | Kambin | |
| 5,693,100 A | 12/1997 | Pisharodi | |
| 5,697,977 A | 12/1997 | Pisharodi | |
| 5,702,391 A | 12/1997 | Lin | |
| 5,702,453 A | 12/1997 | Rabbe et al. | |
| 5,702,455 A | 12/1997 | Saggar | |
| 5,797,918 A | 8/1998 | McGuire et al. | |
| 5,800,550 A | 9/1998 | Sertich | |
| 5,865,848 A | 2/1999 | Baker | |
| 5,893,890 A | 4/1999 | Pisharodi | |
| 5,931,777 A | 8/1999 | Sava | |
| 5,941,885 A | 8/1999 | Jackson | |
| 5,971,987 A | 10/1999 | Huxel et al. | |
| 5,980,522 A | 11/1999 | Koros et al. | |
| 6,045,579 A | 4/2000 | Hochshuler et al. | |
| 6,074,343 A | 6/2000 | Nathanson et al. | |
| 6,080,193 A | 6/2000 | Hochshuler et al. | |
| 6,099,531 A | 8/2000 | Bonutti | |
| 6,102,949 A | 8/2000 | Biedermann et al. | |
| 6,102,950 A | 8/2000 | Vaccaro | |
| 6,106,557 A | 8/2000 | Robioneck et al. | |
| 6,113,638 A | 9/2000 | Williams et al. | |
| 6,117,174 A | 9/2000 | Nolan | |
| 6,132,465 A | 10/2000 | Ray et al. | |
| 6,159,211 A | 12/2000 | Boriani et al. | |
| 6,159,244 A | 12/2000 | Suddaby | |
| 6,176,882 B1 | 1/2001 | Biedermann et al. | |
| 6,179,873 B1 | 1/2001 | Zientek | |
| 6,190,414 B1 | 2/2001 | Young et al. | |
| 6,193,757 B1 | 2/2001 | Foley et al. | |
| 6,217,579 B1 | 4/2001 | Koros | |
| 6,245,108 B1 | 6/2001 | Biscup | |
| 6,309,421 B1 | 10/2001 | Pisharodi | |
| 6,342,074 B1 | 1/2002 | Simpson | |
| 6,371,989 B1 | 4/2002 | Chauvin et al. | |
| 6,395,031 B1 | 5/2002 | Foley et al. | |
| 6,423,063 B1 | 7/2002 | Bonutti | |
| 6,432,106 B1 | 8/2002 | Fraser | |
| 6,436,140 B1 | 8/2002 | Liu et al. | |
| 6,443,989 B1 | 9/2002 | Jackson | |
| 6,443,990 B1 | 9/2002 | Aebi et al. | |
| 6,454,806 B1 | 9/2002 | Cohen et al. | |
| 6,454,807 B1 | 9/2002 | Jackson | |
| 6,461,359 B1 | 10/2002 | Tribus et al. | |
| 6,491,724 B1 | 12/2002 | Ferree | |
| 6,520,991 B2 | 2/2003 | Huene | |
| 6,520,993 B2 | 2/2003 | James et al. | |
| 6,524,238 B2 * | 2/2003 | Velikaris | A61B 17/02 16/422 |
| 6,527,803 B1 | 3/2003 | Crozet et al. | |
| 6,562,074 B2 | 5/2003 | Gerbec et al. | |
| 6,576,016 B1 | 6/2003 | Hochshuler et al. | |
| 6,623,525 B2 | 9/2003 | Ralph et al. | |
| 6,629,998 B1 | 10/2003 | Lin | |
| 6,635,086 B2 | 10/2003 | Lin | |
| 6,648,917 B2 | 11/2003 | Gerbec et al. | |
| 6,676,703 B2 | 1/2004 | Biscup | |
| 6,685,742 B1 | 2/2004 | Jackson | |
| 6,723,126 B1 | 4/2004 | Berry | |
| 6,770,096 B2 | 8/2004 | Bolger et al. | |
| 6,773,460 B2 | 8/2004 | Jackson | |
| 6,821,298 B1 | 11/2004 | Jackson | |
| 6,835,206 B2 | 12/2004 | Jackson | |
| 6,849,093 B2 | 2/2005 | Michelson | |
| 6,852,129 B2 | 2/2005 | Gerbec et al. | |
| 6,863,673 B2 | 3/2005 | Gerbec et al. | |
| 6,923,814 B1 | 8/2005 | Hildebrand et al. | |
| 6,926,737 B2 | 8/2005 | Jackson | |
| 6,953,477 B2 | 10/2005 | Berry | |
| 6,964,687 B1 | 11/2005 | Bernard et al. | |
| 6,974,480 B2 | 12/2005 | Messerli et al. | |
| 6,984,234 B2 | 1/2006 | Bray | |
| 7,112,222 B2 | 9/2006 | Fraser et al. | |
| 7,135,043 B2 | 11/2006 | Nakahara et al. | |
| 7,137,997 B2 | 11/2006 | Paul | |
| 7,172,627 B2 | 2/2007 | Fiere et al. | |
| 7,188,626 B2 | 3/2007 | Foley et al. | |
| 7,204,853 B2 | 4/2007 | Gordon et al. | |
| 7,232,464 B2 | 6/2007 | Mathieu et al. | |
| 7,238,203 B2 | 7/2007 | Bagga et al. | |
| 7,255,700 B2 | 8/2007 | Kaiser et al. | |
| 7,316,532 B2 | 1/2008 | Matthys-Mark | |
| 7,316,714 B2 | 1/2008 | Gordon et al. | |
| 7,407,483 B2 | 8/2008 | Perez-Cruet et al. | |
| 7,481,766 B2 | 1/2009 | Lee et al. | |
| 7,491,168 B2 | 2/2009 | Raymond et al. | |
| 7,537,565 B2 | 5/2009 | Bass | |
| 7,618,456 B2 | 11/2009 | Mathieu et al. | |
| 7,625,394 B2 | 12/2009 | Molz, IV et al. | |
| 7,635,366 B2 | 12/2009 | Abdou | |
| 7,637,909 B2 * | 12/2009 | Lechot | A61B 17/1666 606/81 |
| 7,655,046 B2 | 2/2010 | Dryer et al. | |
| 7,678,148 B2 | 3/2010 | Peterman | |
| 7,703,727 B2 | 4/2010 | Selness | |
| 7,708,778 B2 | 5/2010 | Gordon et al. | |
| 7,708,779 B2 | 5/2010 | Edie et al. | |
| 7,727,280 B2 | 6/2010 | McLuen | |
| 7,753,958 B2 | 7/2010 | Gordon et al. | |
| 7,780,594 B2 | 8/2010 | Hutton | |
| 7,806,932 B2 | 10/2010 | Webb et al. | |
| 7,815,682 B1 | 10/2010 | Peterson et al. | |
| 7,819,801 B2 | 10/2010 | Miles et al. | |
| 7,824,428 B2 | 11/2010 | Mikkonen et al. | |
| 7,828,849 B2 | 11/2010 | Lim | |
| 7,846,167 B2 | 12/2010 | Garcia et al. | |
| 7,846,207 B2 | 12/2010 | Lechmann et al. | |
| 7,850,731 B2 | 12/2010 | Brittan et al. | |
| 7,850,733 B2 | 12/2010 | Baynham et al. | |

(56) References Cited

U.S. PATENT DOCUMENTS

| | | | |
|---|---|---|---|
| 7,862,616 B2 | 1/2011 | Lechmann et al. |
| 7,875,076 B2 | 1/2011 | Mathieu et al. |
| 7,892,173 B2 | 2/2011 | Miles et al. |
| 7,909,869 B2 | 3/2011 | Gordon et al. |
| 7,914,559 B2 | 3/2011 | Carls et al. |
| 7,967,821 B2 | 6/2011 | Sicvol et al. |
| 7,981,031 B2 | 7/2011 | Frasier et al. |
| 8,016,836 B2 | 9/2011 | Corrao et al. |
| 8,062,375 B2 | 11/2011 | Glerum et al. |
| 8,105,382 B2 | 1/2012 | Olmos et al. |
| 8,118,870 B2 | 2/2012 | Gordon et al. |
| 8,118,871 B2 | 2/2012 | Gordon et al. |
| 8,123,810 B2 | 2/2012 | Gordon et al. |
| 8,147,550 B2 | 4/2012 | Gordon et al. |
| 8,172,903 B2 | 5/2012 | Gordon et al. |
| 8,182,539 B2 | 5/2012 | Tyber et al. |
| 8,257,442 B2 | 9/2012 | Edie et al. |
| 8,262,570 B2 | 9/2012 | White et al. |
| 8,262,662 B2 | 9/2012 | Beardsley et al. |
| 8,262,710 B2 | 9/2012 | Freedman et al. |
| 8,287,597 B1 | 10/2012 | Pimenta et al. |
| 8,303,498 B2 | 11/2012 | Miles et al. |
| 8,303,658 B2 | 11/2012 | Peterman |
| 8,303,663 B2 | 11/2012 | Jimenez et al. |
| 8,317,866 B2 | 11/2012 | Palmatier et al. |
| 8,323,185 B2 | 12/2012 | Perez-Cruet et al. |
| 8,328,872 B2 | 12/2012 | Duffield et al. |
| 8,343,048 B2 | 1/2013 | Warren, Jr. |
| 8,353,826 B2 | 1/2013 | Weiman |
| 8,355,780 B2 | 1/2013 | Miles et al. |
| 8,382,842 B2 | 2/2013 | Greenhalgh et al. |
| 8,388,527 B2 | 3/2013 | Miles et al. |
| 8,398,713 B2 | 3/2013 | Weiman |
| 8,403,990 B2 | 3/2013 | Dryer et al. |
| 8,419,797 B2 | 4/2013 | Biedermann et al. |
| 8,425,528 B2 | 4/2013 | Berry et al. |
| 8,435,298 B2 | 5/2013 | Weiman |
| 8,480,576 B2 | 7/2013 | Sandhu |
| 8,496,706 B2 | 7/2013 | Ragab et al. |
| 8,500,634 B2 | 8/2013 | Miles et al. |
| 8,506,635 B2 | 8/2013 | Palmatier et al. |
| 8,517,935 B2 | 8/2013 | Marchek et al. |
| 8,518,120 B2 | 8/2013 | Glerum et al. |
| 8,535,380 B2 | 9/2013 | Greenhalgh et al. |
| 8,550,994 B2 | 10/2013 | Miles et al. |
| 8,556,808 B2 | 10/2013 | Miles et al. |
| 8,556,979 B2 | 10/2013 | Glerum et al. |
| 8,579,809 B2 | 11/2013 | Parker |
| 8,579,898 B2 | 11/2013 | Prandi et al. |
| 8,579,979 B2 | 11/2013 | Edie et al. |
| 8,579,981 B2 | 11/2013 | Lim et al. |
| 8,602,984 B2 | 12/2013 | Raymond et al. |
| 8,608,785 B2 | 12/2013 | Reed et al. |
| 8,628,576 B2 | 1/2014 | Triplett et al. |
| 8,628,578 B2 | 1/2014 | Miller et al. |
| 8,632,595 B2 | 1/2014 | Weiman |
| 8,641,768 B2 | 2/2014 | Duffield et al. |
| 8,647,386 B2 | 2/2014 | Gordon et al. |
| 8,663,329 B2 | 3/2014 | Ernst |
| 8,668,419 B2 | 3/2014 | Hardt et al. |
| 8,668,715 B2 | 3/2014 | Sandhu |
| 8,679,183 B2 | 3/2014 | Glerum et al. |
| 8,685,095 B2 | 4/2014 | Miller et al. |
| 8,685,098 B2 | 4/2014 | Glerum et al. |
| 8,696,559 B2 | 4/2014 | Miles et al. |
| 8,709,083 B2 | 4/2014 | Duffield et al. |
| 8,709,085 B2 | 4/2014 | Lechmann et al. |
| 8,709,086 B2 | 4/2014 | Glerum |
| 8,715,285 B2 | 5/2014 | Lewis et al. |
| 8,715,353 B2 | 5/2014 | Bagga et al. |
| 8,740,983 B1 * | 6/2014 | Arnold .................. A61F 2/4611 |
| | | | 623/17.16 |
| 8,753,271 B1 | 6/2014 | Miles et al. |
| 8,753,396 B1 | 6/2014 | Hockett et al. |
| 8,764,649 B2 | 7/2014 | Miles et al. |
| 8,771,360 B2 | 7/2014 | Jimenez et al. |
| 8,778,025 B2 | 7/2014 | Ragab et al. |
| 8,778,027 B2 | 7/2014 | Medina |
| 8,795,366 B2 | 8/2014 | Varela |
| 8,808,305 B2 | 8/2014 | Kleiner |
| 8,827,902 B2 | 9/2014 | Dietze, Jr. et al. |
| 8,828,085 B1 | 9/2014 | Jensen |
| 8,840,668 B1 * | 9/2014 | Donahoe ................ A61F 2/442 |
| | | | 623/17.16 |
| 8,845,731 B2 | 9/2014 | Weiman |
| 8,845,732 B2 | 9/2014 | Weiman |
| 8,845,734 B2 | 9/2014 | Weiman |
| 8,852,252 B2 | 10/2014 | Venturini et al. |
| 8,852,282 B2 | 10/2014 | Farley et al. |
| 8,864,833 B2 | 10/2014 | Glerum et al. |
| 8,882,813 B2 | 11/2014 | Jones et al. |
| 8,888,853 B2 | 11/2014 | Glerum et al. |
| 8,894,708 B2 | 11/2014 | Thalgott et al. |
| 8,894,711 B2 | 11/2014 | Varela |
| 8,894,712 B2 | 11/2014 | Varela |
| 8,906,095 B2 | 12/2014 | Christensen et al. |
| 8,920,500 B1 | 12/2014 | Pimenta et al. |
| 8,926,704 B2 | 1/2015 | Glerum et al. |
| 8,936,641 B2 | 1/2015 | Cain |
| 8,940,049 B1 | 1/2015 | Jimenez et al. |
| 8,968,363 B2 | 3/2015 | Weiman et al. |
| 8,986,344 B2 | 3/2015 | Sandhu |
| 8,992,425 B2 | 3/2015 | Karpowicz et al. |
| 8,992,544 B2 | 3/2015 | Sasing |
| 9,005,292 B2 | 4/2015 | Melamed |
| 9,005,293 B2 | 4/2015 | Moskowitz et al. |
| 9,005,295 B2 | 4/2015 | Kueenzi et al. |
| 9,017,412 B2 | 4/2015 | Wolters et al. |
| 9,034,045 B2 | 5/2015 | Davenport et al. |
| 9,050,146 B2 | 6/2015 | Woolley et al. |
| 9,050,194 B2 | 6/2015 | Thibodeau |
| 9,060,877 B2 | 6/2015 | Kleiner |
| 9,072,548 B2 | 7/2015 | Matityahu |
| 9,072,563 B2 | 7/2015 | Garcia et al. |
| 9,084,591 B2 | 7/2015 | Reglos et al. |
| 9,113,854 B2 | 8/2015 | Ellman |
| 9,119,730 B2 | 9/2015 | Glerum et al. |
| 9,125,757 B2 | 9/2015 | Weiman |
| 9,132,021 B2 | 9/2015 | Mermuys et al. |
| 9,138,217 B2 | 9/2015 | Smith et al. |
| 9,138,330 B2 | 9/2015 | Hansell et al. |
| 9,138,331 B2 | 9/2015 | Aferzon |
| 9,149,367 B2 | 10/2015 | Davenport et al. |
| 9,155,628 B2 | 10/2015 | Glerum et al. |
| 9,155,631 B2 | 10/2015 | Seifert et al. |
| 9,161,841 B2 | 10/2015 | Kana et al. |
| 9,179,903 B2 | 11/2015 | Cianfrani et al. |
| 9,179,952 B2 | 11/2015 | Biedermann et al. |
| 9,186,193 B2 | 11/2015 | Kleiner et al. |
| 9,186,258 B2 | 11/2015 | Davenport et al. |
| 9,192,482 B1 | 11/2015 | Pimenta et al. |
| 9,192,483 B1 | 11/2015 | Radcliffe et al. |
| 9,198,772 B2 | 12/2015 | Weiman |
| 9,204,972 B2 | 12/2015 | Weiman et al. |
| 9,204,974 B2 | 12/2015 | Glerum et al. |
| 9,211,194 B2 | 12/2015 | Bagga et al. |
| 9,211,196 B2 | 12/2015 | Glerum et al. |
| 9,216,095 B2 | 12/2015 | Glerum et al. |
| 9,226,836 B2 | 1/2016 | Glerum |
| 9,233,007 B2 | 1/2016 | Sungarian et al. |
| 9,233,009 B2 | 1/2016 | Gray et al. |
| 9,233,010 B2 | 1/2016 | Thalgott et al. |
| 9,259,327 B2 | 2/2016 | Niemiec et al. |
| 9,271,846 B2 | 3/2016 | Lim et al. |
| 9,308,099 B2 | 4/2016 | Triplett et al. |
| 9,320,610 B2 | 4/2016 | Alheidt et al. |
| 9,351,845 B1 | 5/2016 | Pimenta et al. |
| 9,351,848 B2 | 5/2016 | Glerum et al. |
| 9,357,909 B2 | 6/2016 | Perez-Cruet et al. |
| 9,358,126 B2 | 6/2016 | Glerum et al. |
| 9,358,127 B2 | 6/2016 | Duffield et al. |
| 9,358,128 B2 | 6/2016 | Glerum et al. |
| 9,358,129 B2 | 6/2016 | Weiman |
| 9,364,343 B2 | 6/2016 | Duffield et al. |

(56) References Cited

U.S. PATENT DOCUMENTS

| | | |
|---|---|---|
| 9,370,434 B2 | 6/2016 | Weiman |
| 9,370,435 B2 | 6/2016 | Walkenhorst et al. |
| 9,381,008 B2 | 7/2016 | Thornburg |
| 9,386,916 B2 | 7/2016 | Predick et al. |
| 9,387,092 B2 | 7/2016 | Mermuys et al. |
| 9,402,673 B2 | 8/2016 | Cormier et al. |
| 9,402,739 B2 | 8/2016 | Weiman et al. |
| 9,408,596 B2 | 8/2016 | Blain |
| 9,408,708 B2 | 8/2016 | Greenhalgh |
| 9,414,828 B2 | 8/2016 | Abidin et al. |
| 9,414,934 B2 | 8/2016 | Cain |
| 9,414,937 B2 | 8/2016 | Carlson et al. |
| 9,421,110 B2 | 8/2016 | Masson et al. |
| 9,427,331 B2 | 8/2016 | Arnin |
| 9,445,919 B2 | 9/2016 | Palmatier et al. |
| 9,452,063 B2 | 9/2016 | Glerum et al. |
| 9,456,903 B2 | 10/2016 | Glerum et al. |
| 9,456,906 B2 | 10/2016 | Gray et al. |
| 9,468,405 B2 | 10/2016 | Miles et al. |
| 9,474,622 B2 | 10/2016 | McLaughlin et al. |
| 9,474,625 B2 | 10/2016 | Weiman |
| 9,480,573 B2 | 11/2016 | Perloff et al. |
| 9,480,576 B2 | 11/2016 | Pepper et al. |
| 9,480,579 B2 | 11/2016 | Davenport et al. |
| 9,486,133 B2 | 11/2016 | Lee et al. |
| 9,486,325 B2 | 11/2016 | Davenport et al. |
| 9,486,327 B2 | 11/2016 | Martynova et al. |
| 9,486,328 B2 | 11/2016 | Jimenez et al. |
| 9,492,287 B2 | 11/2016 | Glerum et al. |
| 9,492,288 B2 | 11/2016 | Wagner et al. |
| 9,492,289 B2 | 11/2016 | Davenport et al. |
| 9,498,349 B2 | 11/2016 | Patterson et al. |
| 9,510,954 B2 | 12/2016 | Glerum et al. |
| 9,517,098 B2 | 12/2016 | Anderson |
| 9,522,070 B2 | 12/2016 | Flower et al. |
| 9,526,620 B2 | 12/2016 | Slivka et al. |
| 9,526,625 B2 | 12/2016 | Cain |
| 9,532,821 B2 | 1/2017 | Moskowitz et al. |
| 9,539,103 B2 | 1/2017 | McLaughlin et al. |
| 9,539,108 B2 | 1/2017 | Glerum et al. |
| 9,545,320 B2 | 1/2017 | Padovani et al. |
| 9,549,723 B2 | 1/2017 | Hynes et al. |
| 9,549,824 B2 | 1/2017 | McAfee |
| 9,561,116 B2 | 2/2017 | Weiman et al. |
| 9,566,163 B2 | 2/2017 | Suddaby et al. |
| 9,566,166 B2 | 2/2017 | Parry et al. |
| 9,566,168 B2 | 2/2017 | Glerum et al. |
| 9,572,560 B2 | 2/2017 | Mast et al. |
| 9,572,677 B2 | 2/2017 | Davenport et al. |
| 9,572,681 B2 | 2/2017 | Mathieu et al. |
| 9,579,124 B2 | 2/2017 | Gordon et al. |
| 9,579,139 B2 | 2/2017 | Cormier et al. |
| 9,579,213 B2 | 2/2017 | Bal et al. |
| 9,585,649 B2 | 3/2017 | Blain et al. |
| 9,585,762 B2 | 3/2017 | Suddaby et al. |
| 9,585,766 B2 | 3/2017 | Robinson |
| 9,585,767 B2 | 3/2017 | Robinson |
| 9,592,129 B2 | 3/2017 | Slivka et al. |
| 9,597,195 B2 | 3/2017 | Cain |
| 9,603,643 B2 | 3/2017 | Reed et al. |
| 9,603,713 B2 | 3/2017 | Moskowitz et al. |
| 9,603,717 B2 | 3/2017 | Ibarra et al. |
| 9,615,818 B2 | 4/2017 | Baudouin et al. |
| 9,615,936 B2 | 4/2017 | Duffield et al. |
| 9,622,732 B2 | 4/2017 | Martinelli et al. |
| 9,622,875 B2 | 4/2017 | Moskowitz et al. |
| 9,622,876 B1 | 4/2017 | Greenhalgh et al. |
| 9,629,729 B2 | 4/2017 | Grimberg, Jr. et al. |
| 9,636,097 B2 | 5/2017 | Bass |
| 9,642,720 B2 | 5/2017 | Radcliffe et al. |
| 9,649,198 B2 | 5/2017 | Wolters et al. |
| 9,655,746 B2 | 5/2017 | Seifert |
| 9,655,747 B2 | 5/2017 | Glerum et al. |
| 9,662,224 B2 | 5/2017 | Weiman et al. |
| 9,668,784 B2 | 6/2017 | Brumfield et al. |
| 9,668,876 B2 | 6/2017 | Blain et al. |
| 9,668,879 B2 | 6/2017 | Jimenez et al. |
| 9,675,465 B2 | 6/2017 | Padovani et al. |
| 9,675,467 B2 | 6/2017 | Duffield et al. |
| 9,675,468 B1 | 6/2017 | Jensen |
| 9,693,871 B2 | 7/2017 | Richerme et al. |
| 9,700,428 B2 | 7/2017 | Niemiec et al. |
| 9,707,092 B2 | 7/2017 | Davenport et al. |
| 9,713,536 B2 | 7/2017 | Foley et al. |
| 9,717,601 B2 | 8/2017 | Miller |
| 9,730,684 B2 | 8/2017 | Beale et al. |
| 9,730,806 B2 | 8/2017 | Capote |
| 9,737,288 B2 | 8/2017 | Karpowicz et al. |
| 9,750,617 B2 | 9/2017 | Lim et al. |
| 9,750,618 B1 | 9/2017 | Daffinson et al. |
| 9,757,249 B2 | 9/2017 | Radcliffe et al. |
| 9,763,722 B2 | 9/2017 | Roybal |
| 9,770,343 B2 | 9/2017 | Weiman |
| 9,782,265 B2 | 10/2017 | Weiman et al. |
| 9,788,971 B1 | 10/2017 | Stein |
| 9,795,370 B2 | 10/2017 | O'Connell et al. |
| 9,795,371 B2 | 10/2017 | Miles et al. |
| 9,801,733 B2 | 10/2017 | Wolters et al. |
| 9,801,734 B1 | 10/2017 | Stein et al. |
| 9,808,352 B2 | 11/2017 | Suddaby et al. |
| 9,826,966 B2 | 11/2017 | Mast et al. |
| 9,827,024 B2 | 11/2017 | Cormier et al. |
| 9,827,107 B1 | 11/2017 | Arnin |
| 9,833,333 B2 | 12/2017 | Duffield et al. |
| 9,833,336 B2 | 12/2017 | Davenport et al. |
| 9,839,527 B2 | 12/2017 | Robinson |
| 9,839,528 B2 | 12/2017 | Weiman et al. |
| 9,848,993 B2 | 12/2017 | Moskowitz et al. |
| 9,848,996 B2 | 12/2017 | Faulhaber |
| 9,855,151 B2 | 1/2018 | Weiman |
| 9,867,715 B2 | 1/2018 | McLaughlin et al. |
| 9,872,779 B2 | 1/2018 | Miller et al. |
| 9,889,019 B2 | 2/2018 | Rogers et al. |
| 9,907,671 B2 | 3/2018 | Fessler |
| 9,907,673 B2 | 3/2018 | Weiman et al. |
| 9,918,709 B2 | 3/2018 | Sandhu |
| 9,924,859 B2 | 3/2018 | Lee et al. |
| 9,924,940 B2 | 3/2018 | Moskowitz et al. |
| 9,925,062 B2 | 3/2018 | Glerum et al. |
| 9,925,064 B2 | 3/2018 | Duffield et al. |
| 9,931,223 B2 | 4/2018 | Cain |
| 9,937,053 B2 | 4/2018 | Melkent et al. |
| 9,943,342 B2 | 4/2018 | Tanaka et al. |
| 9,943,418 B2 | 4/2018 | Davenport et al. |
| 9,949,775 B2 | 4/2018 | Reed et al. |
| 9,949,841 B2 | 4/2018 | Glerum et al. |
| 9,956,087 B2 | 5/2018 | Seifert et al. |
| 9,962,202 B2 | 5/2018 | Anderson |
| 9,962,270 B2 | 5/2018 | Alheidt et al. |
| 9,962,271 B2 | 5/2018 | Glerum |
| 9,962,272 B1 | 5/2018 | Daffinson et al. |
| 9,968,461 B2 | 5/2018 | Zappacosta et al. |
| 9,968,462 B2 | 5/2018 | Weiman |
| 9,974,531 B2 | 5/2018 | Miles et al. |
| 9,974,662 B2 | 5/2018 | Hessler et al. |
| 9,974,664 B2 | 5/2018 | Emerick et al. |
| 9,980,825 B2 | 5/2018 | Nichols et al. |
| 9,980,826 B2 | 5/2018 | Martynova et al. |
| 9,987,141 B2 | 6/2018 | Duffield et al. |
| 9,987,143 B2 | 6/2018 | Robinson et al. |
| 9,987,144 B2 | 6/2018 | Seifert et al. |
| 9,987,146 B1 | 6/2018 | Lentner et al. |
| 9,993,239 B2 | 6/2018 | Karpowicz et al. |
| 9,993,350 B2 | 6/2018 | Cain |
| 10,004,607 B2 | 6/2018 | Weiman et al. |
| 10,016,282 B2 | 7/2018 | Seifert et al. |
| 10,016,284 B2 | 7/2018 | Moskowitz et al. |
| 10,022,239 B1 | 7/2018 | Lentner et al. |
| 10,028,842 B2 | 7/2018 | Gray et al. |
| 10,034,765 B2 | 7/2018 | Blain et al. |
| 10,034,769 B2 | 7/2018 | Baynham |
| 10,034,771 B2 | 7/2018 | Capote et al. |
| 10,034,772 B2 | 7/2018 | Glerum et al. |
| 10,034,773 B2 | 7/2018 | McLaughlin et al. |

(56) References Cited

U.S. PATENT DOCUMENTS

| | | |
|---|---|---|
| 10,039,539 B2 | 8/2018 | Friedrich et al. |
| 10,039,650 B2 | 8/2018 | Lamborne et al. |
| 10,052,214 B2 | 8/2018 | Jimenez et al. |
| 10,058,431 B2 | 8/2018 | Tyber et al. |
| 10,060,469 B2 | 8/2018 | Jimenez et al. |
| 10,070,852 B2 | 9/2018 | Mast et al. |
| 10,076,320 B2 | 9/2018 | Mast et al. |
| 10,076,423 B2 | 9/2018 | Miller et al. |
| 10,080,666 B2 | 9/2018 | Suddaby et al. |
| 10,080,669 B2 | 9/2018 | Davenport et al. |
| 10,085,846 B2 | 10/2018 | Grotz |
| 10,085,849 B2 | 10/2018 | Weiman et al. |
| 10,092,417 B2 | 10/2018 | Weiman et al. |
| 10,098,758 B2 | 10/2018 | Matthews et al. |
| 10,098,759 B2 | 10/2018 | Weiman |
| 10,111,755 B2 | 10/2018 | Foley et al. |
| 10,111,758 B2 | 10/2018 | Robinson |
| 10,117,754 B2 | 11/2018 | Davenport et al. |
| 10,117,755 B2 | 11/2018 | Emerick et al. |
| 10,137,002 B2 | 11/2018 | Padovani et al. |
| 10,137,006 B2 | 11/2018 | Dewey et al. |
| 10,137,007 B2 | 11/2018 | Dewey et al. |
| 10,137,009 B2 | 11/2018 | Weiman et al. |
| 10,149,671 B2 | 12/2018 | Predick et al. |
| 10,149,710 B2 | 12/2018 | Tanaka et al. |
| 10,154,781 B2 | 12/2018 | Weiman |
| 10,154,912 B2 | 12/2018 | Glerum |
| 10,154,914 B2 | 12/2018 | Robinson |
| 10,159,584 B2 | 12/2018 | Carnes et al. |
| 10,166,117 B1 | 1/2019 | Daffinson et al. |
| 10,172,515 B2 | 1/2019 | Lee et al. |
| 10,172,652 B2 | 1/2019 | Woolley et al. |
| 10,178,987 B2 | 1/2019 | Predick et al. |
| 10,179,053 B2 | 1/2019 | Zappacosta et al. |
| 10,182,922 B2 | 1/2019 | Nichols et al. |
| 10,188,527 B2 | 1/2019 | Rogers et al. |
| 10,195,050 B2 | 2/2019 | Palmatier et al. |
| 10,201,431 B2 | 2/2019 | Slater et al. |
| 10,213,192 B2 | 2/2019 | Capote |
| 10,213,193 B2 | 2/2019 | Karpowicz et al. |
| 10,219,798 B2 | 3/2019 | Capote |
| 10,219,913 B2 | 3/2019 | Matthews et al. |
| 10,219,914 B2 | 3/2019 | Faulhaber |
| 10,219,915 B1 | 3/2019 | Stein |
| 10,226,356 B2 | 3/2019 | Grotz |
| 10,226,359 B2 | 3/2019 | Glerum et al. |
| 10,238,375 B2 | 3/2019 | O'Connell et al. |
| 10,238,383 B2 | 3/2019 | Moskowitz et al. |
| 10,238,503 B2 | 3/2019 | Branch et al. |
| 10,245,015 B2 | 4/2019 | Predick et al. |
| 10,251,643 B2 | 4/2019 | Moskowitz et al. |
| 10,265,191 B2 | 4/2019 | Lim et al. |
| 10,278,686 B2 | 5/2019 | Baudouin et al. |
| 10,278,786 B2 | 5/2019 | Friedrich et al. |
| 10,278,830 B1 | 5/2019 | Walker et al. |
| 10,278,831 B2 | 5/2019 | Sandul |
| 10,278,832 B2 | 5/2019 | Nichols et al. |
| 10,285,680 B2 | 5/2019 | Friedrich et al. |
| 10,285,819 B2 | 5/2019 | Greenhalgh |
| 10,285,824 B2 | 5/2019 | Robinson |
| 10,292,828 B2 | 5/2019 | Greenhalgh |
| 10,299,777 B2 | 5/2019 | Mast et al. |
| 10,299,934 B2 | 5/2019 | Seifert et al. |
| 10,299,937 B2 | 5/2019 | McAfee |
| 10,307,268 B2 | 6/2019 | Moskowitz et al. |
| 10,314,622 B2 | 6/2019 | Brumfield et al. |
| 10,314,719 B2 | 6/2019 | Hessler et al. |
| 10,322,007 B2 | 6/2019 | Masson et al. |
| 10,322,009 B2 | 6/2019 | Aghayev et al. |
| 10,327,909 B2 | 6/2019 | Baynham |
| 10,327,912 B1 | 6/2019 | Suddaby |
| 10,327,917 B2 | 6/2019 | Glerum et al. |
| 10,342,675 B2 | 7/2019 | Alheidt |
| 10,350,085 B2 | 7/2019 | Glerum et al. |
| 10,357,233 B2 | 7/2019 | Miles et al. |
| 10,363,142 B2 | 7/2019 | McClintock et al. |
| 10,363,144 B2 | 7/2019 | Overes et al. |
| 10,369,004 B2 | 8/2019 | Faulhaber |
| 10,369,008 B2 | 8/2019 | Jimenez et al. |
| 10,369,010 B2 | 8/2019 | Robinson et al. |
| 10,369,012 B2 | 8/2019 | Fessler |
| 10,376,377 B2 | 8/2019 | Seifert et al. |
| 10,390,962 B2 | 8/2019 | Weiman |
| 10,390,964 B2 | 8/2019 | Faulhaber |
| 10,398,563 B2 | 9/2019 | Engstrom |
| 10,398,566 B2 | 9/2019 | Olmos et al. |
| 10,413,419 B2 | 9/2019 | Thibodeau |
| 10,413,422 B2 | 9/2019 | Flower et al. |
| 10,413,423 B2 | 9/2019 | Overes et al. |
| 10,426,450 B2 | 10/2019 | Vogel et al. |
| 10,426,633 B2 | 10/2019 | Moskowitz et al. |
| 10,426,634 B1 | 10/2019 | Al-Jazaer et al. |
| 10,441,430 B2 | 10/2019 | Ludwig et al. |
| 10,449,056 B2 | 10/2019 | Cain |
| 10,456,122 B2 | 10/2019 | Koltz et al. |
| 10,470,894 B2 | 11/2019 | Foley et al. |
| 10,478,319 B2 | 11/2019 | Moskowitz et al. |
| 10,492,912 B2 | 12/2019 | Gregersen et al. |
| 10,492,922 B2 | 12/2019 | Mathieu et al. |
| 10,492,924 B2 | 12/2019 | Stein et al. |
| 10,500,064 B2 | 12/2019 | Robinson |
| 10,512,550 B2 | 12/2019 | Bechtel et al. |
| 10,517,645 B2 | 12/2019 | van der Pol |
| 10,524,924 B2 | 1/2020 | Davenport et al. |
| 10,531,903 B2 | 1/2020 | Daly et al. |
| 10,537,436 B2 | 1/2020 | Maguire et al. |
| 10,537,438 B2 | 1/2020 | Martynova et al. |
| 10,555,729 B1 | 2/2020 | Cole et al. |
| 10,561,411 B1 | 2/2020 | Cole et al. |
| 10,575,889 B2 | 3/2020 | Roybal |
| 10,575,960 B2 | 3/2020 | Duffield et al. |
| 10,582,959 B2 | 3/2020 | Langer et al. |
| 10,583,015 B2 | 3/2020 | Olmos et al. |
| 10,603,078 B2 | 3/2020 | Simpson et al. |
| 10,610,376 B2 | 4/2020 | Kuyler et al. |
| 10,624,757 B2 | 4/2020 | Bost et al. |
| 10,624,758 B2 | 4/2020 | Slivka et al. |
| 10,624,761 B2 | 4/2020 | Davenport et al. |
| 10,639,163 B2 | 5/2020 | Fyber et al. |
| 10,639,166 B2 | 5/2020 | Weiman et al. |
| 10,653,458 B2 | 5/2020 | Tanaka et al. |
| 10,667,925 B2 | 6/2020 | Emerick et al. |
| 10,667,927 B2 | 6/2020 | Lamborne et al. |
| 10,675,157 B2 | 6/2020 | Zakelj et al. |
| 10,682,241 B2 | 6/2020 | Glerum et al. |
| 10,687,963 B2 | 6/2020 | Jimenez et al. |
| 10,702,393 B2 | 7/2020 | Davenport et al. |
| 10,709,569 B2 | 7/2020 | McLaughlin et al. |
| 10,709,571 B2 | 7/2020 | Iott et al. |
| 10,709,572 B2 | 7/2020 | Daffinson et al. |
| 10,709,575 B2 | 7/2020 | Robinson |
| 10,722,377 B2 | 7/2020 | Glerum et al. |
| 10,722,379 B2 | 7/2020 | McLaughlin et al. |
| 10,729,561 B2 | 8/2020 | Glerum |
| 10,743,858 B1 | 8/2020 | Cole et al. |
| 10,744,002 B2 | 8/2020 | Glerum et al. |
| 10,758,366 B2 | 9/2020 | Daffinson et al. |
| 10,758,367 B2 | 9/2020 | Weiman et al. |
| 10,758,369 B2 | 9/2020 | Rogers et al. |
| 10,765,528 B2 | 9/2020 | Weiman et al. |
| 10,772,737 B2 | 9/2020 | Gray et al. |
| 10,779,955 B2 | 9/2020 | Kuyler et al. |
| 10,779,957 B2 | 9/2020 | Weiman et al. |
| 10,786,364 B2 | 9/2020 | Davenport et al. |
| 10,786,369 B2 | 9/2020 | Carnes et al. |
| 10,799,368 B2 | 10/2020 | Glerum et al. |
| 10,835,387 B2 | 11/2020 | Weiman et al. |
| 10,842,640 B2 | 11/2020 | Weiman et al. |
| 10,842,644 B2 | 11/2020 | Weiman et al. |
| 10,856,997 B2 | 12/2020 | Cowan et al. |
| 10,869,769 B2 | 12/2020 | Eisen et al. |
| 10,874,447 B2 | 12/2020 | Tanaka et al. |
| 10,874,522 B2 | 12/2020 | Weiman |
| 10,874,523 B2 | 12/2020 | Weiman et al. |

(56) References Cited

U.S. PATENT DOCUMENTS

| | | |
|---|---|---|
| 10,874,524 B2 | 12/2020 | Bjork |
| 10,881,524 B2 | 1/2021 | Eisen et al. |
| 10,881,531 B2 | 1/2021 | Berry |
| 10,888,431 B1 | 1/2021 | Robinson |
| 10,898,344 B2 | 1/2021 | Alheidt et al. |
| 10,898,346 B1 | 1/2021 | Suddaby |
| 10,925,656 B2 | 2/2021 | Cole et al. |
| 10,925,750 B2 | 2/2021 | Zappacosta et al. |
| 10,925,752 B2 | 2/2021 | Weiman |
| 10,932,920 B2 | 3/2021 | Dewey et al. |
| 10,940,014 B2 | 3/2021 | Greenhalgh |
| 10,945,858 B2 | 3/2021 | Bechtel et al. |
| 10,952,866 B2 | 3/2021 | Warren et al. |
| 10,959,855 B2 | 3/2021 | Miller et al. |
| 10,959,856 B2 | 3/2021 | Seifert et al. |
| 10,973,649 B2 | 4/2021 | Weiman et al. |
| 10,973,650 B2 | 4/2021 | Stein |
| 10,980,642 B2 | 4/2021 | Glerum et al. |
| 10,980,644 B2 | 4/2021 | Purcell et al. |
| 10,993,814 B2 | 5/2021 | Wolters |
| 11,007,067 B2 | 5/2021 | Masson et al. |
| 11,013,617 B2 | 5/2021 | Weiman et al. |
| 11,020,238 B2 | 6/2021 | Nichols et al. |
| 11,020,239 B2 | 6/2021 | Miller et al. |
| 11,026,804 B2 | 6/2021 | Jimenez et al. |
| 11,026,812 B2 | 6/2021 | Daffinson et al. |
| 11,033,401 B2 | 6/2021 | Shoshtaev |
| 11,033,402 B2 | 6/2021 | Melkent et al. |
| 11,033,404 B2 | 6/2021 | Faulhaber |
| 11,039,935 B2 | 6/2021 | McAfee |
| 11,045,326 B2 | 6/2021 | Seifert et al. |
| 11,045,327 B2 | 6/2021 | Nichols et al. |
| 11,051,949 B2 | 7/2021 | Walker et al. |
| 11,051,951 B2 | 7/2021 | Robinson et al. |
| 11,058,469 B2 | 7/2021 | Mahajan et al. |
| 11,065,127 B1 | 7/2021 | Lentner et al. |
| 11,065,129 B2 | 7/2021 | Sandul |
| 11,065,130 B2 | 7/2021 | Branch et al. |
| 11,076,966 B2 | 8/2021 | Faulhaber |
| 11,083,584 B2 | 8/2021 | Lauf et al. |
| 11,083,595 B2 | 8/2021 | Robinson |
| 11,090,167 B2 | 8/2021 | Emerick et al. |
| 11,096,795 B2 | 8/2021 | Padovani et al. |
| 11,096,797 B2 | 8/2021 | Moskowitz et al. |
| 11,103,366 B2 | 8/2021 | Glerum et al. |
| RE48,719 E | 9/2021 | Suddaby et al. |
| 11,109,980 B2 | 9/2021 | Seifert et al. |
| 11,116,644 B2 | 9/2021 | Marrocco et al. |
| 11,123,198 B2 | 9/2021 | Black et al. |
| 11,123,200 B2 | 9/2021 | Faulhaber |
| 11,129,731 B2 | 9/2021 | Miller et al. |
| 11,135,071 B2 | 10/2021 | Dewey et al. |
| 11,147,680 B2 | 10/2021 | Tyber et al. |
| 11,154,404 B2 | 10/2021 | Freedman et al. |
| 11,160,666 B2 | 11/2021 | Burkhardt et al. |
| 11,160,669 B2 | 11/2021 | Rogers et al. |
| 11,166,826 B2 | 11/2021 | Huang |
| 11,173,044 B1 | 11/2021 | Jones et al. |
| 11,179,234 B2 | 11/2021 | Dacosta et al. |
| 11,285,014 B1 | 3/2022 | Josse et al. |
| 11,376,134 B1 | 7/2022 | Dewey et al. |
| 2002/0045943 A1 | 4/2002 | Uk |
| 2002/0045945 A1 | 4/2002 | Liu et al. |
| 2002/0055741 A1 | 5/2002 | Schlapfer et al. |
| 2002/0116066 A1 | 8/2002 | Chauvin et al. |
| 2002/0128713 A1 | 9/2002 | Ferree |
| 2002/0151976 A1 | 10/2002 | Foley et al. |
| 2002/0183762 A1* | 12/2002 | Anderson ......... A61B 17/0401 606/104 |
| 2003/0050701 A1 | 3/2003 | Michelson |
| 2003/0130739 A1 | 7/2003 | Gerbec et al. |
| 2003/0163132 A1 | 8/2003 | Chin |
| 2004/0102778 A1 | 5/2004 | Huebner et al. |
| 2004/0172134 A1 | 9/2004 | Berry |
| 2004/0186570 A1 | 9/2004 | Rapp |
| 2004/0193158 A1 | 9/2004 | Lim et al. |
| 2004/0204713 A1 | 10/2004 | Abdou |
| 2004/0249461 A1 | 12/2004 | Ferree |
| 2004/0254643 A1 | 12/2004 | Jackson |
| 2004/0254644 A1 | 12/2004 | Taylor |
| 2005/0015149 A1 | 1/2005 | Michelson |
| 2005/0033429 A1 | 2/2005 | Kuo |
| 2005/0033439 A1 | 2/2005 | Gordon et al. |
| 2005/0228398 A1* | 10/2005 | Rathbun ............ A61B 17/1728 606/96 |
| 2006/0122701 A1 | 6/2006 | Kiester |
| 2006/0129244 A1 | 6/2006 | Ensign |
| 2006/0260446 A1* | 11/2006 | Chang ............... B25B 23/0035 81/177.75 |
| 2007/0173840 A1 | 7/2007 | Huebner |
| 2007/0218750 A1 | 9/2007 | Corrao et al. |
| 2007/0233150 A1* | 10/2007 | Blain ..................... A61B 17/17 606/96 |
| 2007/0270859 A1 | 11/2007 | Companioni et al. |
| 2008/0058804 A1 | 3/2008 | Lechot et al. |
| 2008/0132959 A1 | 6/2008 | Mikkonen et al. |
| 2008/0140207 A1 | 6/2008 | Olmos et al. |
| 2009/0024158 A1 | 1/2009 | Viker |
| 2009/0292361 A1 | 11/2009 | Lopez |
| 2010/0076440 A1 | 3/2010 | Pamichev et al. |
| 2010/0082109 A1 | 4/2010 | Greenhalgh et al. |
| 2010/0152853 A1 | 6/2010 | Kirschman |
| 2010/0191336 A1 | 7/2010 | Greenhalgh |
| 2010/0211176 A1 | 8/2010 | Greenhalgh |
| 2010/0286777 A1 | 11/2010 | Errico et al. |
| 2011/0118843 A1 | 5/2011 | Mathieu et al. |
| 2011/0130838 A1 | 6/2011 | Morgenstern Lopez |
| 2011/0153020 A1 | 6/2011 | Abdelgany et al. |
| 2011/0218572 A1 | 9/2011 | Lechmann et al. |
| 2012/0004732 A1 | 1/2012 | Goel et al. |
| 2012/0095515 A1 | 4/2012 | Hamilton |
| 2012/0101581 A1 | 4/2012 | Mathieu et al. |
| 2012/0109142 A1 | 5/2012 | Dayan |
| 2012/0109309 A1 | 5/2012 | Mathieu et al. |
| 2012/0109310 A1 | 5/2012 | Mathieu et al. |
| 2012/0109312 A1 | 5/2012 | Mathieu et al. |
| 2012/0109313 A1 | 5/2012 | Mathieu et al. |
| 2012/0123546 A1 | 5/2012 | Medina |
| 2012/0143195 A1* | 6/2012 | Sander ................... F16D 3/207 464/106 |
| 2012/0150237 A1 | 6/2012 | Combrowski |
| 2012/0197401 A1 | 8/2012 | Duncan et al. |
| 2012/0209385 A1 | 8/2012 | Aferzon |
| 2012/0215313 A1 | 8/2012 | Saidha et al. |
| 2012/0215316 A1 | 8/2012 | Mohr et al. |
| 2013/0158664 A1 | 6/2013 | Palmatier et al. |
| 2013/0184823 A1 | 7/2013 | Malberg |
| 2013/0190876 A1 | 7/2013 | Drochner et al. |
| 2013/0211526 A1 | 8/2013 | Alheidt et al. |
| 2013/0226191 A1 | 8/2013 | Thoren et al. |
| 2013/0231747 A1 | 9/2013 | Olmos et al. |
| 2013/0304136 A1 | 11/2013 | Gourlaouen-Preissler et al. |
| 2013/0317312 A1 | 11/2013 | Eastlack et al. |
| 2014/0018816 A1* | 1/2014 | Fenn .................. B25B 23/0035 606/104 |
| 2014/0107790 A1 | 4/2014 | Combrowski |
| 2014/0114321 A1* | 4/2014 | Davenport ............ A61F 2/4609 606/91 |
| 2014/0114420 A1 | 4/2014 | Robinson |
| 2014/0148904 A1 | 5/2014 | Robinson |
| 2014/0163682 A1 | 6/2014 | Iott et al. |
| 2014/0180419 A1 | 6/2014 | Dmuschewsky |
| 2014/0194992 A1 | 7/2014 | Medina |
| 2014/0249631 A1 | 9/2014 | Weiman |
| 2014/0277471 A1 | 9/2014 | Gray et al. |
| 2014/0277487 A1 | 9/2014 | Davenport et al. |
| 2014/0277500 A1 | 9/2014 | Logan et al. |
| 2014/0303674 A1 | 10/2014 | Sasing |
| 2014/0364855 A1* | 12/2014 | Stoll .................. A61B 17/1615 606/80 |
| 2015/0223945 A1 | 8/2015 | Weiman et al. |
| 2015/0230931 A1 | 8/2015 | Greenhalgh |
| 2015/0238236 A1 | 8/2015 | Sasing |

(56) References Cited

U.S. PATENT DOCUMENTS

| | | | |
|---|---|---|---|
| 2015/0354635 A1* | 12/2015 | Mcclymont | A61B 17/1631 408/126 |
| 2016/0008924 A1 | 1/2016 | Canourgues et al. | |
| 2016/0022434 A1 | 1/2016 | Robinson | |
| 2016/0058571 A1 | 3/2016 | McLaughlin et al. | |
| 2016/0081681 A1 | 3/2016 | Waugh et al. | |
| 2016/0089247 A1 | 3/2016 | Nichols et al. | |
| 2016/0095710 A1 | 4/2016 | Juszczyk et al. | |
| 2016/0095718 A1 | 4/2016 | Burkhardt et al. | |
| 2016/0199073 A1* | 7/2016 | Nino | A61B 17/3496 606/184 |
| 2016/0242930 A1 | 8/2016 | Duffield et al. | |
| 2016/0256291 A1 | 9/2016 | Miller | |
| 2016/0278830 A1 | 9/2016 | Arrington | |
| 2016/0296340 A1 | 10/2016 | Gordon et al. | |
| 2016/0310291 A1 | 10/2016 | Greenhalgh | |
| 2016/0345952 A1 | 12/2016 | Kucharzyk et al. | |
| 2016/0367377 A1 | 12/2016 | Faulhaber | |
| 2017/0010025 A1 | 1/2017 | Mayershofer | |
| 2017/0029635 A1 | 2/2017 | Doll et al. | |
| 2017/0035406 A1 | 2/2017 | Abidin et al. | |
| 2017/0049651 A1 | 2/2017 | Lim et al. | |
| 2017/0049653 A1 | 2/2017 | Lim et al. | |
| 2017/0095345 A1 | 4/2017 | Davenport et al. | |
| 2017/0100255 A1 | 4/2017 | Hleihil et al. | |
| 2017/0100257 A1 | 4/2017 | Weiman et al. | |
| 2017/0105844 A1 | 4/2017 | Kuyler et al. | |
| 2017/0112630 A1 | 4/2017 | Kuyler et al. | |
| 2017/0151065 A1 | 6/2017 | Warren et al. | |
| 2017/0156882 A1 | 6/2017 | Rathbun et al. | |
| 2017/0156884 A1 | 6/2017 | Rathbun et al. | |
| 2017/0189204 A1 | 7/2017 | Riemhofer et al. | |
| 2017/0202678 A1 | 7/2017 | Duffield et al. | |
| 2017/0215856 A1 | 8/2017 | Martinelli et al. | |
| 2017/0224502 A1 | 8/2017 | Wolters et al. | |
| 2017/0224504 A1 | 8/2017 | Butler et al. | |
| 2017/0231675 A1 | 8/2017 | Combrowski | |
| 2017/0246006 A1 | 8/2017 | Carnes et al. | |
| 2017/0290677 A1 | 10/2017 | Olmos et al. | |
| 2017/0296352 A1 | 10/2017 | Richerme et al. | |
| 2017/0367842 A1 | 12/2017 | Predick et al. | |
| 2017/0367843 A1 | 12/2017 | Eisen et al. | |
| 2017/0367844 A1 | 12/2017 | Eisen et al. | |
| 2017/0367845 A1 | 12/2017 | Eisen et al. | |
| 2018/0000606 A1 | 1/2018 | Hessler et al. | |
| 2018/0030362 A1 | 2/2018 | Kosler et al. | |
| 2018/0031810 A1 | 2/2018 | Hsu et al. | |
| 2018/0036136 A1 | 2/2018 | Duffield et al. | |
| 2018/0036138 A1 | 2/2018 | Robinson | |
| 2018/0104066 A1 | 4/2018 | Bae et al. | |
| 2018/0116891 A1 | 5/2018 | Beale et al. | |
| 2018/0193160 A1 | 7/2018 | Hsu et al. | |
| 2018/0193164 A1 | 7/2018 | Shoshtaev | |
| 2018/0206999 A1 | 7/2018 | Suddaby | |
| 2018/0256356 A1 | 9/2018 | Robinson et al. | |
| 2018/0256359 A1 | 9/2018 | Greenhalgh | |
| 2018/0256360 A1 | 9/2018 | Cain | |
| 2018/0256362 A1 | 9/2018 | Slivka et al. | |
| 2018/0263784 A1 | 9/2018 | Bechtel et al. | |
| 2018/0280142 A1 | 10/2018 | Schultz et al. | |
| 2018/0303473 A1 | 10/2018 | Spann et al. | |
| 2018/0303621 A1 | 10/2018 | Brotman et al. | |
| 2018/0303625 A1 | 10/2018 | Alheidt et al. | |
| 2018/0311048 A1 | 11/2018 | Glerum et al. | |
| 2018/0318101 A1 | 11/2018 | Engstrom | |
| 2018/0318102 A1 | 11/2018 | Seifert et al. | |
| 2018/0325574 A1* | 11/2018 | Bjork | A61B 17/1631 |
| 2018/0338838 A1 | 11/2018 | Cryder et al. | |
| 2018/0338841 A1 | 11/2018 | Miller et al. | |
| 2018/0344307 A1 | 12/2018 | Hynes et al. | |
| 2018/0360616 A1 | 12/2018 | Luu | |
| 2019/0000640 A1 | 1/2019 | Weiman | |
| 2019/0000702 A1 | 1/2019 | Lim et al. | |
| 2019/0000707 A1 | 1/2019 | Lim et al. | |
| 2019/0020121 A1 | 1/2019 | Paulotto et al. | |
| 2019/0021716 A1 | 1/2019 | Waugh et al. | |
| 2019/0021873 A1 | 1/2019 | Dmuschewsky | |
| 2019/0046329 A1 | 2/2019 | Padovani et al. | |
| 2019/0046381 A1 | 2/2019 | Lim et al. | |
| 2019/0046383 A1 | 2/2019 | Lim et al. | |
| 2019/0060083 A1 | 2/2019 | Weiman et al. | |
| 2019/0082949 A1 | 3/2019 | Weiman | |
| 2019/0083081 A1 | 3/2019 | Ortiz et al. | |
| 2019/0091033 A1 | 3/2019 | Dewey et al. | |
| 2019/0105175 A1 | 4/2019 | Zappacosta et al. | |
| 2019/0125328 A1 | 5/2019 | Blain | |
| 2019/0133434 A1 | 5/2019 | Lee et al. | |
| 2019/0133645 A1 | 5/2019 | Gordon et al. | |
| 2019/0133779 A1 | 5/2019 | McLaughlin et al. | |
| 2019/0133780 A1 | 5/2019 | Matthews et al. | |
| 2019/0133784 A1 | 5/2019 | Gunn et al. | |
| 2019/0133788 A1 | 5/2019 | Weiman et al. | |
| 2019/0142480 A1 | 5/2019 | Woolley et al. | |
| 2019/0151115 A1 | 5/2019 | Nichols et al. | |
| 2019/0183656 A1 | 6/2019 | Stein | |
| 2019/0201209 A1 | 7/2019 | Branch et al. | |
| 2019/0201210 A1 | 7/2019 | Besaw et al. | |
| 2019/0209155 A1 | 7/2019 | Mast et al. | |
| 2019/0216453 A1 | 7/2019 | Predick et al. | |
| 2019/0231552 A1 | 8/2019 | Sandul | |
| 2019/0240039 A1 | 8/2019 | Walker et al. | |
| 2019/0240043 A1 | 8/2019 | Greenhalgh | |
| 2019/0247098 A1 | 8/2019 | Brumfield et al. | |
| 2019/0254650 A1 | 8/2019 | Martinelli et al. | |
| 2019/0254838 A1 | 8/2019 | Miller et al. | |
| 2019/0254839 A1 | 8/2019 | Nichols et al. | |
| 2019/0262009 A1 | 8/2019 | Cheng | |
| 2019/0262139 A1 | 8/2019 | Wolters | |
| 2019/0269521 A1 | 9/2019 | Shoshtaev | |
| 2019/0274670 A1 | 9/2019 | O'Connell et al. | |
| 2019/0274671 A1 | 9/2019 | Lauf et al. | |
| 2019/0274836 A1 | 9/2019 | Eisen et al. | |
| 2019/0282373 A1 | 9/2019 | Alheidt | |
| 2019/0290446 A1 | 9/2019 | Masson et al. | |
| 2019/0290447 A1 | 9/2019 | Stein | |
| 2019/0298416 A1 | 10/2019 | Rezach | |
| 2019/0298524 A1 | 10/2019 | Lauf et al. | |
| 2019/0298540 A1 | 10/2019 | Aghayev et al. | |
| 2019/0321022 A1 | 10/2019 | Karpowicz et al. | |
| 2019/0321190 A1 | 10/2019 | Wagner et al. | |
| 2019/0328539 A1 | 10/2019 | Suh et al. | |
| 2019/0328540 A1* | 10/2019 | Seifert | A61F 2/447 |
| 2019/0329388 A1 | 10/2019 | Erickson et al. | |
| 2019/0336301 A1 | 11/2019 | Engstrom | |
| 2019/0336304 A1 | 11/2019 | Burkhardt et al. | |
| 2019/0350573 A1 | 11/2019 | Vogel et al. | |
| 2019/0358049 A1 | 11/2019 | Faulhaber | |
| 2019/0358050 A1 | 11/2019 | Fessler | |
| 2019/0358051 A1 | 11/2019 | Flower et al. | |
| 2019/0380840 A1 | 12/2019 | Tyber et al. | |
| 2019/0388232 A1 | 12/2019 | Purcell et al. | |
| 2020/0008951 A1 | 1/2020 | McClintock et al. | |
| 2020/0030114 A1 | 1/2020 | Cain | |
| 2020/0030116 A1 | 1/2020 | Jimenez et al. | |
| 2020/0038200 A1 | 2/2020 | Foley et al. | |
| 2020/0054461 A1 | 2/2020 | Marrocco et al. | |
| 2020/0060844 A1 | 2/2020 | Mathieu et al. | |
| 2020/0069316 A1* | 3/2020 | DeSoutter | A61B 17/162 |
| 2020/0078190 A1 | 3/2020 | Rogers et al. | |
| 2020/0093526 A1 | 3/2020 | Daly et al. | |
| 2020/0093607 A1 | 3/2020 | Davenport et al. | |
| 2020/0093609 A1 | 3/2020 | Shoshtaev | |
| 2020/0100904 A1 | 4/2020 | Stein et al. | |
| 2020/0129306 A1 | 4/2020 | Miller et al. | |
| 2020/0129307 A1 | 4/2020 | Hunziker et al. | |
| 2020/0138591 A1 | 5/2020 | Moskowitz et al. | |
| 2020/0138593 A1 | 5/2020 | Martynova et al. | |
| 2020/0146840 A1 | 5/2020 | Black et al. | |
| 2020/0179120 A1 | 6/2020 | Bielenstein et al. | |
| 2020/0205993 A1 | 7/2020 | Davenport et al. | |
| 2020/0214754 A1* | 7/2020 | Bowen | A61B 17/1631 |
| 2020/0222202 A1 | 7/2020 | Kuyler et al. | |
| 2020/0229944 A1 | 7/2020 | Suh et al. | |
| 2020/0246159 A1 | 8/2020 | Suh et al. | |

(56) References Cited

U.S. PATENT DOCUMENTS

| | | |
|---|---|---|
| 2020/0246162 A1 | 8/2020 | Schultz et al. |
| 2020/0261242 A1 | 8/2020 | Bost et al. |
| 2020/0268524 A1 | 8/2020 | Glerum et al. |
| 2020/0276028 A1 | 9/2020 | Blain et al. |
| 2020/0281741 A1 | 9/2020 | Grotz |
| 2020/0289287 A1 | 9/2020 | Emerick et al. |
| 2020/0297507 A1 | 9/2020 | Iott et al. |
| 2020/0330239 A1 | 10/2020 | Davenport et al. |
| 2020/0330245 A1 | 10/2020 | Glerum |
| 2020/0345511 A1 | 11/2020 | Daffinson et al. |
| 2020/0352731 A1 | 11/2020 | Berry |
| 2020/0352738 A1 | 11/2020 | Berry |
| 2020/0360153 A1 | 11/2020 | Weiman et al. |
| 2020/0375753 A1 | 12/2020 | McLaughlin et al. |
| 2020/0375755 A1 | 12/2020 | Cain |
| 2020/0383797 A1 | 12/2020 | Predick et al. |
| 2020/0383799 A1 | 12/2020 | Cain |
| 2020/0390565 A1 | 12/2020 | Jimenez et al. |
| 2020/0397593 A1 | 12/2020 | Davenport et al. |
| 2020/0405497 A1 | 12/2020 | Olmos et al. |
| 2020/0405498 A1 | 12/2020 | Gray et al. |
| 2020/0405499 A1 | 12/2020 | Gerbec et al. |
| 2020/0405500 A1 | 12/2020 | Cain |
| 2021/0007860 A1 | 1/2021 | Glerum et al. |
| 2021/0015626 A1 | 1/2021 | Suddaby |
| 2021/0030555 A1 | 2/2021 | Weiman et al. |
| 2021/0030561 A1 | 2/2021 | Gleason |
| 2021/0045891 A1 | 2/2021 | Rogers et al. |
| 2021/0045892 A1 | 2/2021 | Rogers et al. |
| 2021/0052395 A1 | 2/2021 | Iott et al. |
| 2021/0068959 A1 | 3/2021 | McLuen et al. |
| 2021/0068974 A1 | 3/2021 | Cowan et al. |
| 2021/0068982 A1 | 3/2021 | Carnes et al. |
| 2021/0077271 A1 | 3/2021 | Sharabani |
| 2021/0077272 A1 | 3/2021 | Eisen et al. |
| 2021/0085479 A1 | 3/2021 | Weiman et al. |
| 2021/0093462 A1 | 4/2021 | Lucasiewicz et al. |
| 2021/0106434 A1 | 4/2021 | Alheidt et al. |
| 2021/0113349 A1 | 4/2021 | Weiman et al. |
| 2021/0121299 A1 | 4/2021 | Hyder |
| 2021/0121300 A1 | 4/2021 | Weiman et al. |
| 2021/0137697 A1 | 5/2021 | Weiman |
| 2021/0137699 A1 | 5/2021 | Jang et al. |
| 2021/0137701 A1 | 5/2021 | Miller et al. |
| 2021/0154811 A1 | 5/2021 | Spreiter et al. |
| 2021/0161678 A1 | 6/2021 | Dewey et al. |
| 2021/0177618 A1 | 6/2021 | Branch et al. |
| 2021/0186706 A1 | 6/2021 | Spitler et al. |
| 2021/0186709 A1 | 6/2021 | Weiman et al. |
| 2021/0196470 A1 | 7/2021 | Shoshtaev |
| 2021/0205092 A1 | 7/2021 | Glerum et al. |
| 2021/0205094 A1 | 7/2021 | Weiman et al. |
| 2021/0220145 A1 | 7/2021 | Stein |
| 2021/0220147 A1 | 7/2021 | Berry |
| 2021/0236298 A1 | 8/2021 | Weiman et al. |
| 2021/0251770 A1 | 8/2021 | Purcell et al. |
| 2021/0251776 A1 | 8/2021 | Daffinson et al. |
| 2021/0259848 A1 | 8/2021 | Kang et al. |
| 2021/0259849 A1 | 8/2021 | Robinson et al. |
| 2021/0259850 A1 | 8/2021 | Eisen et al. |
| 2021/0267767 A1 | 9/2021 | Stein |
| 2021/0275317 A1 | 9/2021 | Spetzger |
| 2021/0275318 A1 | 9/2021 | Reimels |
| 2021/0275319 A1 | 9/2021 | Reimels |
| 2021/0275321 A1 | 9/2021 | Seifert et al. |
| 2021/0282938 A1 | 9/2021 | Nichols et al. |
| 2021/0298915 A1 | 9/2021 | Faulhaber |
| 2021/0298916 A1 | 9/2021 | Melkent et al. |
| 2021/0307920 A1 | 10/2021 | Walker et al. |
| 2021/0315705 A1 | 10/2021 | Altarac et al. |
| 2021/0322179 A1 | 10/2021 | Miller et al. |
| 2021/0322181 A1 | 10/2021 | Predick |
| 2021/0322182 A1 | 10/2021 | Faulhaber |
| 2021/0330472 A1 | 10/2021 | Shoshtaev |
| 2021/0346174 A1 | 11/2021 | Flint et al. |
| 2022/0015924 A1 | 1/2022 | Freedman et al. |
| 2022/0047312 A1* | 2/2022 | Seykora ............. A61B 17/1633 |
| 2022/0133336 A1* | 5/2022 | Tsai .................... A61B 17/162 |
| | | 606/80 |
| 2022/0133498 A1 | 5/2022 | Josse et al. |
| 2022/0133499 A1 | 5/2022 | Josse et al. |
| 2022/0387184 A1 | 12/2022 | Josse et al. |

FOREIGN PATENT DOCUMENTS

| | | |
|---|---|---|
| EP | 0 880 950 A1 | 12/1998 |
| EP | 0 767 636 B1 | 1/1999 |
| EP | 0 857 042 B1 | 11/2001 |
| EP | 1 442 732 A1 | 8/2004 |
| EP | 1 124 512 B1 | 9/2004 |
| EP | 1 107 711 B1 | 10/2004 |
| EP | 1 506 753 A1 | 2/2005 |
| EP | 1 459 711 B1 | 7/2007 |
| EP | 2954860 A2 | 12/2015 |
| EP | 3031424 A1 | 6/2016 |
| EP | 3 069 694 A1 | 9/2016 |
| EP | 3213720 A1 | 9/2017 |
| FR | 2781998 A1 | 2/2000 |
| FR | 3082115 A1 | 12/2019 |
| GB | 2 377 387 A | 1/2003 |
| KR | 102192022 B1 | 12/2020 |
| WO | 92/14423 A1 | 9/1992 |
| WO | 97/ 00054 A1 | 1/1997 |
| WO | 99/ 26562 A1 | 6/1999 |
| WO | 99/66867 A1 | 12/1999 |
| WO | 00/12033 A1 | 3/2000 |
| WO | 00/25706 A1 | 5/2000 |
| WO | 00/ 49977 A1 | 8/2000 |
| WO | 02/19952 A1 | 3/2002 |
| WO | 03/105673 A2 | 12/2003 |
| WO | 2006116850 A1 | 11/2006 |
| WO | 2012139022 A2 | 10/2012 |
| WO | 2014/133755 A1 | 9/2014 |
| WO | 2015063721 A1 | 5/2015 |
| WO | 2015198335 A1 | 12/2015 |
| WO | 2016057940 A1 | 4/2016 |
| WO | 2017/168208 A1 | 10/2017 |
| WO | 2018049227 A1 | 3/2018 |
| WO | 2021055323 A1 | 3/2021 |

OTHER PUBLICATIONS

International Search Report and Written Opinion for Application No. PCT/US2019/019060, dated Jun. 5, 2019.
International Search Report and Written Opinion, PCT/IB2020/000932, dated Jul. 29, 2021.
International Search Report and Written Opinion, PCT/IB2020/000942, dated Aug. 10, 2021.
International Search Report and Written Opinion in Application No. PCT/US2022/027200 dated Aug. 19, 2022.
International Search Report and Written Opinion in Application No. PCT/US2022/016809 dated Jul. 27, 2022.
International Search Report and Written Opinion in Application No. PCT/US2022/027695 dated Jul. 27, 2022.
International Search Report and Written Opinion in Application No. PCT/US2022/016831 dated Sep. 29, 2022.
International Search Report and Written Opinion in Application No. PCT/US2022/030094 dated Sep. 16, 2022.

* cited by examiner

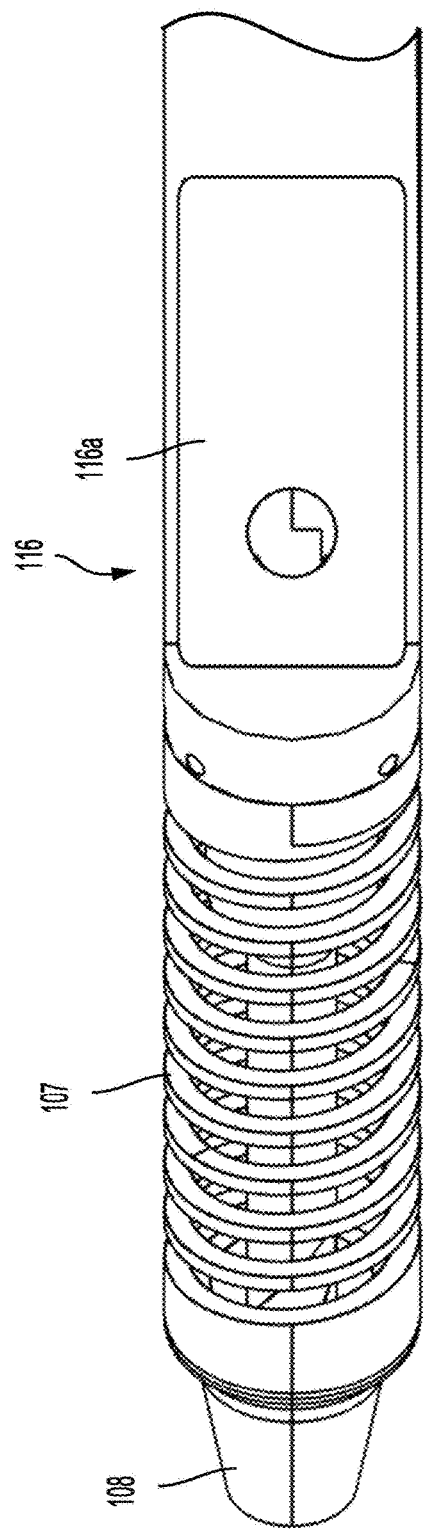
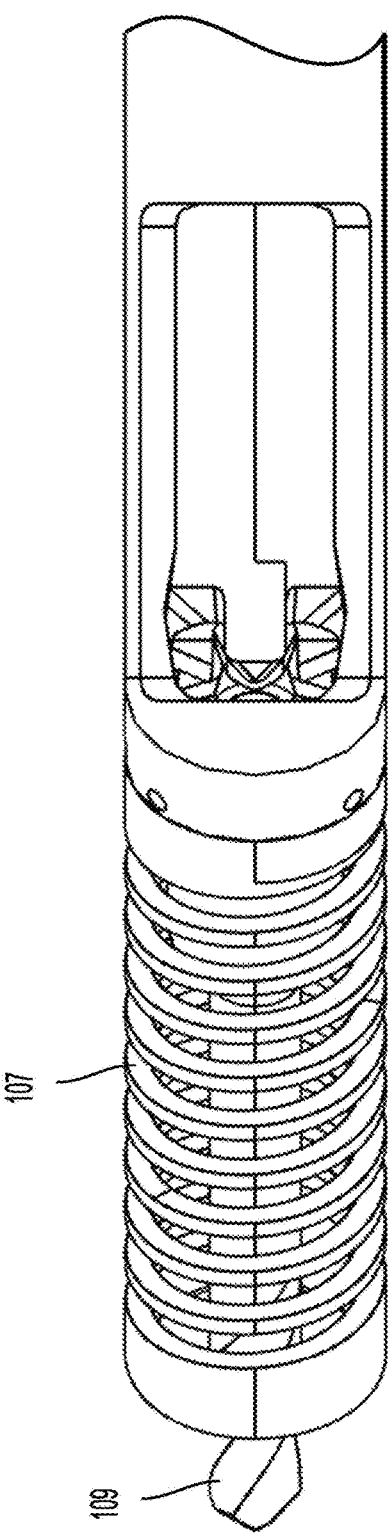
FIG. 4A
FIG. 4B

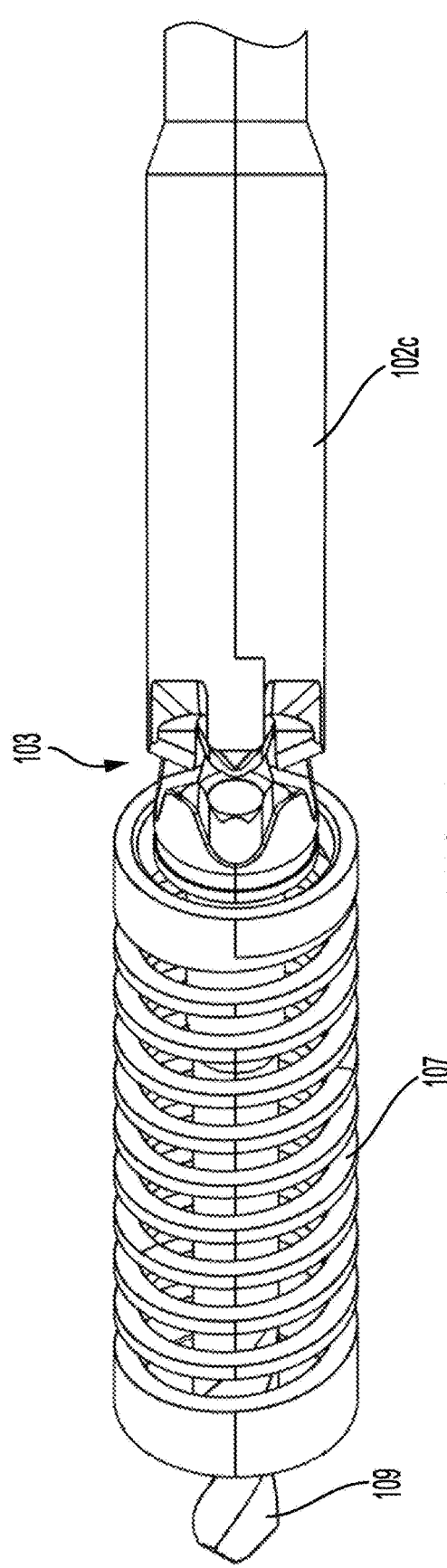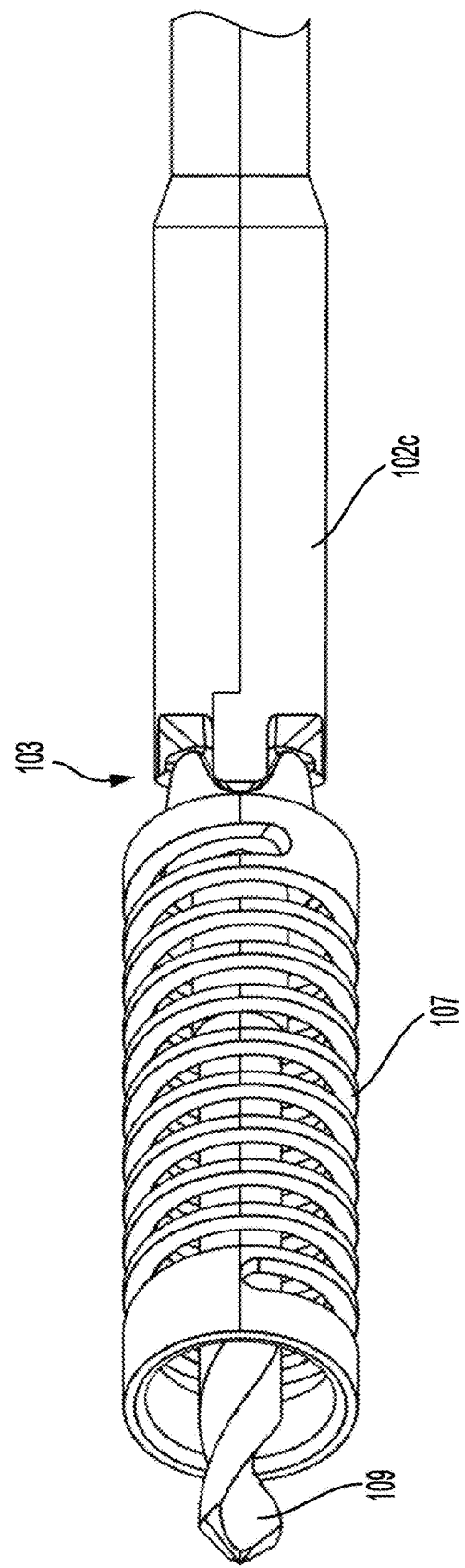
FIG. 6A
FIG. 6B

SURGERY INSTRUMENTS WITH A MOVABLE HANDLE

CROSS-REFERENCE TO RELATED APPLICATIONS

This application is a continuation in part of (U.S. application Ser. No. 17/181,556, titled Protected Drill, filed Feb. 22, 2021, which is a continuation in part of U.S. patent application Ser. No. 17/123,906, titled Screwdriver and Complimentary Screws, filed Dec. 16, 2020, which claims priority to and incorporates by reference co-related patent applications, PCT/FR2020/000257, titled Expandable Inter-Body Device, System, and Method, filed Nov. 5, 2020; PCT/FR2020/000259, titled Screwdriver and Complimentary Screws, filed Nov. 5, 2020; and PCT/FR2020/000258, titled Expandable Inter-Body Device, System, and Method, filed Nov. 5, 2020. The contents of each application listed above is hereby incorporated in its entirety. Additionally, this application incorporates by reference the entire contents of U.S. Pat. No. 10,456,122, titled Surgical system including powered rotary-type handpiece, filed Mar. 13, 2013.

FIELD

In one aspect, the present technology is generally related to surgical instruments including a movable handle affording a greater degree of control for various surgical approaches. In another aspect, the present technology is related to a drill having a protected end for protecting patient tissue from a drill bit. In another aspect, the present technology is generally related to screwdrivers for installing, removing, and/or manipulating complimentary bone screws.

BACKGROUND

The installation and insertion of bone screws in a patient poses many risks. At least one risk is the pre-operative step of drilling a passageway for a bone screw safely within a surgical opening of a patient, for example. Conventional drills may have sharp edges and a cutting tip that can cause accidental injuries to a patient. For example, in operation, an edge of a drill bit may catch an adjacent surface or "walk" away from an intended drill site and damage adjacent soft tissues. These problems may occur in all surgical settings requiring a drill although are particularly problematic in mini open surgeries and other minimally invasive surgical techniques, for example.

The installation and insertion of bone screws in a patient poses many risks. Some of these risks may include the loss of a bone screw in the patient, which can have dramatic consequences and even lead to death in some cases. Additionally, conventional screwdrivers and related tools are often unsuitable for avoiding anatomical features, such as the pelvic ring, rib cage, iliac crest, etc., for example. Additionally, conventional screwdrivers are not be well suited for installation of bone screws in angled bone plates and/or angled apertures of spinal implants, for example. There is a need for screwdrivers that can securely connect to a complimentary bone screw with sufficient force that the bone screw will not become accidentally detached during the initial positioning and installation of the bone screw. Additionally, there is a need for screwdrivers that are optimized for the installation of bone screws to secure spinal implants to adjacent vertebrae of a patient according to various surgical techniques including anterior techniques, lateral techniques, and oblique techniques.

The length of surgical instruments is usually dictated by the approach and methodology. For example, a posterior approach versus anterior approach and a lumbar approach versus a cervical approach, for example. Conventional surgical instruments are relatively long and may not be optimal with all patient anatomy and sizes and/or operator anatomy and sizes. At least one drawback of certain conventional surgical tools is that handles are fixed and typically positioned far away from the distal end thus reducing the precision of use which can lead to taking a longer time for certain surgeries and require additional care to avoid risks to the patient.

SUMMARY

In one aspect, a drill is disclosed. The drill may extend from a distal end to a proximal end and include a housing extending in a longitudinal direction, for example. The drill may have a rotatable drive shaft including a first drive end disposed at the proximal end of the drill that is configured for coupling to a driver, for example. The rotatable drive shaft may have a main shaft portion extending in the longitudinal direction through the housing between the first drive end and a second drive end, for example. The drill may further include an angled tip region defining the distal end of the drill, and the angled tip portion may have a drill bit coupler configured to receive a drill bit and orient the drill bit in an angled direction with respect to the longitudinal direction thereby defining a drilling axis of the drill bit, for example. The drill may further include a mechanism configured to transfer a rotational force applied to the first drive end through the second drive end and angled tip region to the drill bit coupler, for example. The drill may further include a movable handle mechanism coupled to and disposed at a medial portion of the housing, for example. The drill may further include a sleeve radially disposed at a distal end of the angled tip region and configured to radially surround at least a first portion of the drill bit when received in the drill bit coupler, for example.

In another aspect, the disclosure provides that the movable handle mechanism may include a positioning handle, for example.

In another aspect, the disclosure provides that the movable handle mechanism is configured to move forward and backward in a longitudinal direction along the housing, for example.

In another aspect, the disclosure provides that the housing includes a plurality of channels and the movable handle mechanism is configured to securely couple to the housing via at least one channel of the plurality of channels, for example.

In another aspect, the disclosure provides that the movable handle mechanism is configured to rotate clockwise and counterclockwise around the housing, for example.

In another aspect, the disclosure provides that the housing includes a plurality of detents, and the movable handle mechanism is configured to securely couple to the housing via at least one detent of the plurality of detents, for example.

In another aspect, the disclosure provides that the movable handle mechanism further comprises a positioning ball having a size and shape corresponding to a size and shape of a detent of the plurality of detents, for example. In various embodiments, the positioning ball may be configured to securely couple the movable handle mechanism via one detent of the plurality of detents, for example.

In another aspect, the disclosure provides that the movable handle mechanism is configured to move forward and backward in a longitudinal direction along the housing between a proximal stop ring and a distal stop ring and rotate clockwise and counterclockwise around the housing, for example.

In another aspect, the disclosure provides that the housing may include a plurality of channels and each channel of the plurality of channels may include at least one detent, for example Additionally, in various embodiments, the movable handle mechanism may be configured to securely couple to the housing via one channel of the plurality of channels and one detent of the plurality of detents, for example.

In another aspect, the disclosure provides that the movable handle mechanism may further include a positioning ball having a size and shape corresponding to a size and shape of a detent of the plurality of detents, for example. The positioning ball may be configured to securely couple the movable handle mechanism via one detent of the plurality of detents.

In another aspect, the disclosure provides that the angled tip region may further include a compressible spring contacting the sleeve and configured to bias the sleeve in the angled direction, for example. The compressible spring may be configured to surround at least a second portion of the drill bit when received in the drill bit coupler.

In another aspect, the disclosure provides that in various embodiments, in a first mode of operation where the spring is in a neutral position, the sleeve and compressible spring are configured to surround lateral sidewalls of the drill bit when received in the drill bit coupler, for example. In another aspect, the disclosure provides that in a second mode of operation, the compressible spring may be configured to compress in a direction parallel to the angled direction towards the mechanism, for example.

In one aspect, the present disclosure provides for a screwdriver, including: a rotatable drive shaft, the drive shaft including a drive portion disposed at a distal end thereof, a drive end disposed at a proximal end thereof, and a main shaft portion extending in a longitudinal direction through a housing; a movable handle mechanism coupled to and disposed at a medial portion of the housing; an angled tip portion disposed at the proximal end, the angled tip portion being angled with respect to the longitudinal direction, the drive end of the drive shaft extending through the angled tip portion; and a mechanism configured to transfer a rotational force applied to the drive portion of the drive shaft through the angled tip portion to the drive end of the drive shaft. The screwdriver may further include: an elastic retaining clip configured to have a bone screw securely attached therein at a clipping force and progressively release the bone screw therein at an extraction force, the elastic retaining clip being removably and operably coupled with the drive end of the drive shaft; and a first spring contacting the elastic retaining clip and the angled tip portion, the first spring being configured to facilitate the progressive release of the bone screw.

In another aspect, the disclosure provides that the movable handle mechanism includes a positioning handle, for example.

In another aspect, the disclosure provides that the movable handle mechanism may be configured to move forward and backward in a longitudinal direction along the housing.

In another aspect, the disclosure provides that the housing includes a plurality of channels and the movable handle mechanism is configured to securely couple to the housing via at least one channel of the plurality of channels, for example.

In another aspect, the disclosure provides that the movable handle mechanism is configured to rotate clockwise and counterclockwise around the housing, for example.

In another aspect, the disclosure provides that the housing includes a plurality of detents, and the movable handle mechanism is configured to securely couple to the housing via at least one detent of the plurality of detents, for example.

In another aspect, the disclosure provides that the movable handle mechanism further comprises a positioning ball having a size and shape corresponding to a size and shape of a detent of the plurality of detents, for example. In various embodiments, the positioning ball may be configured to securely couple the movable handle mechanism via one detent of the plurality of detents, for example.

In another aspect, the disclosure provides that the movable handle mechanism is configured to move forward and backward in a longitudinal direction along the housing between a proximal stop ring and a distal stop ring and rotate clockwise and counterclockwise around the housing, for example.

In another aspect, the disclosure provides that the housing may include a plurality of channels, and each channel of the plurality of channels may include at least one detent, for example. In another aspect, the disclosure provides that the movable handle mechanism may be configured to securely couple to the housing via one channel of the plurality of channels and one detent of the plurality of detents, for example.

In another aspect, the disclosure provides that the movable handle mechanism may include a positioning ball having a size and shape corresponding to a size and shape of a detent of the plurality of detents, for example. In various embodiments, the positioning ball may be configured to securely couple the movable handle mechanism via one detent of the plurality of detents, for example.

In another aspect, the disclosure provides that the movable handle mechanism is configured to move forward and backward in a longitudinal direction along the housing between a proximal stop ring and a distal stop ring, for example. In various embodiments, the movable handle mechanism is configured to rotate clockwise and counterclockwise around the housing, for example. In various embodiments, the housing includes a plurality of channels, each channel of the plurality of channels including at least one detent, and the movable handle mechanism is configured to securely couple to the housing via at least one channel of the plurality of channels and at least one detent of the plurality of detents, for example.

In another aspect, the present disclosure provides that the screwdriver further may include a second spring configured to facilitate the progressive release of the bone screw, that the first spring and second spring each contact the elastic retaining clip and the angled tip portion, and that the first spring is disposed, at least partly, within a central cavity of the second spring.

In another aspect, the present disclosure provides that the at least one protrusion may be radially inset with respect to a head portion of the bone screw and is configured to contact an end portion of the head portion of the bone screw to thereby facilitate the retention of the bone screw.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

FIG. 4A is a top down view of a flushing portion of an example drill in accordance with the principles of the present disclosure;

FIG. 4B is a top down view of a flushing portion of an example drill with partially removed parts for ease of understanding in accordance with the principles of the present disclosure;

FIG. 6A is a top view of a gear mechanism in accordance with the principles of the present disclosure;

FIG. 6B is a bottom view of a gear mechanism in accordance with the principles of the present disclosure;

FIG. 33 is a perspective view of an example medical device that includes bone screw apertures that example screwdrivers of the present disclosure may progressively drive a bone screw through.

DETAILED DESCRIPTION

Figure 1:
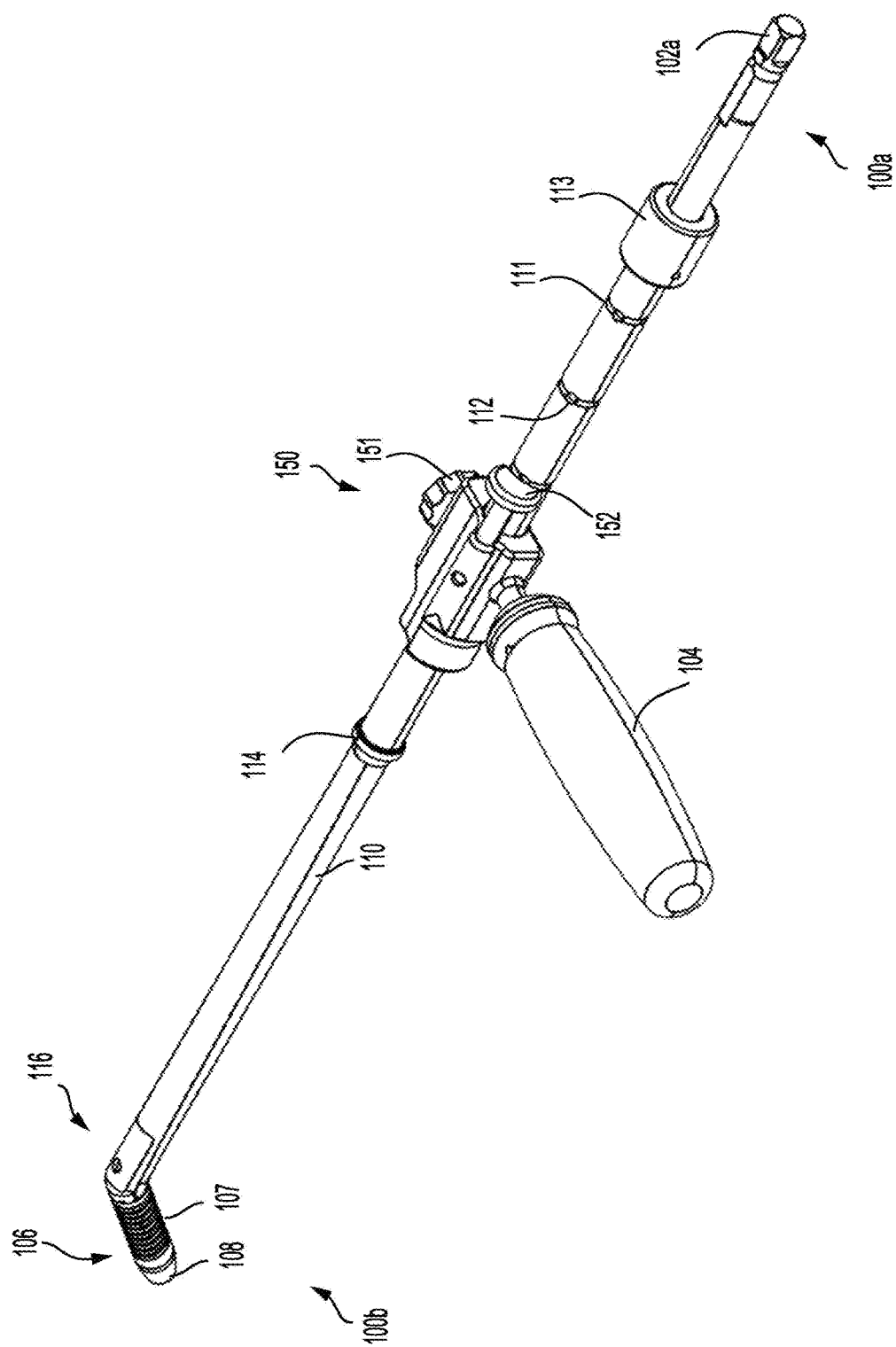
FIG. 1 is a perspective view of an example drill in accordance with the principles of the present disclosure.

As used herein, standard anatomical terms of location have their ordinary meaning as they would be understood by a person of ordinary skill in the art unless clearly defined or explained otherwise. It should be understood that various aspects disclosed herein may be combined in different combinations than the combinations specifically presented in the description and accompanying drawings. For example, characteristics of one embodiment may be combined or substituted with characteristics of another different embodiment unless those characteristics are clearly explained as being mutually exclusive. It should also be understood that, depending on the example, certain acts or events of any of the processes or methods described herein may be performed in a different sequence, may be added, merged, or left out altogether (e.g., all described acts or events may not be necessary to carry out the disclosed techniques and methods). In addition, while certain aspects of this disclosure are described as being performed by a single module, unit, or component for purposes of clarity, it should be understood that the techniques of this disclosure may be performed by a combination of units, modules, or components associated with, for example, a medical device such as a drill.

In some embodiments, the present disclosure is directed to surgical tools having a movable handle. For example, a surgical tool such as a drill and/or a screw driver having a movable handle that is optimized for a medical setting and can be readily used for various types of surgical techniques, including anterior surgical techniques, lateral surgical techniques, and oblique surgical techniques. In some embodiments, a surgical tool may be optimized to secure a spinal implant between adjacent vertebrae by securing at least one complimentary bone screw to the spinal implant and into an adjacent vertebrae. In some embodiments, and as mentioned above, the present disclosure may be employed in conjunction with spinal implants to treat spinal disorders such as, for example, degenerative disc disease, disc herniation, osteoporosis, spondylolisthesis, stenosis, scoliosis and other curvature abnormalities, kyphosis, tumor and fractures. In some embodiments, the present disclosure may be employed with other osteal and bone related applications, including those associated with diagnostics and therapeutics.

In some embodiments, the disclosed example surgical tools may be alternatively employed in a surgical treatment with a patient in a prone or supine position, and/or employ various surgical approaches to the spine, including anterior, posterior, posterior mid-line, direct lateral, postero-lateral oblique, and/or antero lateral oblique approaches, and in other body regions. The present disclosure may also be alternatively employed with procedures for treating the lumbar, cervical, thoracic, sacral and pelvic regions of a spinal column. The surgical tools of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value and all numerical values therebetween. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior." Generally, similar spatial references of different aspects or components, e.g., a "proximal end" of one component and a "proximal end" of a different component, indicate similar spatial orientation and/or positioning, i.e., that each "proximal end" is situated on or directed towards the same end of the device. Further, the use of various spatial terminology herein should not be interpreted to limit the various insertion techniques or orientations of the implant relative to the positions in the spine.

As used in the specification and including the appended claims, "treating" or "treatment" of a disease or condition refers to performing a procedure that may include administering one or more drugs, biologics, bone grafts (including allograft, autograft, xenograft, for example) or bone-growth promoting materials to a patient (human, normal or otherwise or other mammal), employing implantable devices, and/or employing instruments that treat the disease, such as, for example, micro-discectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The components of disclosed embodiments described herein can be fabricated from biologically acceptable materials suitable for medical applications, including metals, synthetic polymers, ceramics and bone material and/or their composites. For example, the components of disclosed drills and bone screws, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO4 polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaprolactone and their combinations.

Various components of disclosed embodiments may be formed or constructed of material composites, including but not limited to the above-described materials, to achieve various desired characteristics such as strength, rigidity, elasticity, compliance, biomechanical performance, durability and radiolucency or imaging preference. The components of expandable spinal implant system, individually or collectively, may also be fabricated from a heterogeneous material such as a combination of two or more of the above-described materials. The components of disclosed embodiments may be monolithically formed, integrally connected or include fastening elements and/or instruments, as described herein. For example, in some embodiments components comprising PEEK and/or titanium structures with radiolucent markers (such as tantalum pins and/or spikes) may be selectively placed on a drill, a drill bit, or a spinal implant, for example. In various embodiments, a drill is configured to bore into an adjacent vertebrae to provide a medical practitioner with a pilot hole or passageway for placement and/or sizing information to assist a surgeon with driving a a corresponding bone screw. The components of disclosed embodiments may be formed using a variety of subtractive and additive manufacturing techniques, including, but not limited to machining, milling, extruding, molding, 3D-printing, sintering, coating, vapor deposition, and laser/beam melting. Furthermore, various components of the expandable spinal implant system may be coated or treated with a variety of additives or coatings to improve biocompatibility, bone growth promotion or other features. For example, disclosed bone screws, may be selectively coated with bone growth promoting or bone ongrowth promoting surface treatments that may include, but are not limited to: titanium coatings (solid, porous or textured), hydroxyapatite coatings, or titanium plates (solid, porous or textured).

Referring generally to FIGS. 1-12 a first embodiment of an example surgical tool, e.g., a drill 100, having a movable handle is illustrated. Referring generally to FIGS. 1-4B an example drill 100 is illustrated. FIG. 1 is a perspective view of an example drill 100, FIG. 2A is an alternate perspective view of the example drill 100, and FIG. 2B is a plan view of the example drill 100. Drill 100 may include a proximal end 100a and a distal end 100b. Drill 100 may also include a drive shaft 102, a positioning handle 104, a tip portion 106, a spring 107, a sleeve 108, a housing 110, and a movable handle mechanism 150, among other things.

Figure 2A:
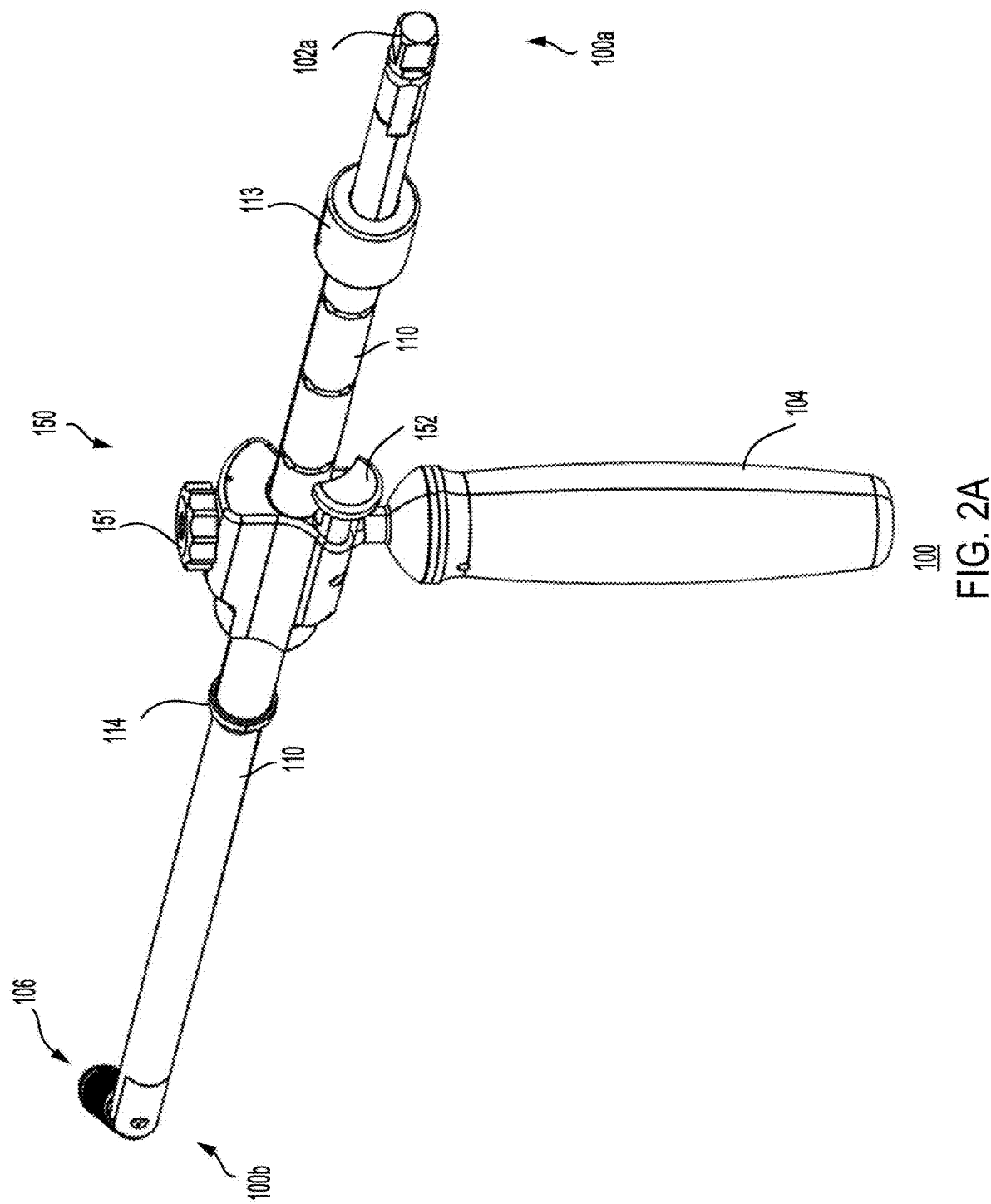
FIG. 2A is an alternate perspective view of an example drill in accordance with the principles of the present disclosure.
Figure 2B:
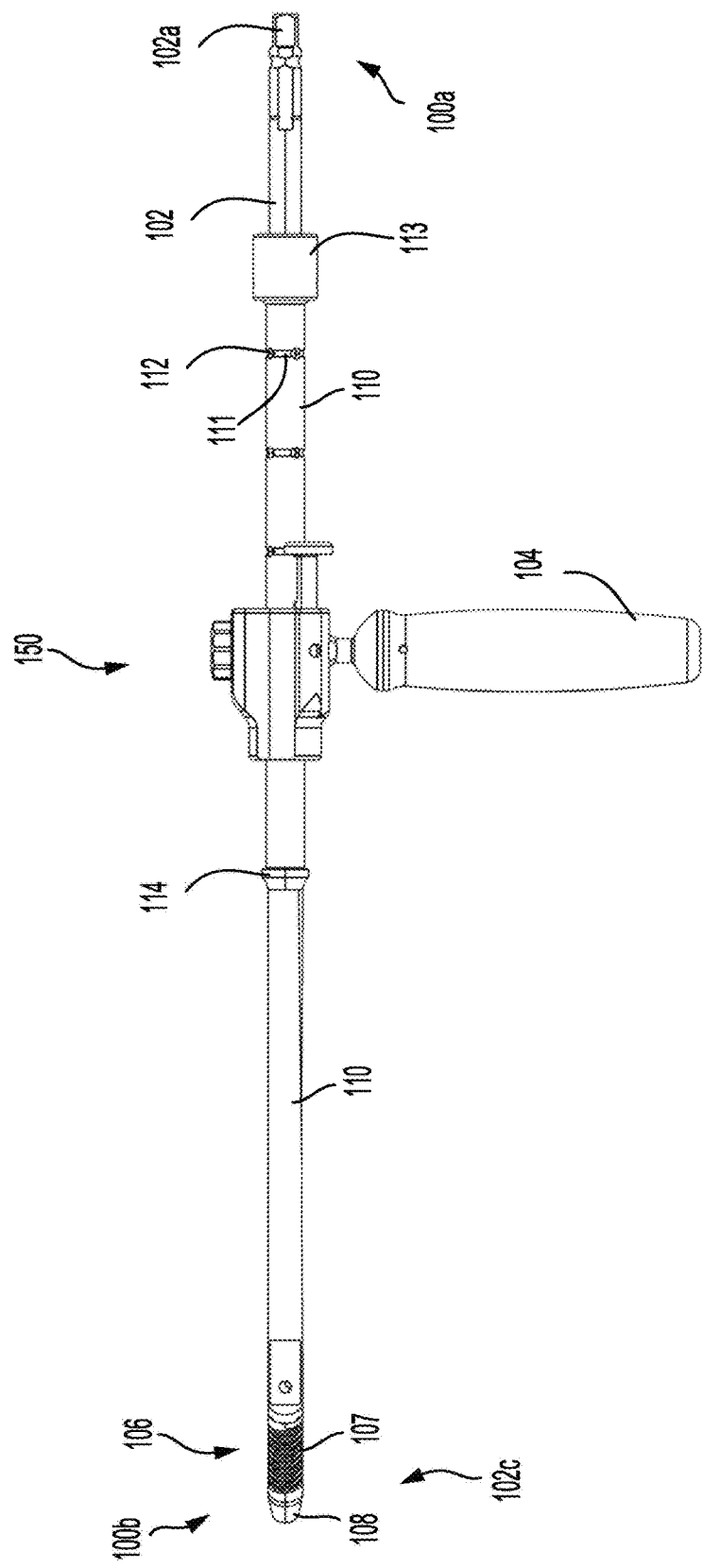
FIG. 2B is a top down view of an example drill in accordance with the principles of the present disclosure.
Figure 2C:
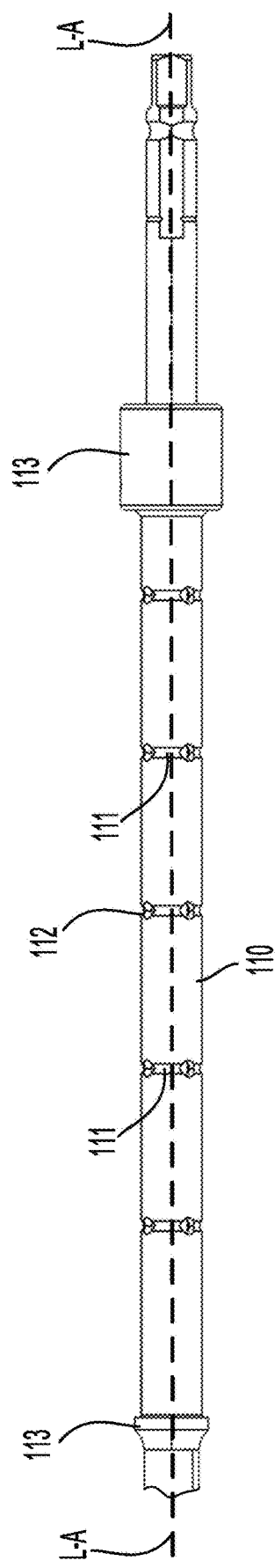
FIG. 2C is a top down view of a housing of a surgical tool in accordance with the principles of the present disclosure.
Figure 2E:
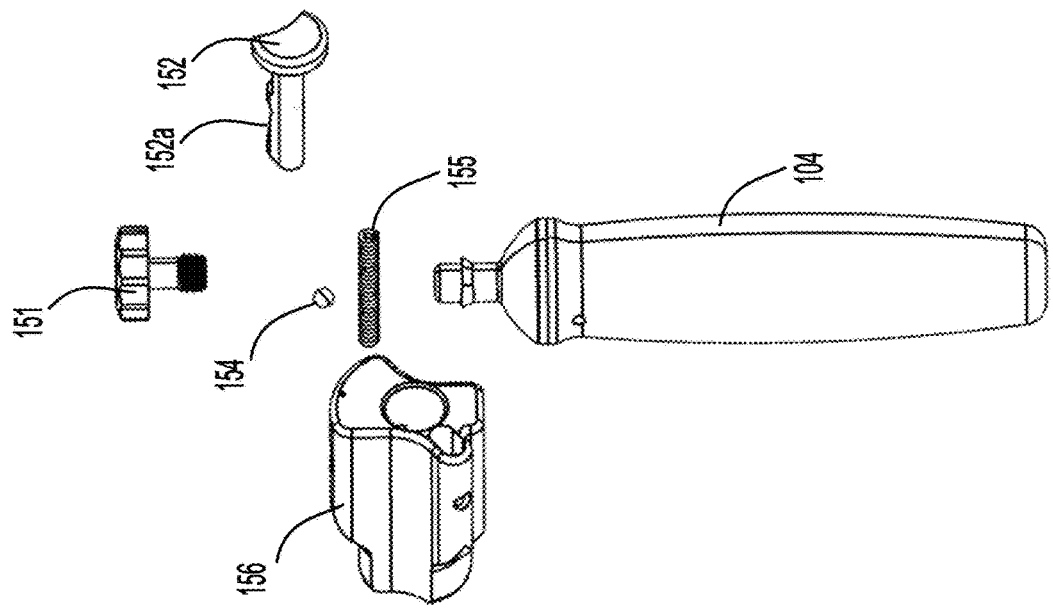
FIG. 2E is an exploded parts view of an example movable handle mechanism in accordance with the principles of the present disclosure.
Figure 2D:
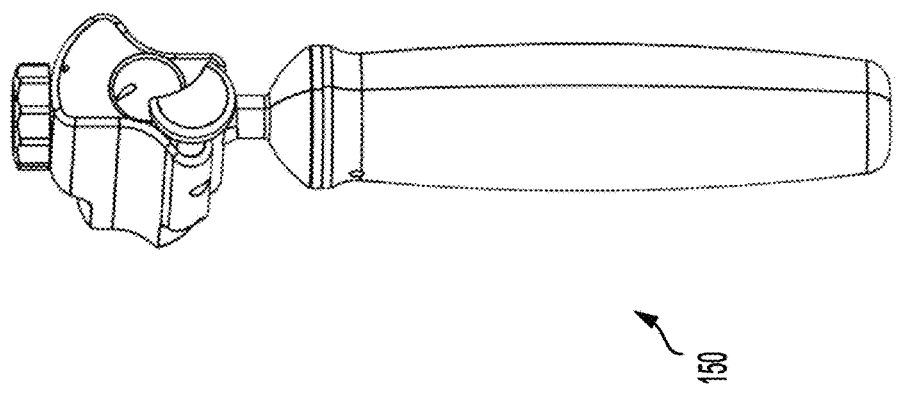
FIG. 2D is a perspective view of an example movable handle mechanism in accordance with the principles of the present disclosure.

FIG. 2C is a top down view of a housing 110 of a surgical tool, FIG. 2D is a perspective view of an example movable handle mechanism 150, and FIG. 2E is an exploded parts view of an example movable handle mechanism 150. Housing 110 may define a longitudinal axis L-A and movable handle mechanism 150 may move forward and backward along housing 110 in a direction parallel to longitudinal axis L-A. Additionally, movable handle mechanism 150 may rotate around housing 110 and/or the longitudinal axis defined by housing 110, for example. In various embodiments, movable handle mechanism 150 may move forward and backward in a longitudinal direction along the housing 110 between a proximal stop ring 113 and a distal stop ring 114, for example Movable handle mechanism 150 may also be rotatable about housing 110, for example. In various embodiments, movable handle mechanism 150 may freely move forward and backward along housing 110 in a longitudinal direction and be securely coupled to housing 110 at any one channel 111 of a plurality of channels 111.

In the illustrated embodiment, five channels 111 are shown although there may be more or less depending on the particular embodiment Channels 111 may be spaced apart at any appropriate distance and need not be symmetrically spaced, for example. In at least one embodiment, channels 111 are symmetrically distributed between stop rings 113, 114 at a distance of about 25 mm, for example. Additionally, in various embodiments, movable handle mechanism 150 may freely rotate clockwise and/or counterclockwise around housing 110 and be securely coupled to housing 110 at any one detent 112 of a plurality of detents 112, for example. In the illustrated embodiment, each channel 111 includes a plurality of symmetrically spaced and radially disposed detents 112 around the circumferential surface of housing 110, for example. In various embodiments, there may be about 2-8 detents 112, 4-6 detents 112, and more particularly about 6 detents 112.

FIG. 2D illustrates an example movable handle mechanism 150 for use with a multitude of surgical tools, for example. FIG. 2E illustrates example components of movable handle mechanism 150. Movable handle mechanism 150 may include a body portion 156 including a longitudinally extending aperture therein which housing 110 may extend through, for example. In turn, positioning handle 104 may be coupled to body portion 156 at an underside thereof. Body portion 156 may include a cavity for receiving actuator 152, for example. Actuator 152 may be referred to as a positioning actuator and take various forms. In the illustrated embodiment, actuator 152 comprises a spring loaded push button, for example. In operation, an end user may depress actuator 152 and thereby unseat positioning ball 154 from a corresponding detent 112. After releasing actuator 152 spring 155 may bias positioning ball 154 against housing 110 to seat positioning ball 154 in any one of the plurality of detents 112, for example. In various embodiments, actuator 152 includes ramped surfaces 152a which facilitate seating positioning ball 154 as explained above.

Movable handle may also include at least one locking actuator configured to securely and rigidly couple movable handle mechanism 150 to housing 110, for example. In the illustrated embodiment, locking actuator 151 comprises a rotatable knob configured to frictionally engage housing 110 by moving forward and backward in a direction substantially perpendicular to the longitudinal axis, for example. In various embodiments (not illustrated), locking actuator 151 may include a tip portion that may be seated within a corresponding detent 112 and/or channel 111, for example. The tip portion may have a size and shape generally corresponding to a size and shape of a corresponding detent 112 and/or channel 111, for example. Consistent with the disclosure herein, the movable handle mechanism 150 may be securely positioned at various locations forward and backward along housing 110 in a longitudinal direction and rotate clockwise and counterclockwise about the housing 110. At least one advantage of this configuration is that an end user may position the positioning handle 104 in a location to absorb and/or counter the torque generated at the angled tip portion 106. For example, the positioning handle can be located at a depth and a rotational position counter to the axis of rotation of the driver to enable the end user the ability to effectively resist the torque generated at the angle tip portion 106 and prevent "walking."

Drive shaft 102 may be configured to connect and disconnect with various types of drivers including manually operated handles and mechanically powered drive means that may be of a ratcheting or non-ratcheting type and which will be discussed in further detail below (see, e.g., FIGS. 10-11). For example, drive shaft 102 may include a drive end 102a and a main drive shaft portion 102b extending in a longitudinal direction through a housing 110. Drive end 102a may comprise a variety of drive interfaces for coupling and uncoupling with various manually operated ratcheting handles and powered drivers, for example Drive shaft 102 may freely rotate inside of housing 110 to transfer rotational force applied at the drive end 102a at proximal end 100a to drive end 102c at distal end 100b, for example. Positioning handle 104 may be securely held in place while drive shaft 102 freely rotates within housing 110. Positioning handle 104 may be configured to assist with maintaining and controlling the drill 100, e.g., in view of torque transmitted through drive shaft and the corresponding resultant return forces. At least one advantage of having positioning handle 104 coupled to a movable handle mechanism 150 is that a surgeon may have greater freedom in movement and control maintaining drill 100 in a desired position while drilling a passageway (e.g., a pilot hole) for a bone screw 300. For example, when drilling a passageway for a bone screw into the anatomy of a patient a return force may apply a rotational force against the drill 100 and a surgeon may be able to maintain the drill 100 in the desired position, for example Additionally, in being able to move positioning handle 104 via movable handle mechanism 150 and drill 100 may be utilized for performing a wide variety of surgeries and also accounting for a greater variability in body types and ergonomic preferences of end users, for example.

Figure 3:
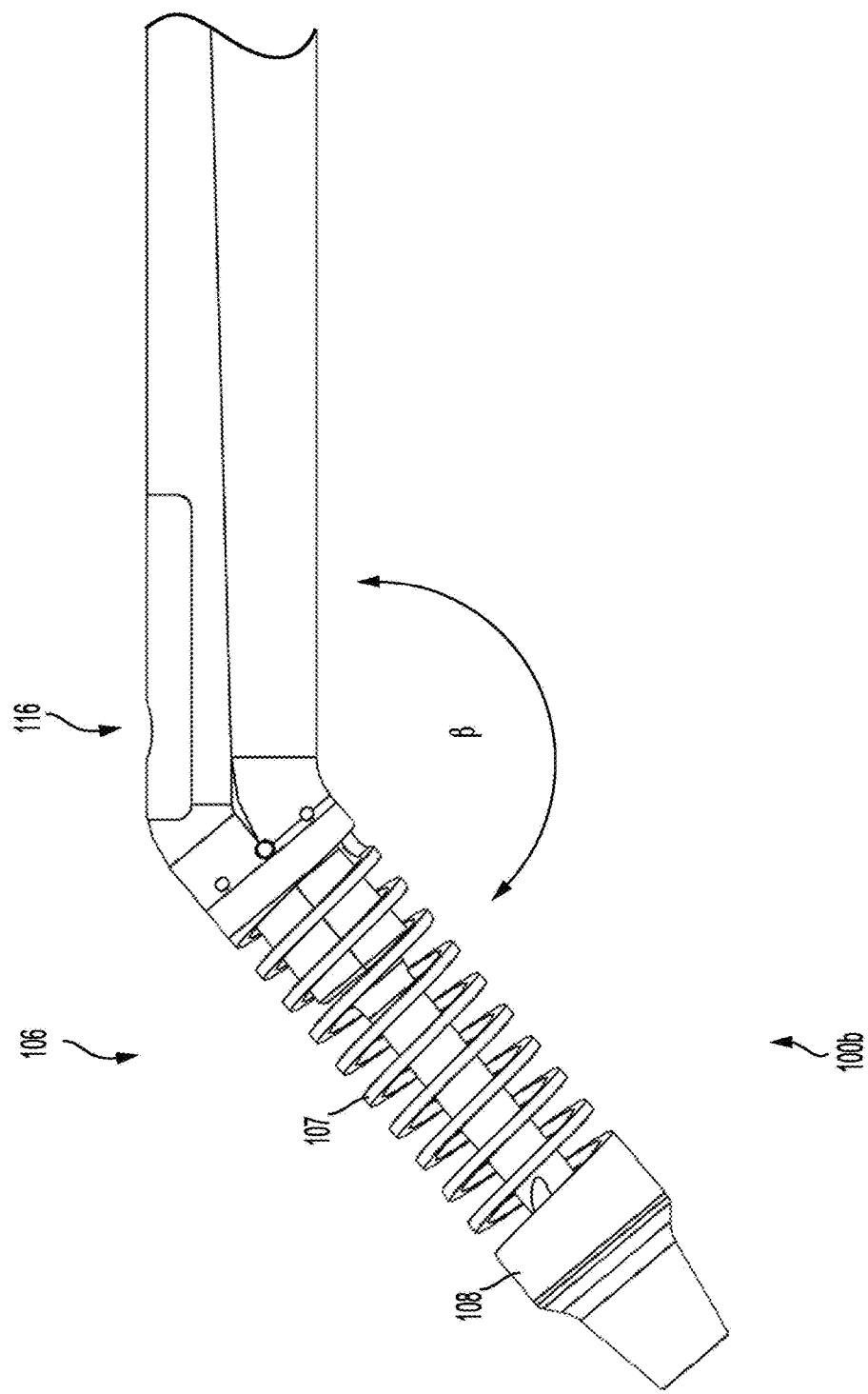
FIG. 3 is a magnified view of the tip portion of an example drill in accordance with the principles of the present disclosure.

FIG. 3 is a magnified view of the tip portion 106 of an example drill 100 in accordance with the principles of the present disclosure. Tip portion 106 may be angled at a degree β (Beta) with respect to a longitudinal direction of housing 110 and/or drive shaft 102. In various embodiments, tip portion 106 may extend in a direction that defines a drilling axis (rotation axis) of drill bit 109. In some embodiments, tip portion 106 is angled such that the degree β corresponds to the ultimate desired angle of a passageway for receiving a bone screw 300. In some embodiments, the degree β corresponds to an inclination of a bone screw aperture 1001 of a medical plate or medical device, e.g., medical device 1000 is a spinal implant including at least one bone screw aperture 1001 (see FIG. 23). In various embodiments, the tip portion 106 is angled to facilitate drilling of a passageway through a void space of a bone screw aperture 1001 of a spinal implant from a posterior approach while a patient is lying in a prone position, for example. Other surgical approaches, such as anterior, lateral, and/or posterior lateral approaches are also contemplated and may comprise adjustments to the degree β (Beta).

In various embodiments, tip portion 106 may be inclined about 20°-60°, more particularly about 30°-50°, and even more particularly about 40°-45°, with respect to a longitudinal direction of housing 110. However, it shall be understood that tip portion 106 may be angled at any degree β Similarly, bone screw apertures 1001 may be angled at any degree with respect to endplates 1010, 1020 and tip portion 106 may be angled at a corresponding degree β to facilitate the installation of bone screw 300 therein (see FIG. 14). This angled arrangement may be advantageous for driving bone screw 300 while medical device 1000 is positioned between adjacent vertebral bodies. Furthermore, this angled arrangement may be advantageous to avoid anatomical landmarks and features such as the pelvic ring, rib cage, and iliac crest, of a patient, for example.

FIGS. 4A and 4B illustrate an example drill 100 that may include a flushing hole 116 having a flushing path to clean, lubricate, and/or inspect the components of tip portion 106. For example, as shown in FIG. 4A a flushing hole 116 is shown, and in FIG. 4B a cover 116a is removed to illustrate the flushing path. Flushing hole 116 may be advantageous for cleaning the interior orifices of tip portion 106. Also shown in FIG. 4A is sleeve 108 which is a protective sleeve having a conical shape that surrounds drill bit 109. For example, sleeve 108 may cover or surround drill bit 109 such that adjacent patient tissue is protected from drill bit 109.

Sleeve 108 may be composed of elastomeric materials, thermoplastic materials, metallic materials, and various combinations thereof. In one embodiment, sleeve 108 is composed of an elastomeric material to provide flexibility and a high coefficient of friction for engaging and/or being seated within a bone screw aperture 1001, for example. In an alternate embodiment, sleeve 108 is composed of metallic material, e.g., stainless steel and/or titanium. In another embodiment, sleeve 108 is composed of thermoplastic material, e.g., Polyether ether ketone (PEEK) and/or other organic thermoplastic polymers in, e.g., the polyaryletherketone (PAEK) family. In another embodiment, sleeve 108 is composed of polyphenylsulfone (PPSU), also referred to as Radel by those with skill in the art. In another embodiment, sleeve 108 is composed of various combinations of the above enumerated materials. However, it shall be understood that the above enumerated materials are examples, and they shall not be construed as limiting.

Figure 5:
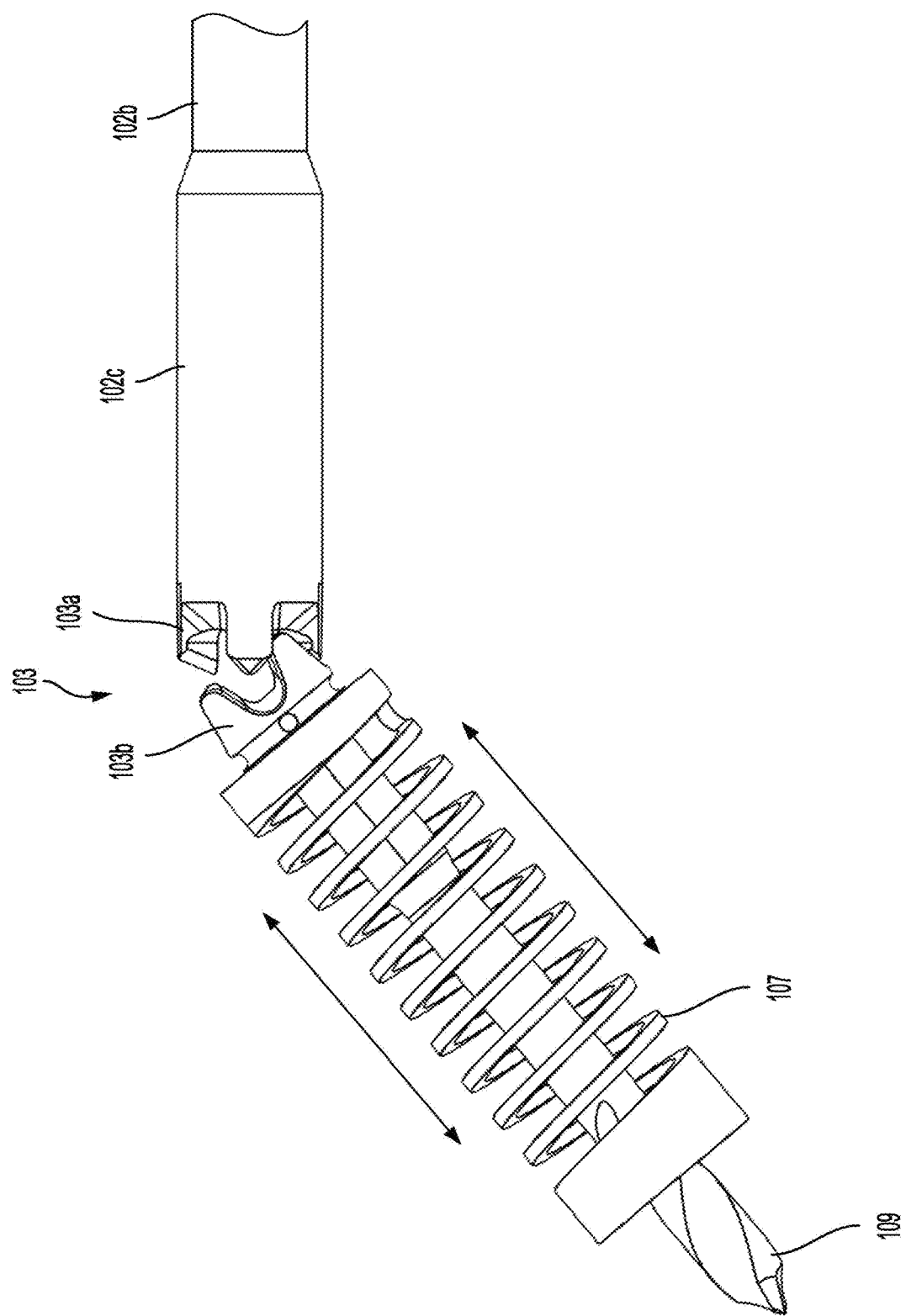
FIG. 5 is a side view of a gear mechanism in accordance with the principles of the present disclosure.

Referring generally to FIGS. 5-6B, operative characteristics of an example drill 100 will be explained. FIG. 5 illustrates a tip portion 106 (also referred to as an angled tip region) with a sleeve 108 and housing 110 removed for ease of explanation. In FIG. 5, it is shown that a spring 107 generally surrounds drill bit 109. Spring 107 may be a compressible spring, a helical spring, a coil spring, of the like. In at least one embodiment, spring 107 takes the form of a compressible material such as rubber or foam. In some embodiments, spring 107 is covered by a protective cover to prevent debris and other foreign matter from entering in between the coils. In operation, a surgeon may press a proximal most end of sleeve 108 within a bone screw aperture 1001, or alternatively against a surface to be drilled. In doing so, spring 107 may compress (shown by double sided arrows) and drill bit 109 may extend out of sleeve 108 (beyond sleeve 108). For example, drill bit 109 is rigidly secured to drill 100 and sleeve 108 and spring 107 are movable with respect to drill bit 109. At least one advantage of this arrangement, is that drill bit 109 may be protected and/or covered by sleeve 108 while drill bit 109 advances into a surface to be drilled and/or through bone screw aperture 1001. For example, lateral sidewall surfaces of drill bit 109 are continuously protected from adjacent structures such as tissue while drill bit 109 continues to advance through sleeve 108 and into a boney structure.

Consistent with the disclosure herein, drill 100 may be understood as operating in various modes of operation. For example, a protected mode of operation and a drilling mode of operation. For example still, in a first mode of operation where the spring 107 is in a neutral position (non-compressed position) the sleeve 108 and spring 107 cover and/or surround the lateral sidewalls of the drill bit 109, for example. In a second mode of operation where the spring 107 is in a compressed or partially compressed position due to the sleeve 108 acting against a bearing or retaining surface, the spring 107 may be compressed in a direction parallel to an extension direction of drill bit 109, for example. The extension direction of drill bit 109 may be coincident with a rotation axis of the drill bit 109 (drilling axis). Accordingly, in the second mode of operation, and due to the compression of spring 107, drill bit 109 may move through the sleeve 108 thereby exposing a tip of the drill bit 109 for drilling, for example Additionally, in various embodiments and in the first mode of operation, the sleeve 108 and compressible spring 107 completely surround the lateral sidewalls of the drill bit 109. Furthermore, in various embodiments, and in the first mode of operation, a distal most end of the sleeve 108 extends distally farther than a distal most end of the drill bit 109.

Also as shown in FIGS. 6-6*b*, an example gear mechanism 103 may be provided. Gear mechanism 103 may include worm gears, beveled gears, miter gears, planetary gears, sliding gears, helical or spiral gears, gear coupling parts, pawls, having teeth of various sizing and shapes for directing a rotation of the drive shaft 102 to drive end 102*c*. For example, applying a rotation force at drive end 102*a* may apply an equal or substantially equal rotation force at drill bit 109 because the gear mechanism 103 may redirect the rotation force. As illustrated, gear mechanism 103 may include a first body portion supporting a group of teeth 103*a* that are meshed with a second group of teeth 103*b* supported by a second body portion. In the example embodiment, the first group of teeth 103*a* includes fourth teeth and the second group of teeth 103*b* includes four teeth although the total number of teeth may be more or less. Those with skill in the art will readily appreciate that the particular geometry and number of teeth 103*a*, 103*b* may be modified to accommodate any particular angle β (see FIG. 3). Additionally, in some embodiments, gear mechanism 103 may be designed to provide a mechanical advantage, such increasing or lowering the speed of rotation. For example, when a ratio of teeth sizing of teeth 103*a*, 103*b* is inferior or superior with respect to the other.

Figure 7:
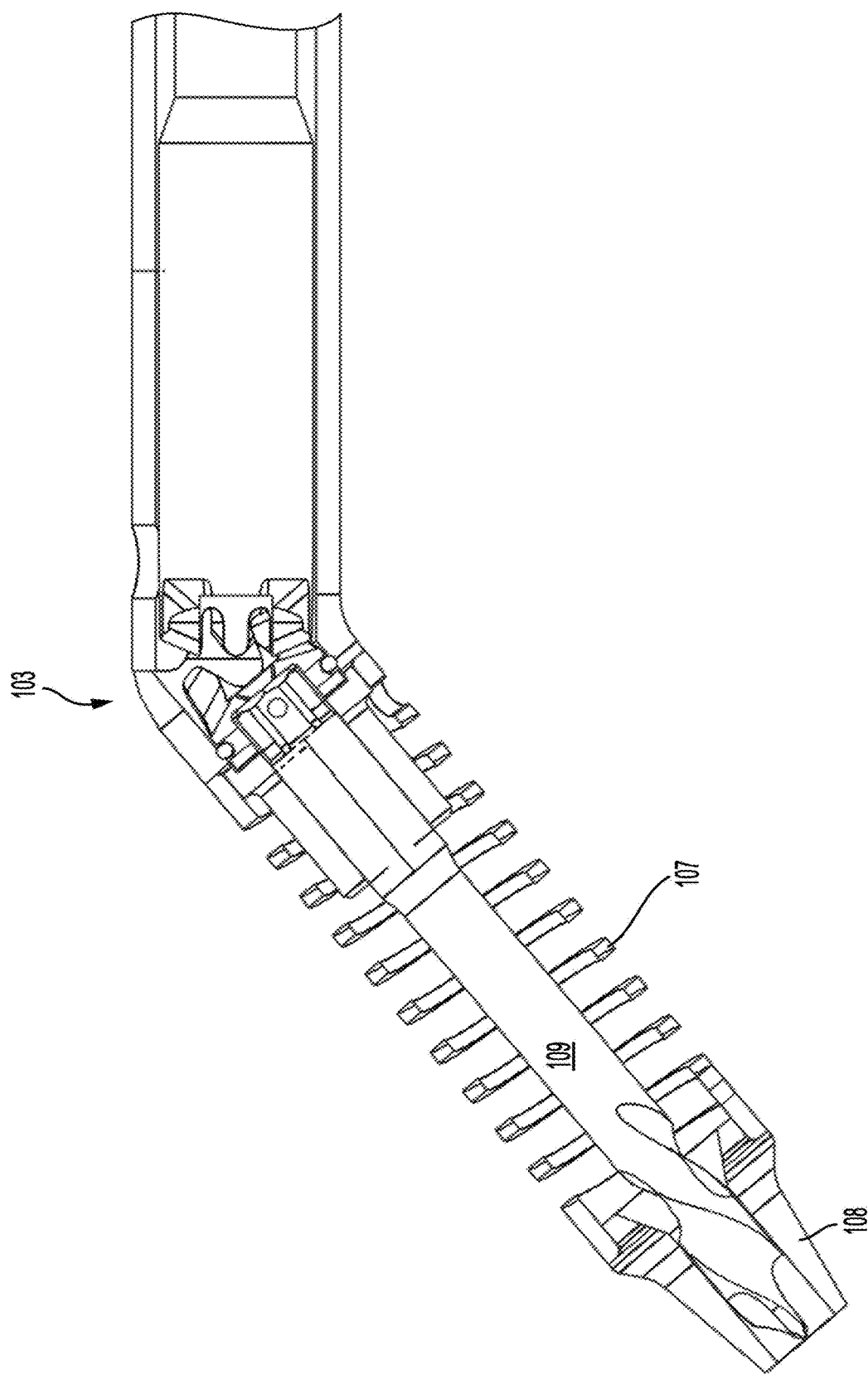
FIG. 7 is a cross sectional view of a gear mechanism in accordance with the principles of the present disclosure.
Figure 8:
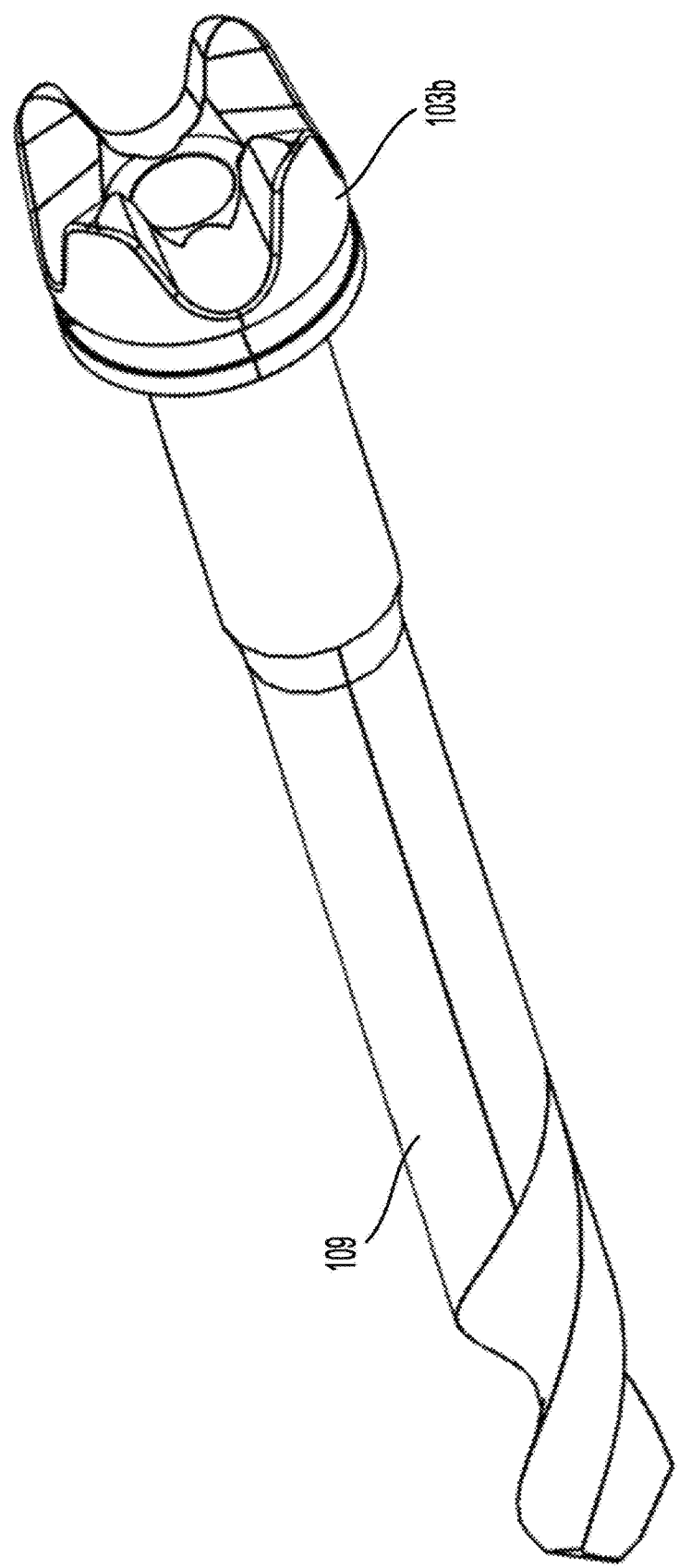
FIG. 8 is a perspective view of a portion of a gear mechanism and a drill bit in accordance with the principles of the present disclosure.
Figure 9:
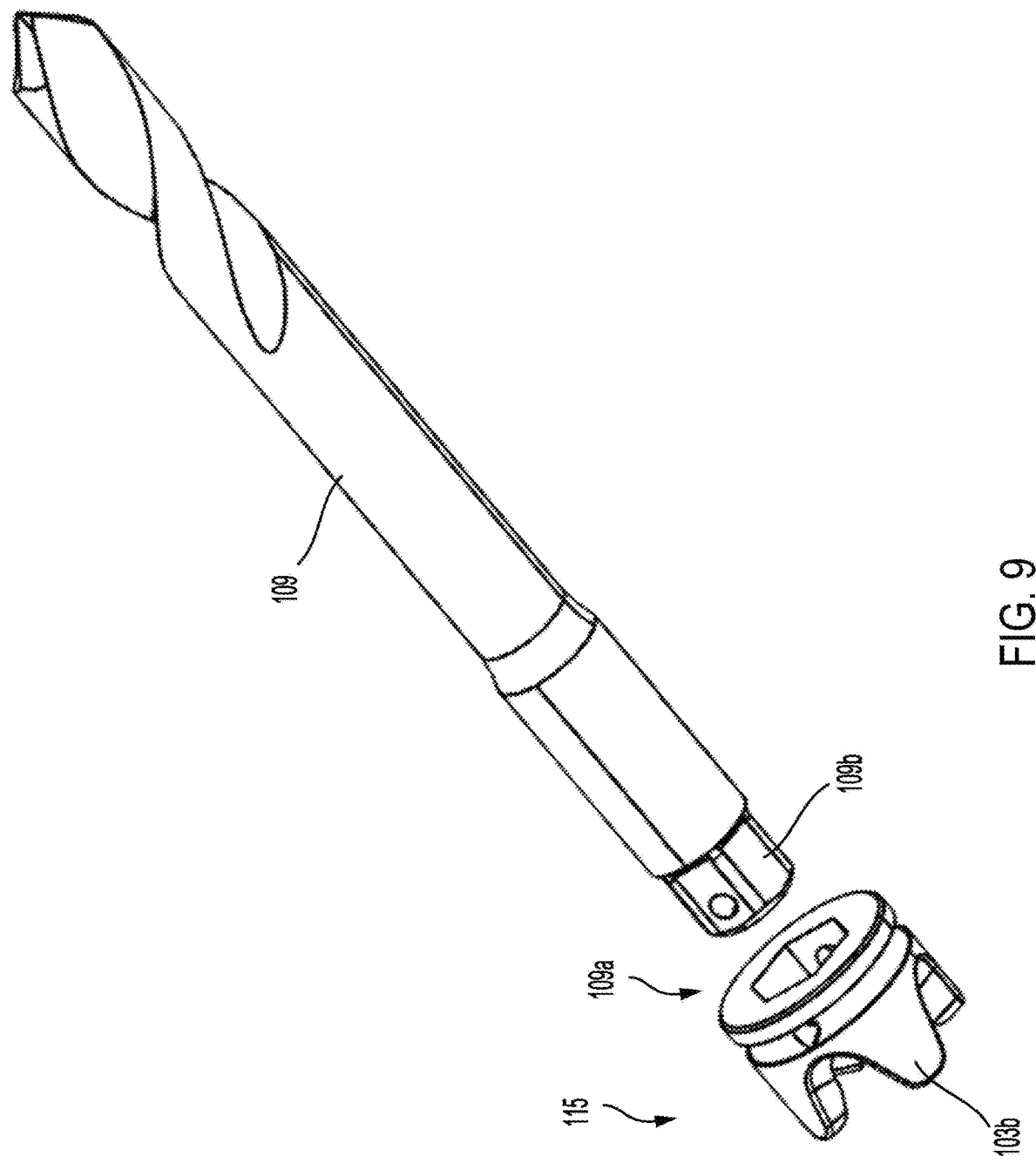
FIG. 9 is a perspective view of a portion of a gear mechanism and an aperture for receiving a drill bit in accordance with the principles of the present disclosure.

As illustrated in FIG. 7, a cross sectional view of spring 107, sleeve 108, drill bit 109, and gear mechanism 103 is illustrated. In the cross sectional view, it is shown how drill bit 109 may rotate due to teeth 103*a* being meshed with teeth 103*b* while also being protected by spring 107 and sleeve 108. As illustrated in FIG. 8, drill bit 109 may be coupled to an opposite side of the second body portion supporting teeth 103*b*, for example. As illustrated in FIG. 9, a drill bit coupler 115 may comprise the second body portion and may include a drill bit aperture 109*a* configured to receive a coupling end 109*b* of drill bit 109 on one end and teeth 103*b* on an opposite end. In some embodiments, the drill bit coupler 115 may include an extension shaft (not illustrated). The drill bit aperture 109*a* and coupling end 109*b* of drill bit 109 may correspond in size and shape to one another. For example, drill bit aperture 109*a* and coupling end 109*b* may have a hex, hexalobular, square, star, torx, prismoidal, polygonal, etc. shape dimensioned such that coupling end 109*b* may be seated firmly within drill bit aperture 109*a*.

In an alternate embodiment, drill 100 may include a joint mechanism in lieu of gear mechanism 103 (not illustrated). For example, although not illustrated herein, the parent application from which this application is a continuation in part of, illustrates a joint mechanism 105 that may be substituted with gear mechanism 103. For example, U.S. patent application Ser. No. 17/123,906, discloses a joint mechanism 105 at FIG. 17 that may be operable/drivable via drive shaft 102 in the same, similar, or substantially the same way as gear mechanism 103 as explained above. The disclosure of U.S. patent application Ser. No. 17/123,906 is incorporated herein in its entirety.

In an alternate embodiment, drill 100 may include a flexible shaft that may bend through the angled tip region in lieu of gear mechanism 103 and/or the joint mechanism as described above. For example, a flexible shaft mechanism may extend from the proximal end 100*a* to the angled tip region 106 where a drill bit 109 may be coupled to a distal end of the flexible shaft. For example still, the flexible shaft mechanism may comprise a first drive end 102*a* and a second drive end 102*b* comprising a drill bit coupler 115 or the like.

The described flexible shaft mechanism can be formed of an elastomeric and/or metallic material for example. In embodiments including metallic materials the flexible shaft mechanism may comprise an undulating pattern of transverse cuts or seams across the width of the flexible shaft mechanism that form flexible indentations enabling the flexibility of the described flexible shaft. For example, an undulating dove tail pattern, c-shaped pattern, webbed pattern, etc. For example still, the flexible shaft may be formed with a plurality of successive and organized cuts making the shaft flexible laterally although still strong in tension and sufficient to apply rotational forces to drill bit 109 similarly as explained herein. In at least one embodiment, the flexible shaft mechanism can be made of an assembly of springs. Additionally, the flexible shaft mechanism may extend longitudinally through housing 110 of drill 100 until a region approximately corresponding with drill bit coupler 115 and may include a drill bit coupler 115 and/or a similar aperture for receiving a drill bit 109 such as aperture 109*a*, for example.

Figure 10:
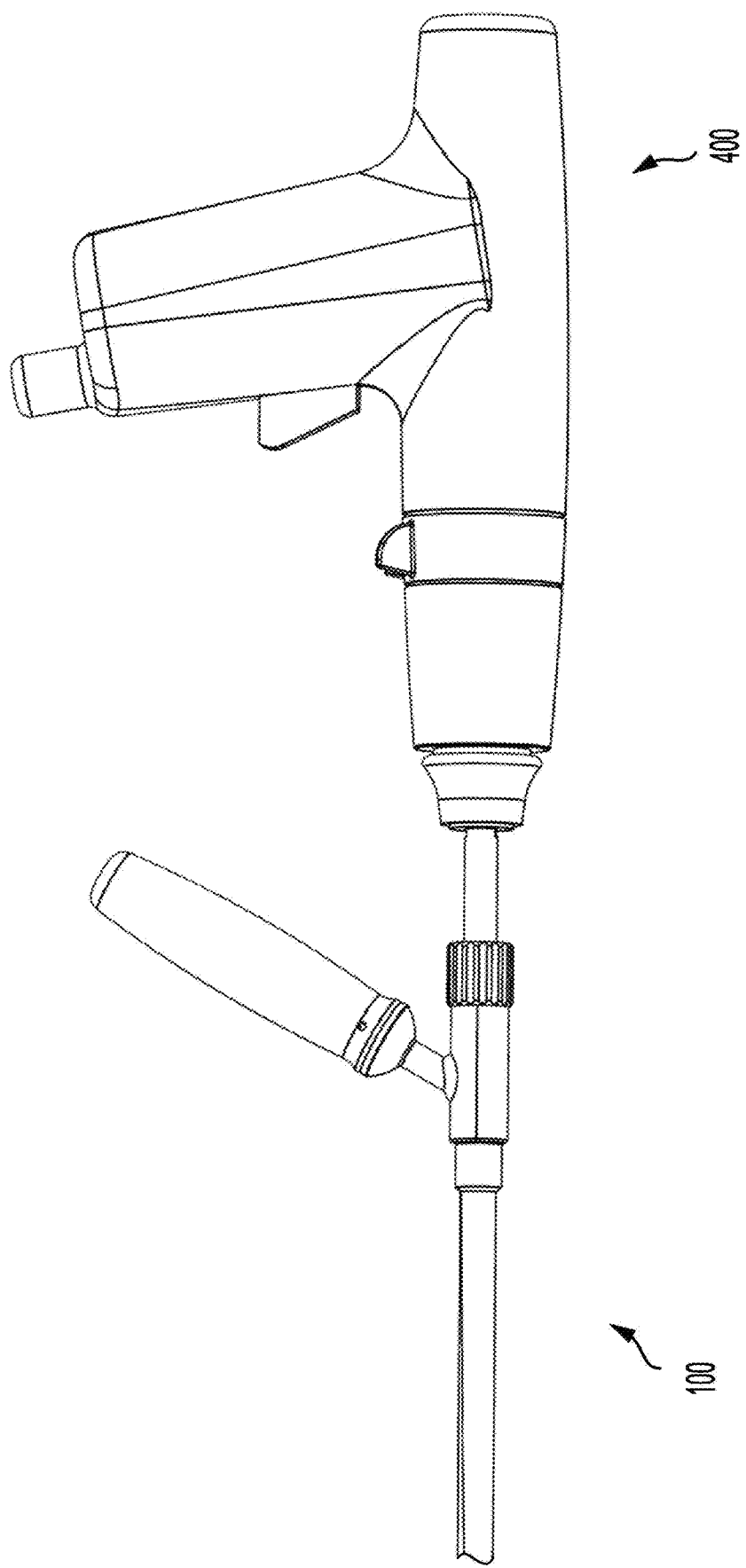
FIG. 10 is a side view of an example drill coupled to a powered driver in accordance with the principles of the present disclosure.

FIG. 10 illustrates an example drill 100 operably coupled to a powered driver 400 in accordance with the principles of the present disclosure. Powered driver 400 may be powered by any means, e.g., electrically operated or pneumatically operated. At least one example powered drill is the POWEREASE™ System sold by Medtronic and/or the powered rotary-type handpiece described in U.S. Pat. No. 10,456,122, which is incorporated herein by reference in its entirety.

Figure 11:
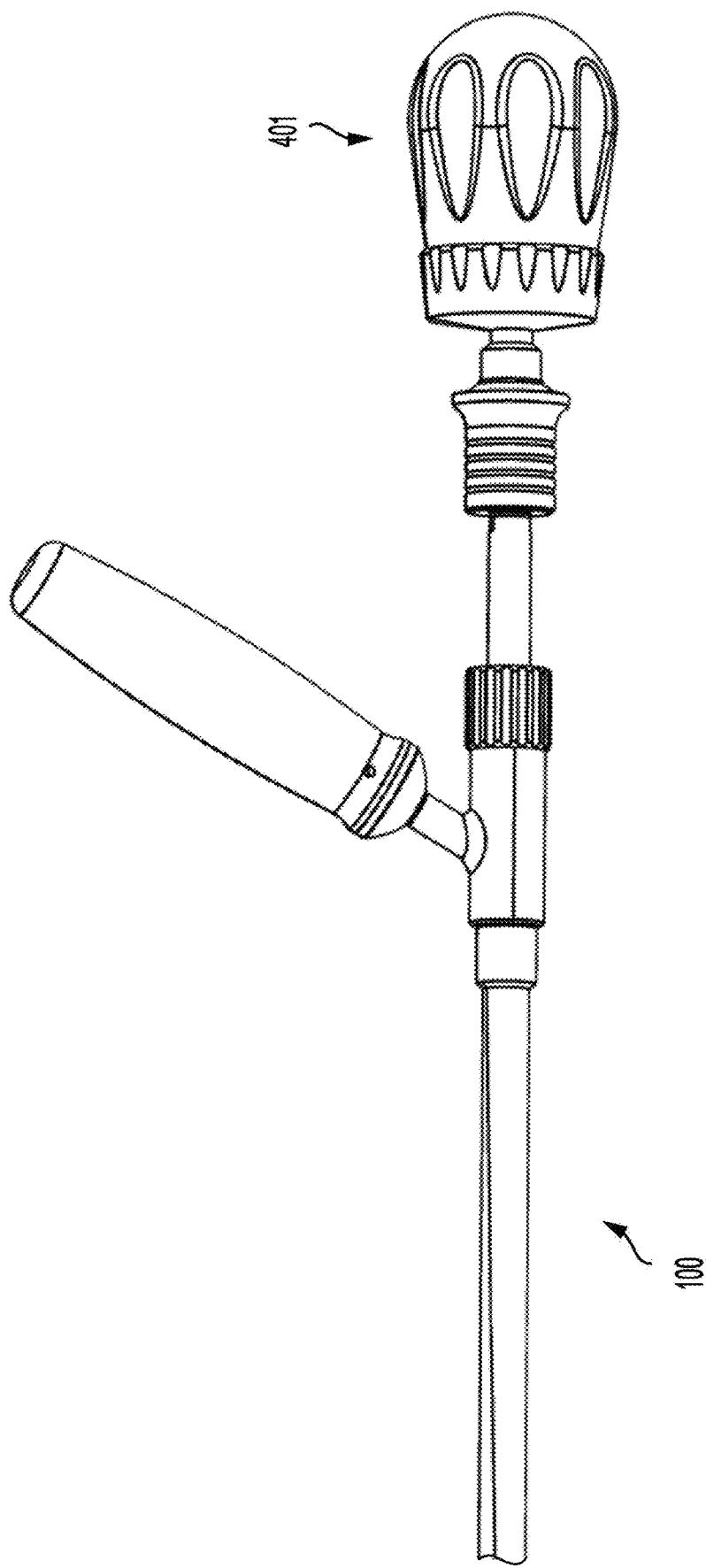
FIG. 11 is a side view of an example drill coupled to a manual hand driver in accordance with the principles of the present disclosure.

FIG. 11 illustrates an example drill 100 operably coupled to a manual hand driver 401 in accordance with the principles of the present disclosure. Hand driver 401 may selectively couple and uncouple with drive end 102*a* of drive shaft 102. At least one example of a manual hand driver 401 may be the commercially available QC handle sold by Medtronic of Minneapolis Minn. In various surgical techniques, a manual hand driver 401 as illustrated may be advantageous for performing gentle drilling, cleaning, excavation, and/or boring of a relatively soft or damaged bone, for example.

Figure 12:
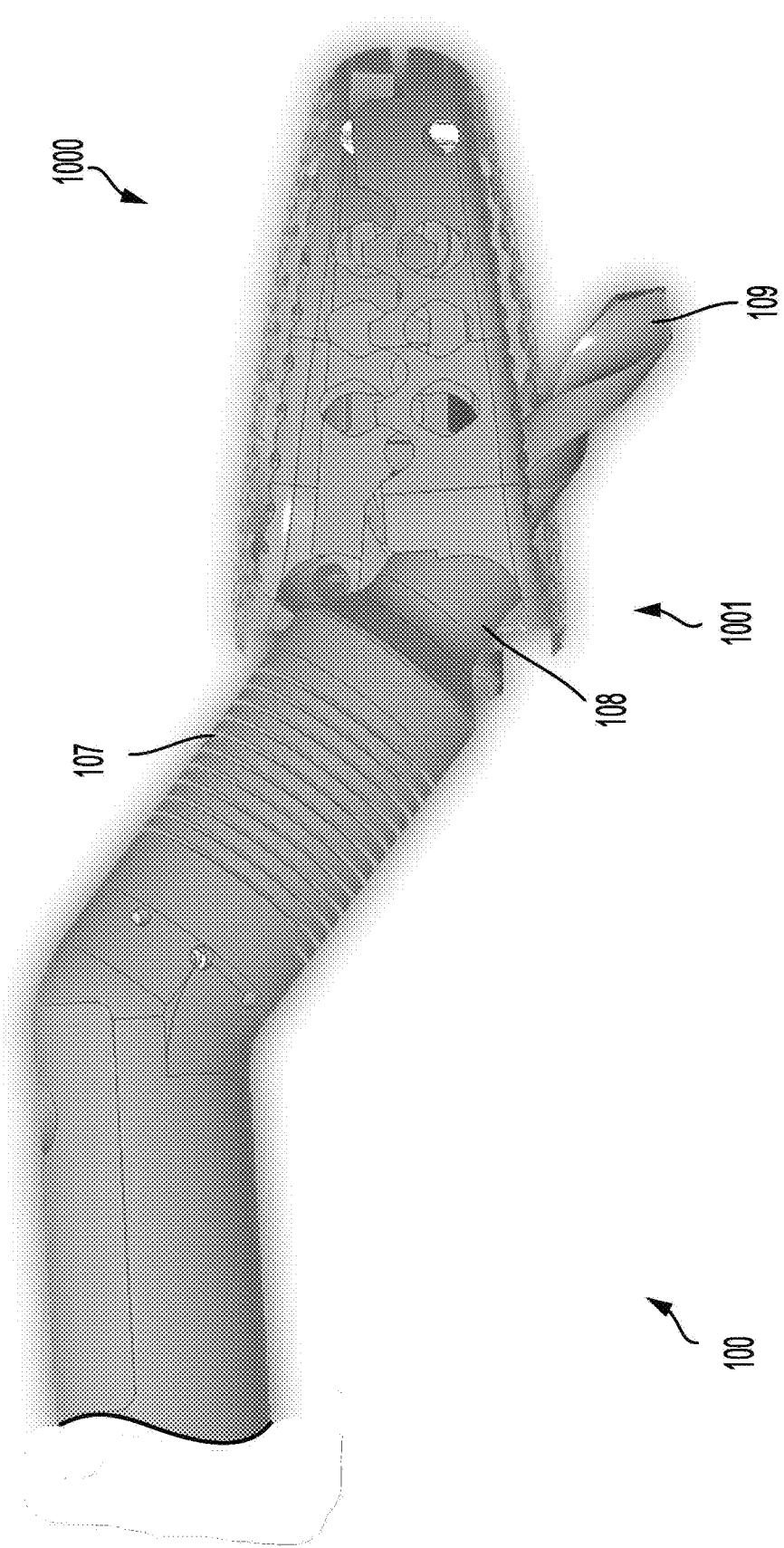
FIG. 12 is a side view of an example drill engaged with an aperture of an implant in accordance with the principles of the present disclosure.
Figure 13A:
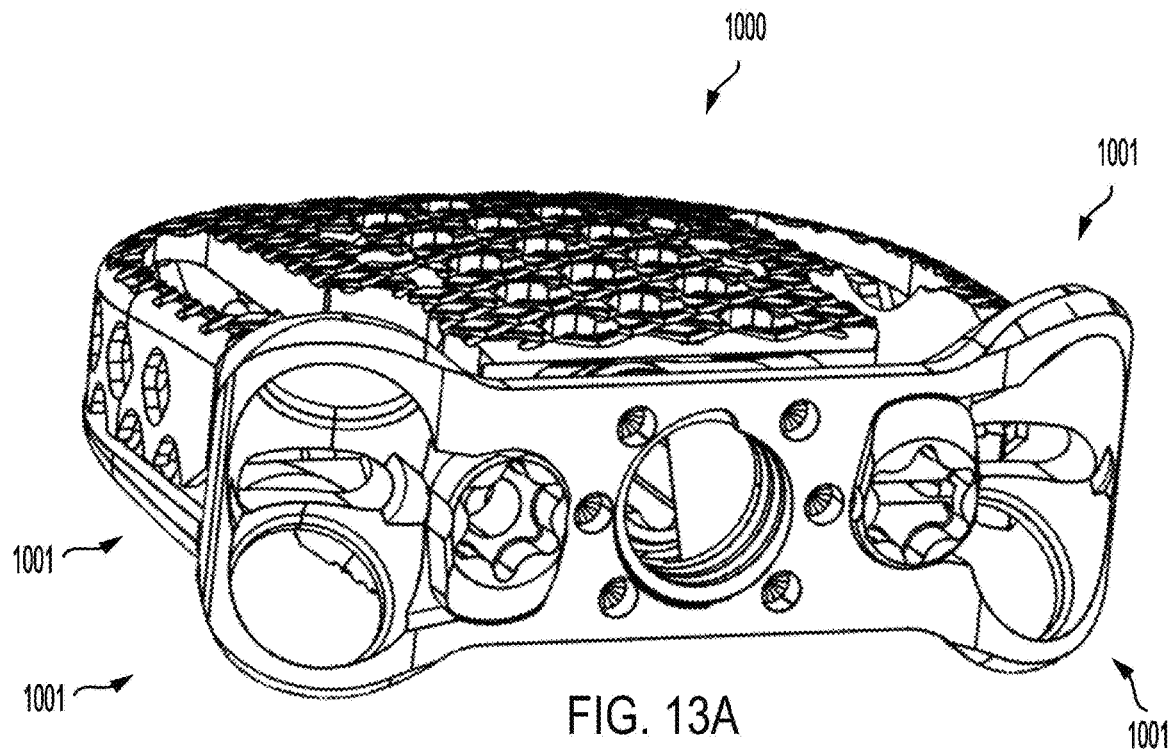
FIG. 13A is a perspective view of an example implant having conically shaped apertures for seating a tip of a drill in accordance with the principles of the present disclosure.
Figure 13B:
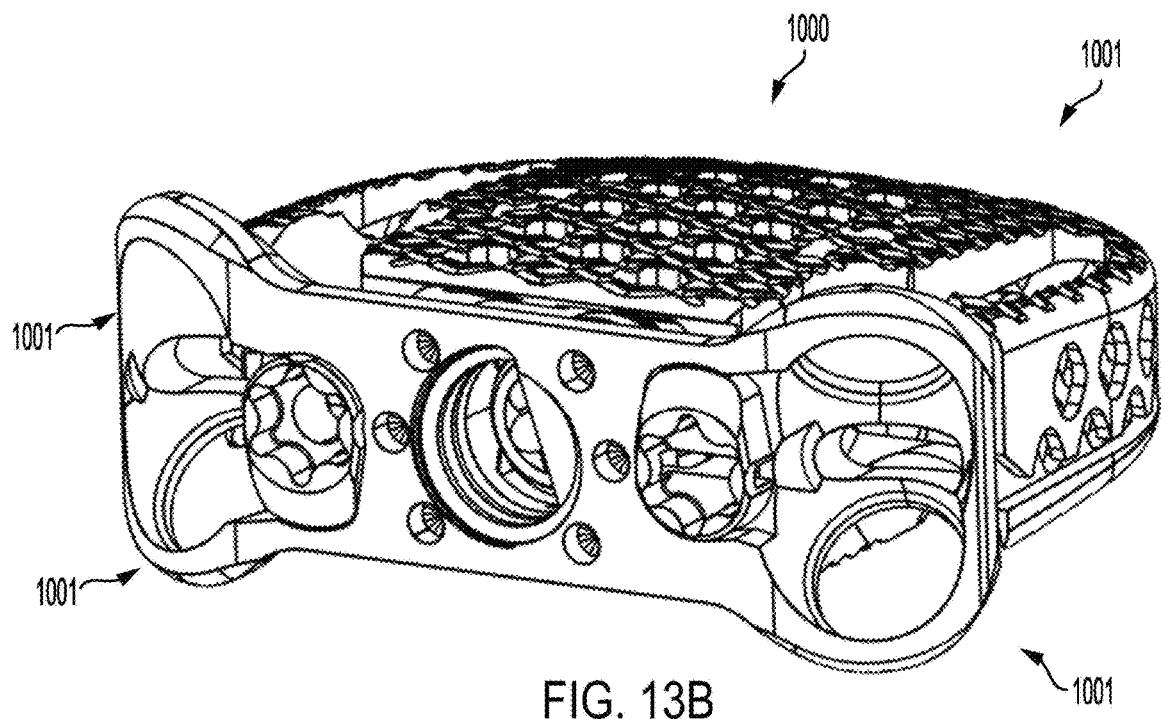
FIG. 13B is an alternate perspective view of an example implant having conically shaped apertures for seating a tip of a drill in accordance with the principles of the present disclosure.

FIG. 12 illustrates an example drill 100 seated within a bone screw aperture 1001 of an implant 1000. As illustrated, a conically shaped sleeve 108 is seated within a corresponding conically shaped bone screw aperture 1001 of implant 1000, for example. For example, bone screw aperture 1001 may taper at the same or similar extend as sleeve 108 may taper and/or bone screw aperture 1001 may have a the same, similar, or substantially the same cross sectional dimensions. Drill 100 may be firmly pressed towards implant 1000 such that spring 107 is fully compressed thereby enabling drill bit 109 to extend through bone screw aperture 1001 beyond a bottom surface of a bottom endplate of implant 1000. FIGS. 13A and 13B illustrate an alternate implant 1000 having four conically tapered bone screw apertures 1001.

Figure 14:
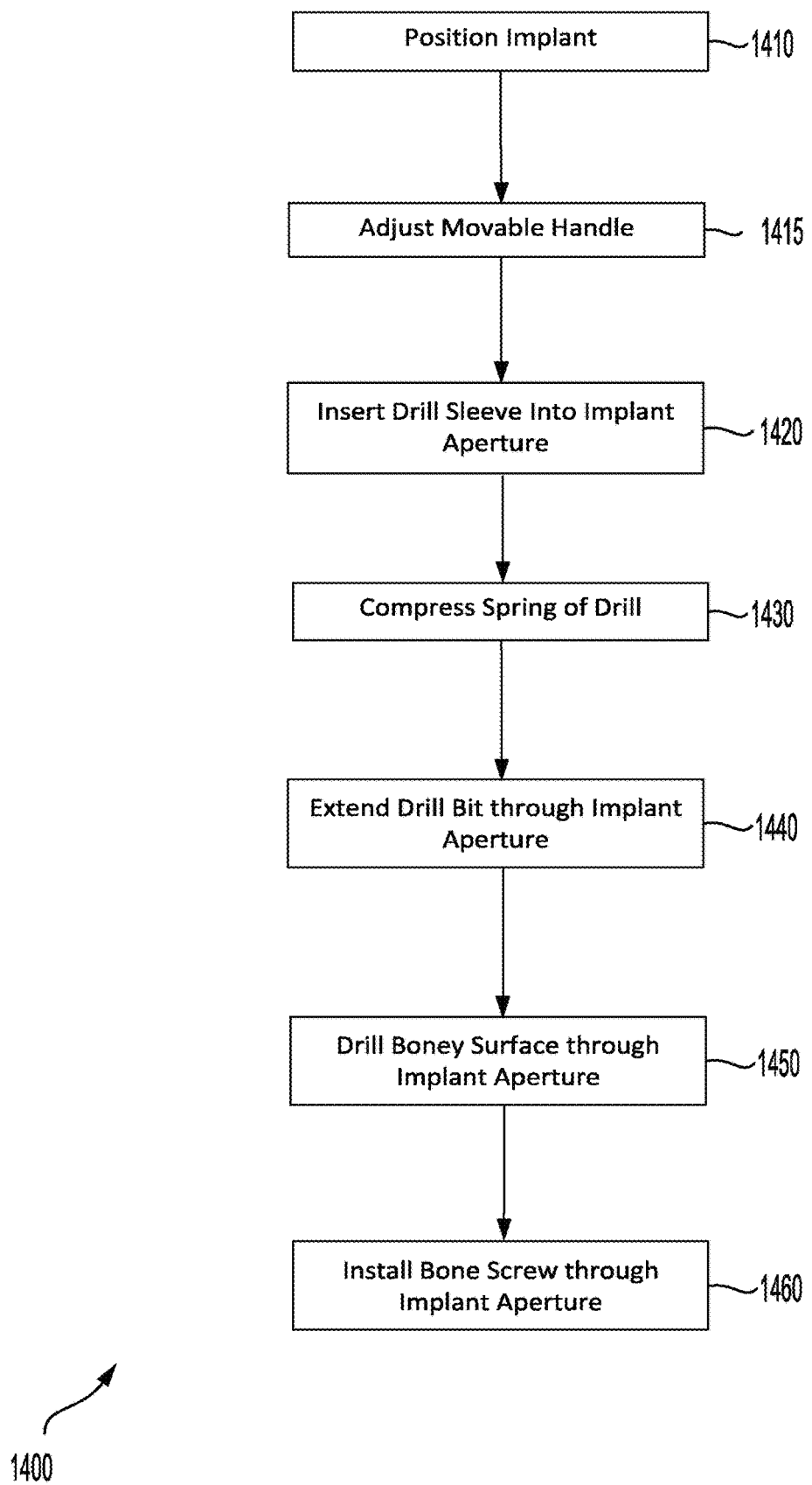
FIG. 14 is an example flow chart of a method in accordance with the principles of the present disclosure.

FIG. 14 illustrates an example method in accordance with the principles of the above disclosure. The method may be implemented with various drill 100 embodiments disclosed hereinabove, for example. In practice, at step 1410 an end user such as a surgeon may position an implant between adjacent vertebral bodies. The end user may expand the implant such that it is relatively firmly positioned between the two vertebral bodies (e.g., a superior vertebral body and an inferior vertebral body). At step 1415, the end user may adjust the movable handle longitudinally along the length of housing and/or rotationally around the housing, for example. In various embodiments, step 1415 may further comprise the substeps of (a) moving the movable handle assembly forward and/or backward in a longitudinal direction and (b) moving the movable handle assembly rotationally in a clockwise or counterclockwise direction around a longitudinally extending axis defined by the housing, for example. In various embodiments, moving the movable handle assembly forward/backward and/or clockwise/counterclockwise may further include the substep of seating a pin in a channel and/or seating a ball in a detent, for example. At step 1420, the end user may be provided with a protected drill as disclosed herein and insert a conically tapered protective sleeve portion into a bone screw aperture of the implant. At step 1430, the end user may firmly press the drill against the implant thereby compressing a protective spring of the drill. At step 1440, and due in part to the compression performed at step 1430, a drill bit may extend through the protective sleeve and through the implant aperture. Thereafter, at step 1450, the end user may operably rotate a drive shaft of the drill and begin to drill a passageway into a boney surface, for example. In some embodiments, the bone screw aperture may be angled relative to the implant and/or surfaces of the adjacent boney structure. In those embodiments, due to the conically tapered sleeve portion being seated in an angled bone screw aperture, the passageway may be drilled at an angle that corresponds to the angle of the bone screw aperture. For example, the passageway and bone screw aperture may have the same, similar, or substantially the same angle as measured with respect to the implant and/or boney surface. At step 1460, the end user may install a bone screw through the bone screw aperture and into the previously drilled passageway at a predefined angle. Furthermore, at step 1460 an end user may, for example, utilize the screwdriver 200 and coordinating bone screws as further described below.

Figure 15:
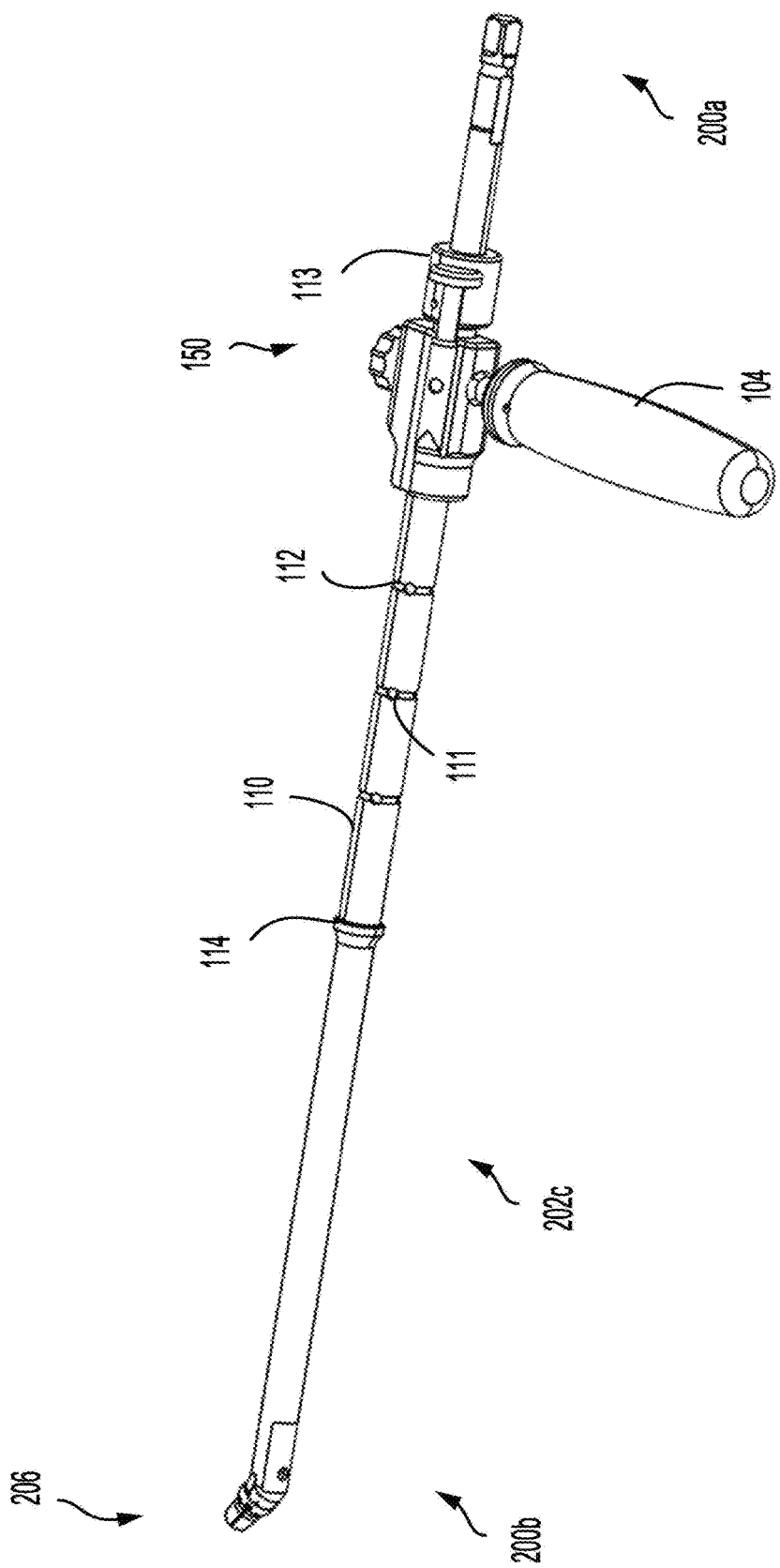
FIG. 15 is a perspective view of an example screwdriver in accordance with the principles of the present disclosure.
Figure 16:
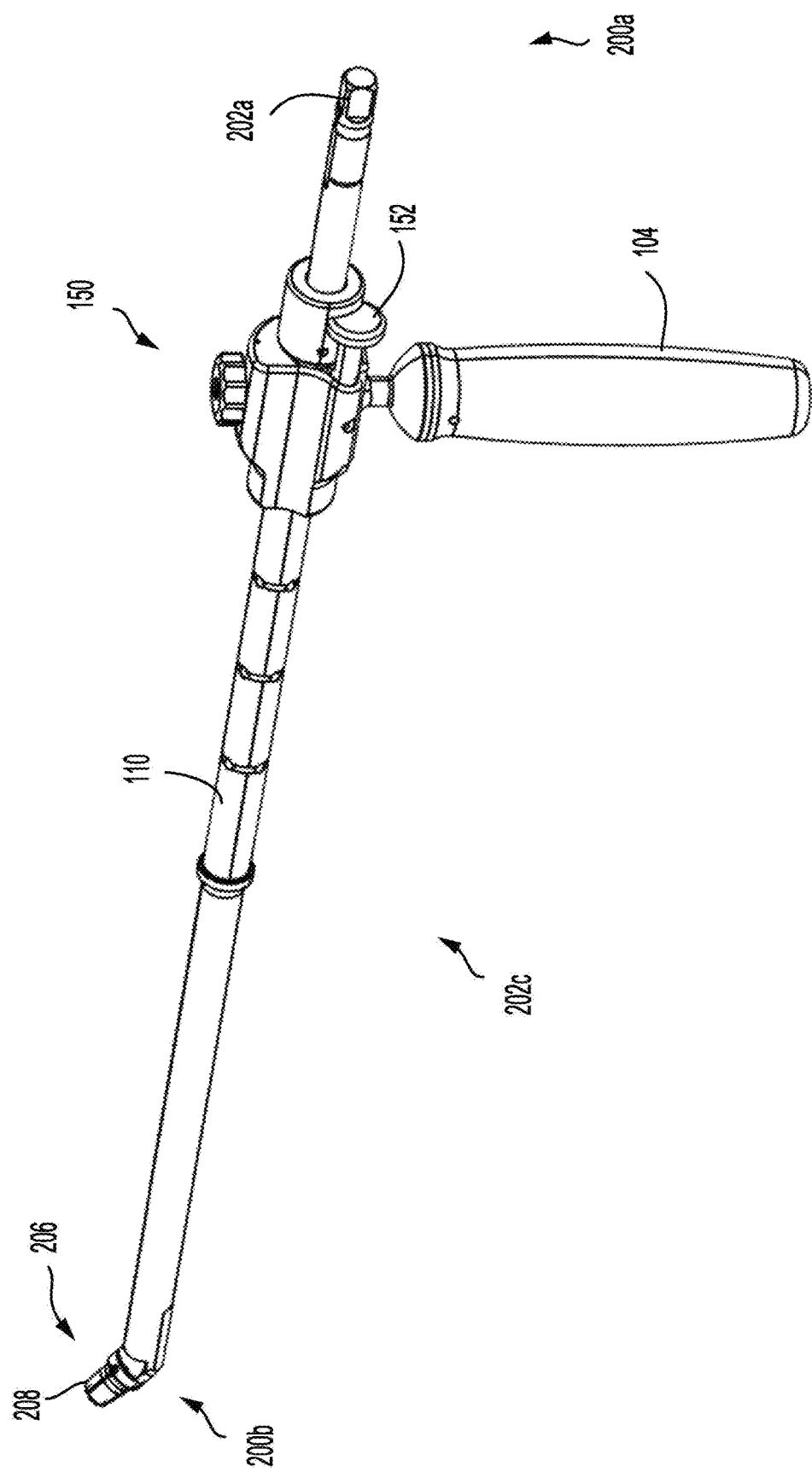
FIG. 16 is a side view of an example screwdriver in accordance with the principles of the present disclosure.

Referring generally to FIGS. 15-32B an example screwdriver 200 is illustrated. FIG. 15 is a perspective view of an example screwdriver 200 and FIG. 16 is a side view of the example screwdriver 200. Screwdriver 200 may include a proximal end 200a and a distal end 200b. Screwdriver 200 may also include a drive shaft 202, a positioning handle 104, a movable handle mechanism 150, a tip portion 206, a retaining cap 208, a movable handle mechanism 150, and a housing 110, among other things. Screwdriver 200 may include the same, similar, or substantially the same moving movable handle mechanism 150 as described above with respect to drill 100. Additionally, drill 100 and screwdriver 200 may include the same, similar, or substantially the same components and functionality, where applicable, unless the context clearly indicates otherwise.

Housing 110 may define a longitudinal axis L-A (see FIG. 2C) and movable handle mechanism 150 may move forward and backward along housing 110 in a direction parallel to longitudinal axis L-A. Additionally, movable handle mechanism 150 may rotate around housing 110 and/or the longitudinal axis defined by housing 110, for example. In various embodiments, movable handle mechanism 150 may move forward and backward in a longitudinal direction along the housing 110 between a proximal stop ring 113 and a distal stop ring 114, for example. Movable handle mechanism 150 may also be rotatable about housing 110, for example. In various embodiments, movable handle mechanism 150 may freely move forward and backward along housing 110 in a longitudinal direction and be securely coupled to housing 110 at any one channel 111 of a plurality of channels 111.

In the illustrated embodiment, five channels 111 are shown although there may be more or less depending on the particular embodiment Channels 111 may be spaced apart at any appropriate distance and need not be symmetrically spaced, for example. In at least one embodiment, channels 111 are symmetrically distributed between stop rings 113, 114 at a distance of about 25 mm, for example. Additionally, in various embodiments, movable handle mechanism 150 may freely rotate clockwise and/or counterclockwise around housing 110 and be securely coupled to housing 110 at any one detent 112 of a plurality of detents 112, for example. In the illustrated embodiment, each channel 111 includes a plurality of symmetrically spaced and radially disposed detents 112 around the circumferential surface of housing 110, for example. In various embodiments, there may be about 2-8 detents 112, 4-6 detents 112, and more particularly about 6 detents 112.

As described above with respect to FIG. 2D and FIG. 2E movable handle mechanism 150 may include a body portion 156 including a longitudinally extending aperture therein which housing 110 may extend through, for example. In turn, positioning handle 104 may be coupled to body portion 156 at an underside thereof. Body portion 156 may include a cavity for receiving actuator 152, for example. Actuator 152 may be referred to as a positioning actuator and take various forms. In the illustrated embodiment, actuator 152 comprises a spring loaded push button, for example. In operation, an end user may depress actuator 152 and thereby unseat positioning ball 154 from a corresponding detent 112. After releasing actuator 152 spring 155 may bias positioning ball 154 against housing 110 to seat positioning ball 154 in any one of the plurality of detents 112, for example. In various embodiments, actuator 152 includes ramped surfaces 152a which facilitate seating positioning ball 154 as explained above. Movable handle mechanism 150 may also include at least one locking actuator configured to securely and rigidly couple movable handle mechanism 150 to housing 110, for example. In the example embodiment, locking actuator 151 comprises a rotatable knob configured to frictionally engage housing 110 by moving forward and backward in a direction substantially perpendicular to the longitudinal axis, for example. In various embodiments (not illustrated), locking actuator 151 may include a tip portion that may be seated within a corresponding detent 112 and/or channel 111, for example. The tip portion may have a size and shape generally corresponding to a size and shape of a corresponding detent 112 and/or channel 111, for example.

Referring back to FIGS. 15-28B drive shaft 202 may be configured to connect and disconnect with various types of drivers including manually operated handles and mechanically powered drive means that may be of a ratcheting or non-ratcheting type and which are discussed in further detail above (see, e.g., FIGS. 10-11). For example, drive shaft 202 may include a drive portion 202a disposed at a distal end thereof, a drive end 202b disposed at a proximal end thereof, and a main drive shaft portion 202c extending in a longitudinal direction through a housing 110. Drive portion 202a may comprise a variety of drive interfaces for coupling and uncoupling with various manually operated ratcheting handles and powered drivers. Drive shaft 202 may freely rotate inside of housing 110 to transfer rotational force applied at the drive portion 202a to drive end 202b. Positioning handle 104 may be securely held in place while drive shaft 202 freely rotates within housing 110. Positioning handle 104 may be configured to assist with maintaining and controlling the screwdriver 200, e.g., in view of torque transmitted through drive shaft and the corresponding resultant return forces. At least one advantage of positioning handle 104 is that a surgeon may have greater control maintaining screwdriver 200 in a desired position while driving a bone screw 300. For example, when installing a bone screw 300 into the anatomy of a patient a return force may apply a rotational force against the screwdriver 200 and a surgeon may be able to maintain the screwdriver 200 in the desired position.

Figure 17:
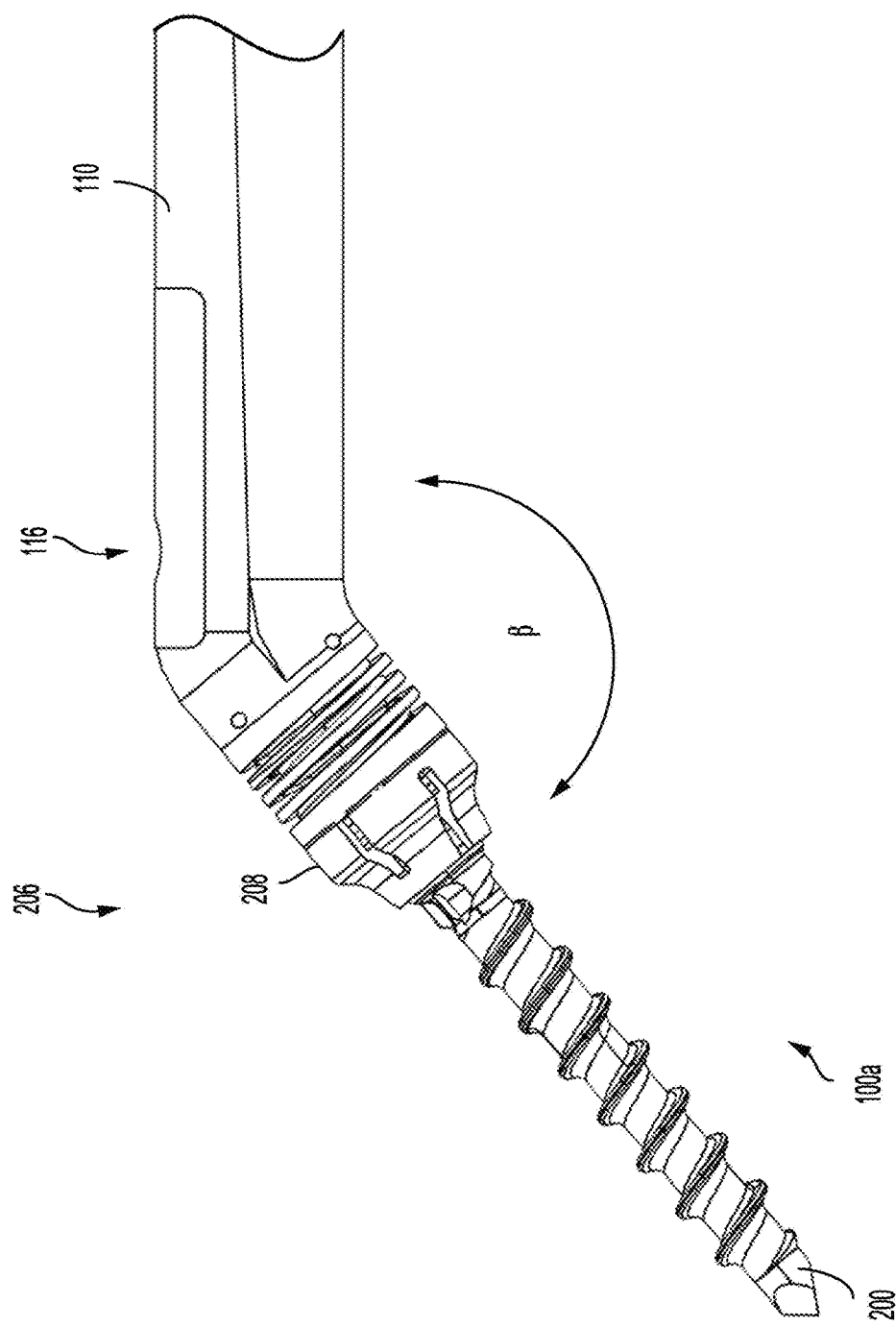
FIG. 17 is a magnified view of the tip portion of an example screwdriver in accordance with the principles of the present disclosure.

FIG. 17 is a magnified view of the tip portion 206 of an example screwdriver 200 in accordance with the principles of the present disclosure. Tip portion 206 may be angled at a degree β (Beta) with respect to a longitudinal direction of housing 110 and/or drive shaft portion 202c (see FIG. 25). In some embodiments, tip portion 206 is angled such that the degree β corresponds to the desired inclination of bone screw 300. In some embodiments, the degree β corresponds to an inclination of a bone screw aperture of a medical plate or medical device, e.g., medical device 1000 is a spinal implant including at least one bone screw aperture 1001 (see FIG. 29). For example, tip portion 206 may be inclined about 20°-60°, more particularly about 30°-50°, and even more particularly about 40°-45°, with respect to a longitudinal direction of housing 110. However, it shall be understood that tip portion 206 may be angled at any degree β Similarly, bone screw apertures 1001 may be angled at any degree with respect to endplates 1010, 1020 and tip portion 206 may be angled at a corresponding degree β to facilitate the installation of bone screw 300 therein. This angled arrangement may be advantageous for driving bone screw 300 while medical device 1000 is positioned between adjacent vertebral bodies. Furthermore, this angled arrangement may be advantageous to avoid anatomical landmarks and features such as the pelvic ring, rib cage, and iliac crest, of a patient, for example.

Figure 18A:
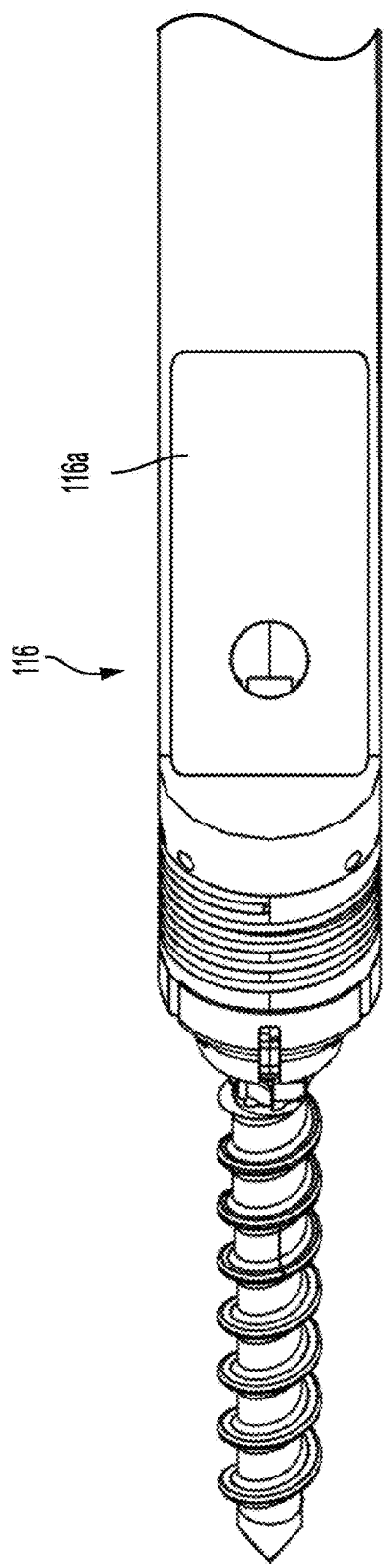
FIG. 18A is a top down view of a flushing portion of an example screwdriver in accordance with the principles of the present disclosure.
Figure 18B:
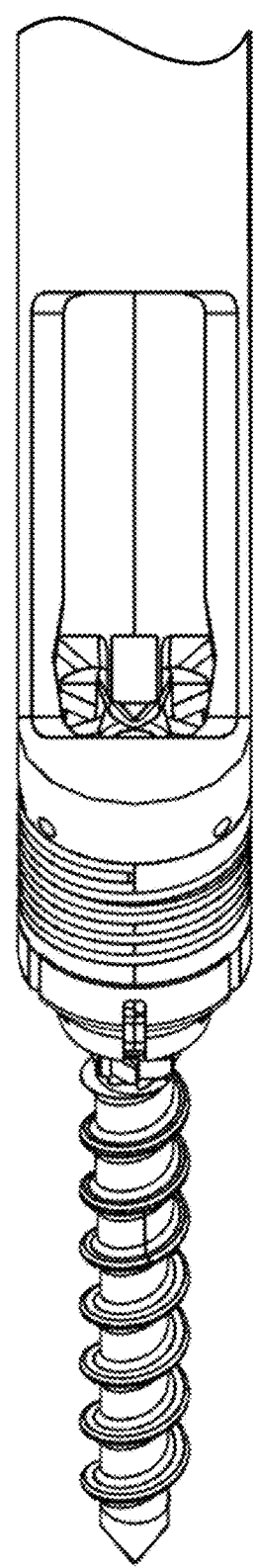
FIG. 18B is a top down view of a flushing portion of an example screwdriver with partially removed parts for ease of understanding in accordance with the principles of the present disclosure.

FIGS. 18A and 18B illustrate an example screwdriver 200 that may include a flushing hole 116 having a flushing path to clean the tip portion 206, or to lubricate the mechanism. For example, as shown in FIG. 18A a flushing hole 116 is shown, and in FIG. 18B a cover 116a is removed to illustrate the flushing path. Flushing hole 116 may be advantageous for cleaning the interior orifices of tip portion 206.

Figure 19:
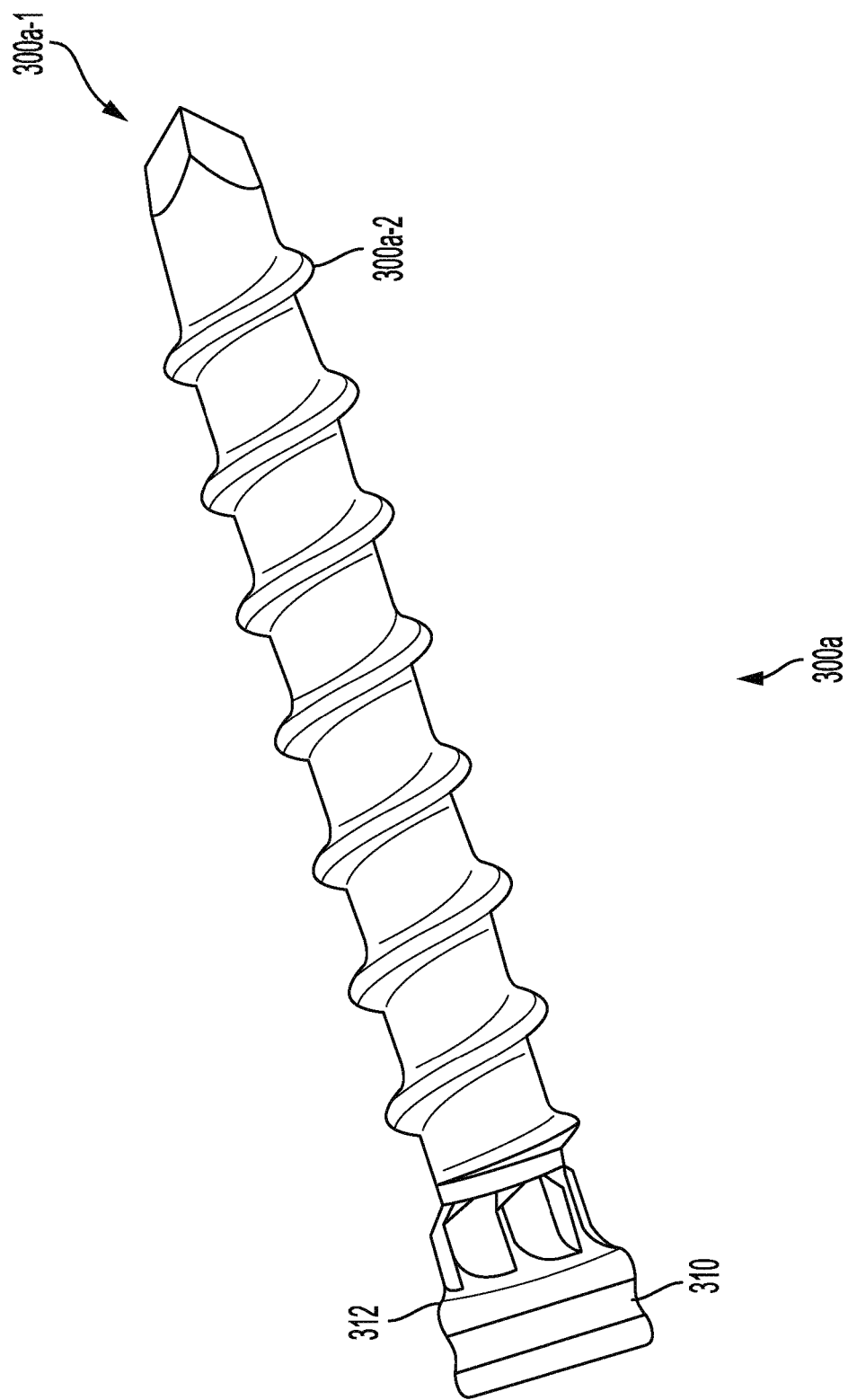
FIG. 19 is a perspective view of an example bone screw suitable for use with disclosed embodiments in accordance with the principles of the present disclosure.
Figure 20:
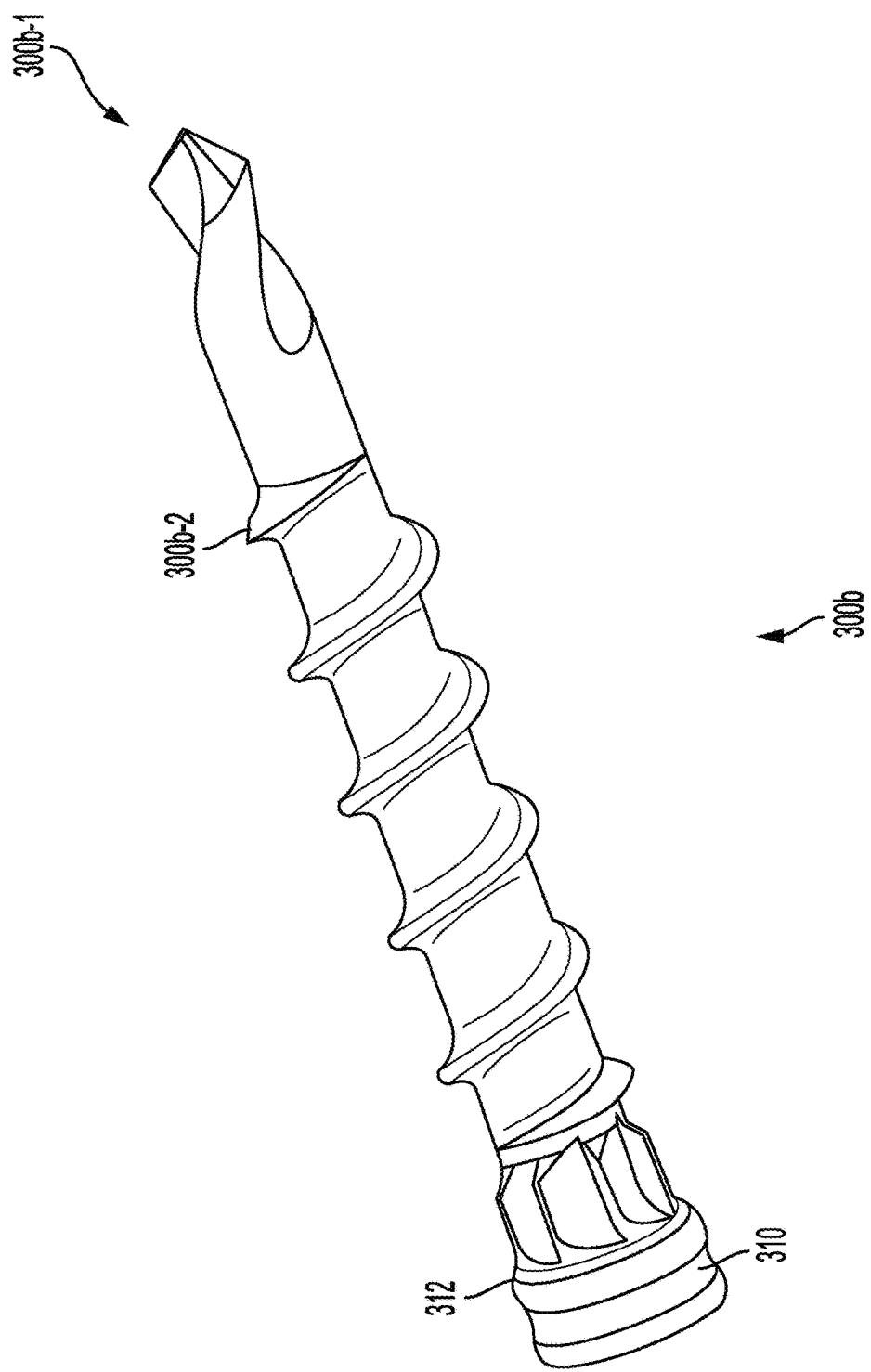
FIG. 20 is a perspective view of an example bone screw suitable for use with disclosed embodiments in accordance with the principles of the present disclosure.
Figure 21:
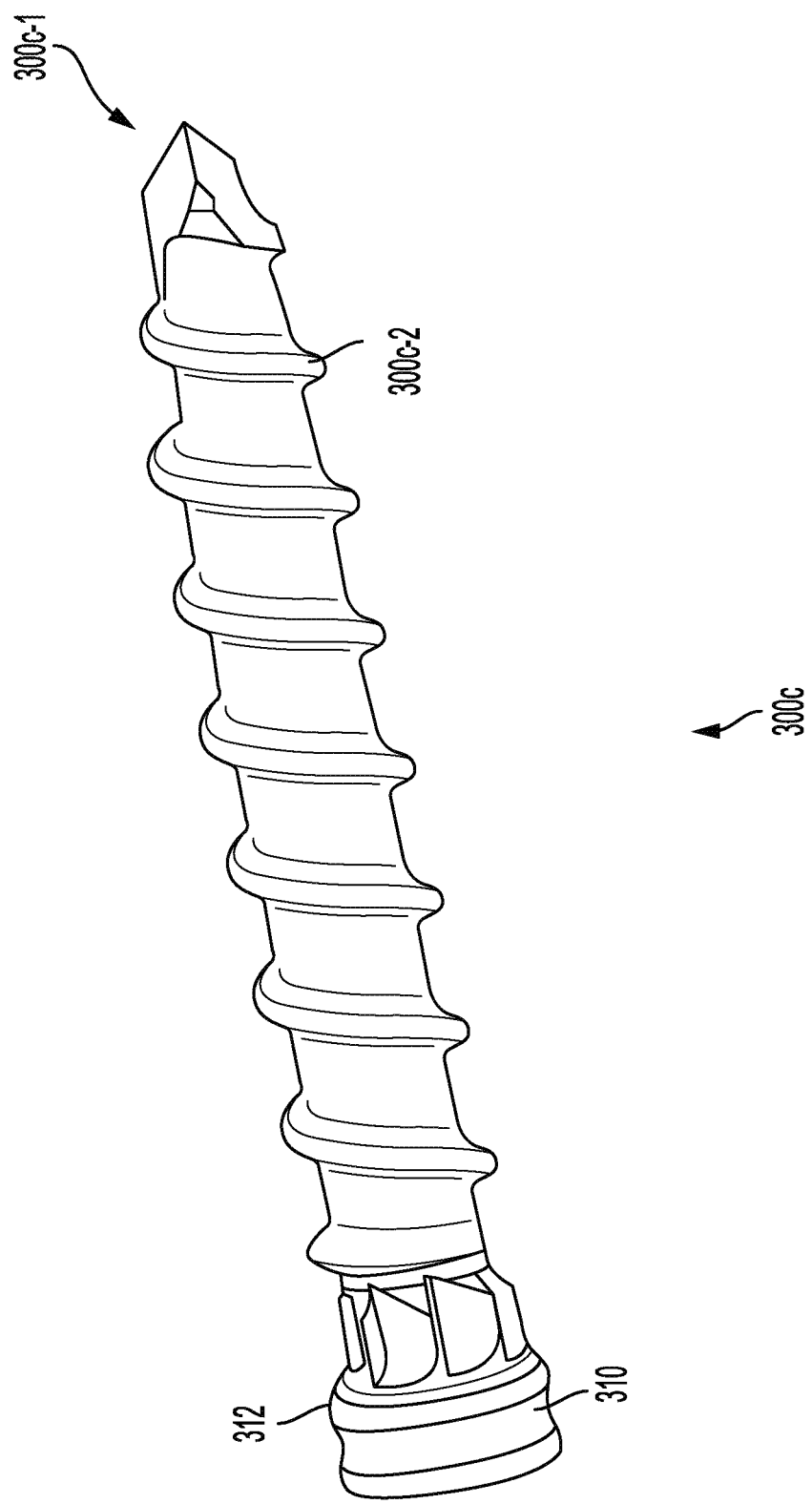
FIG. 21 is a perspective view of an example bone screw suitable for use with disclosed embodiments in accordance with the principles of the present disclosure.

FIG. 19 is a perspective view of an example trocar tip bone screw 300a suitable for use with disclosed embodiments in accordance with the principles of the present disclosure. FIG. 20 is a perspective view of an example flutes or fluted tip bone screw 300b suitable for use with disclosed embodiments in accordance with the principles of the present disclosure. FIG. 21 is a perspective view of an example speed bone screw suitable for use with disclosed embodiments in accordance with the principles of the present disclosure. Each bone screw 300a, 300b, 300c may be referred to throughout the disclosure generally as bone screw 300 to refer to bone screws generally and including any of the example bone screws 300a, 300b, 300c. Additionally, each bone screw 300a, 300b, 300c may have a single or multiple thread pitch and sizing that corresponds to a size of bone screw aperture 1001, for example.

Trocar tip bone screw 300a includes an angled tip portion 300a-1 and a thread pattern including threads 300a-2. Threads 300a-2 may be spaced back from angled tip portion 300a-1 which may facilitate with aligning bone screw 300a with bone screw aperture 1001. For example, in some embodiments, threads 300a-2 are spaced back about 3 mm from angled tip portion 300a-1. Fluted tip bone screw 300b includes a cutting tip 300b-1 and a thread pattern included threads 300b-2. Cutting tip 300b-1 may extend a relatively long distance from the beginning of threads 300b-2 such that the cutting tip 300b-1 may pre-drill into an anatomical feature or tissue such as a bone or an adjacent vertebral body before the threads 300b-2 engage with bone screw aperture 1001. For example, in some embodiments, threads 300b-2 are spaced back about 8 mm from cutting tip 300b-1. Speed bone screw 300c includes a conical tip 300c-1 and a thread pattern including threads 300c-2. Different from trocar tip bone screw 300a and fluted tip bone screw 300b, threads 300c-2 of speed bone screw 300c may begin immediately adjacent conical tip 300c-1.

Each of the example bone screws 300a, 300b, 300c may be configured for use with example screwdrivers 200 disclosed herein. Additionally, each of the example bone screws 300a, 300b, 300c may include an indent 310 spanning the circumference of the head portion and an adjacent edge portion 312 spanning the circumference of the head portion. In some embodiments, indent 310 may be defined by an arcuate circumferential groove that spans the circumference of a midsection of the head of bone screw 300. Additionally, in some embodiments, edge portion 312 may be defined by an arcuate or chamfered edge spanning the circumference of the head portion adjacent the threads of bone screw 300. The indent 310 and/or edge portion 312 may be advantageous for clipping and/or retaining bone screws 300a, 300b, 300c in screwdriver 200, as will be explained in more detail below.

Figure 22:
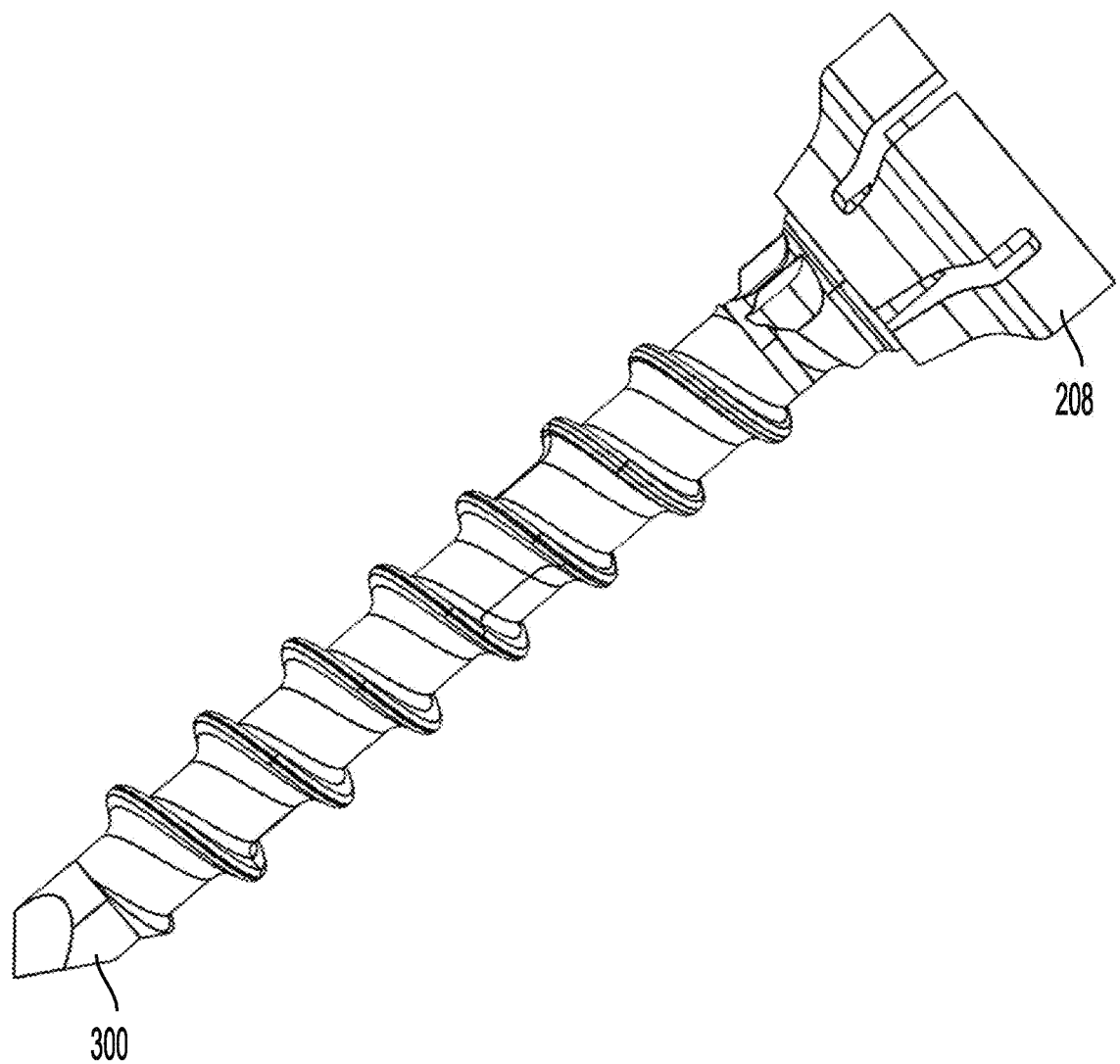
FIG. 22 is a perspective view of an example bone screw coupled to a retaining cap in accordance with the principles of the present disclosure.
Figure 23A:
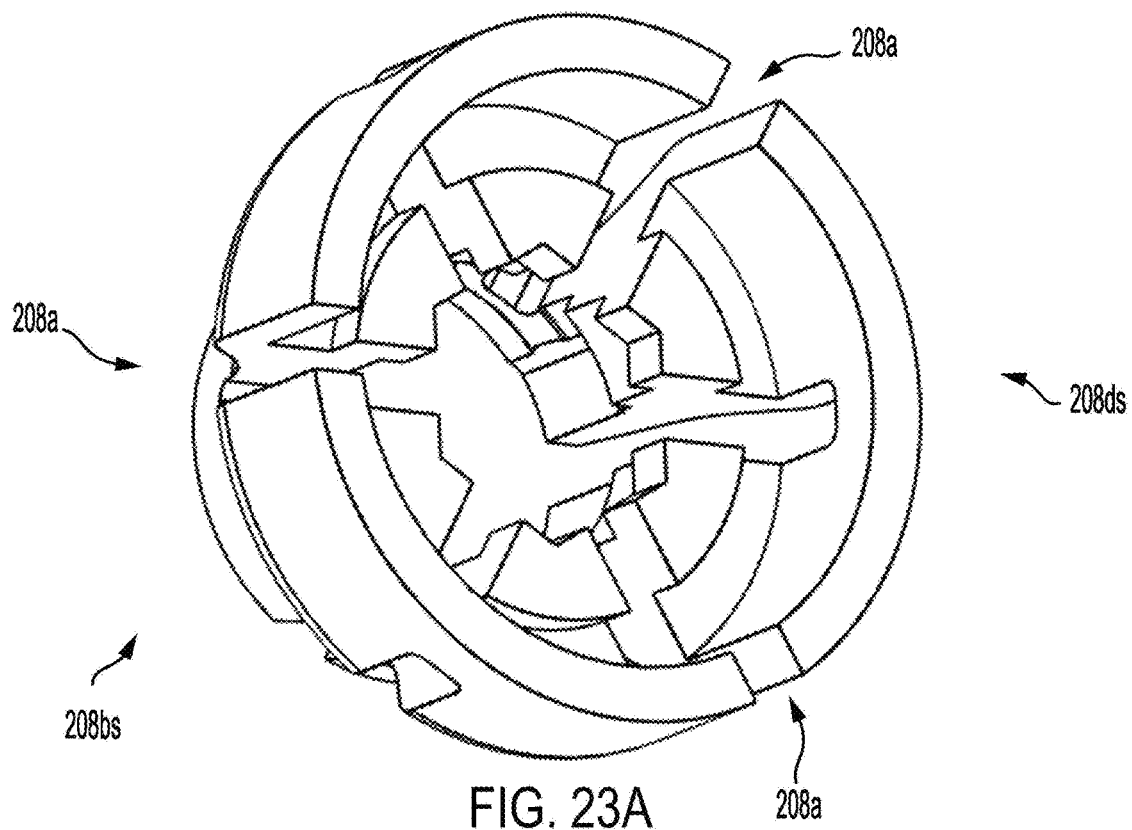
FIG. 23A is a perspective view of a retaining cap viewed from a drive shaft connecting side in accordance with the principles of the present disclosure.
Figure 23B:
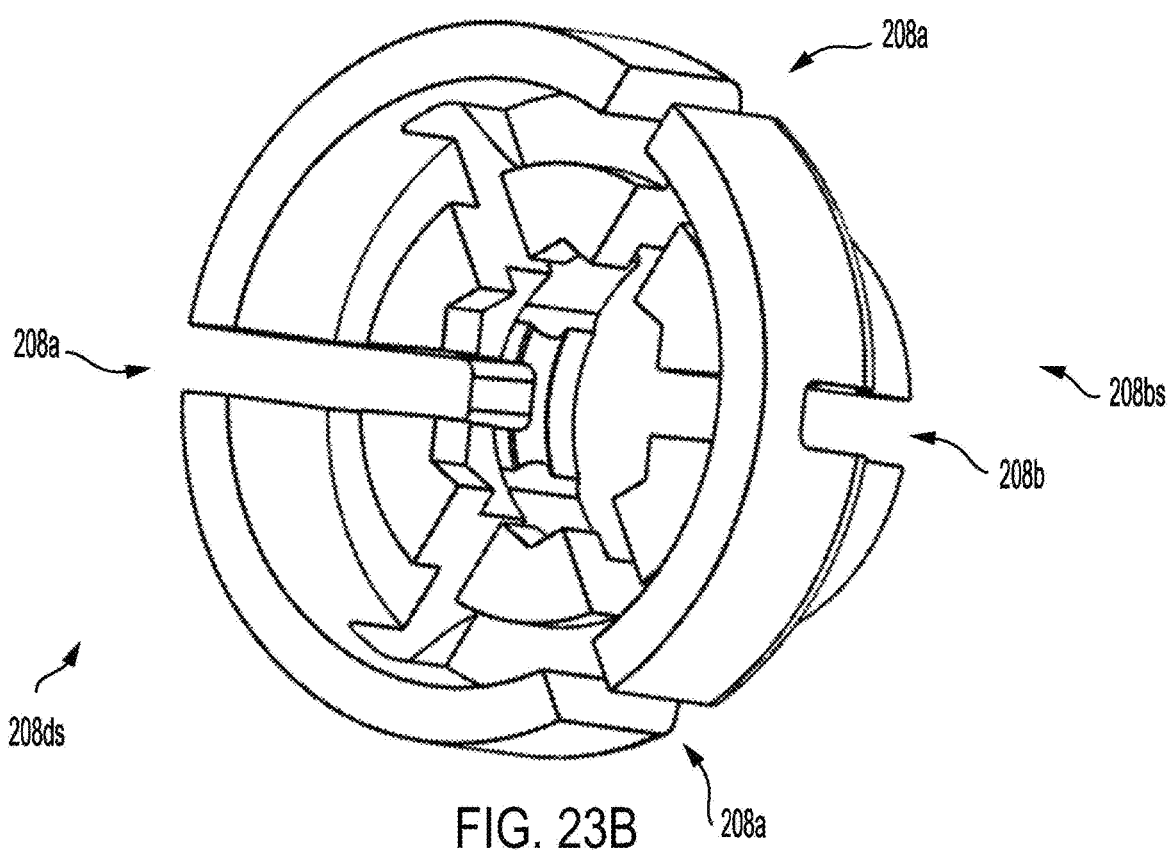
FIG. 23B is an alternate perspective view of a retaining cap viewed from a drive shaft connecting side in accordance with the principles of the present disclosure.
Figure 24A:
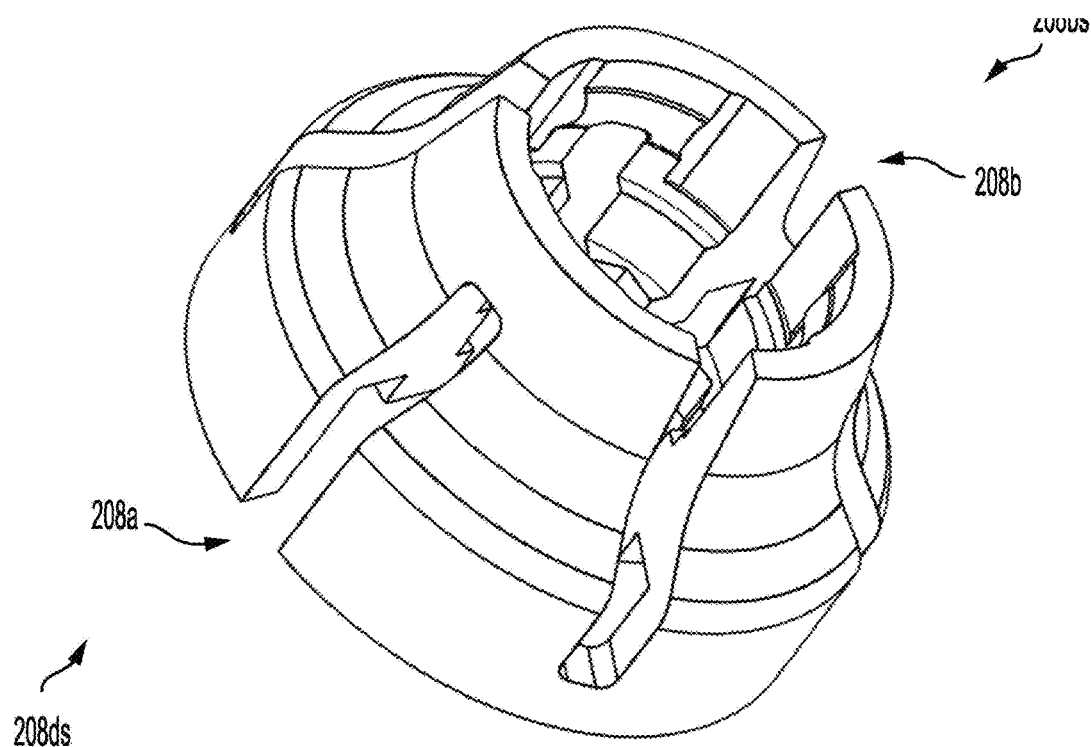
FIG. 24A is a perspective view of a retaining cap viewed from a bone screw retaining side in accordance with the principles of the present disclosure.
Figure 24B:
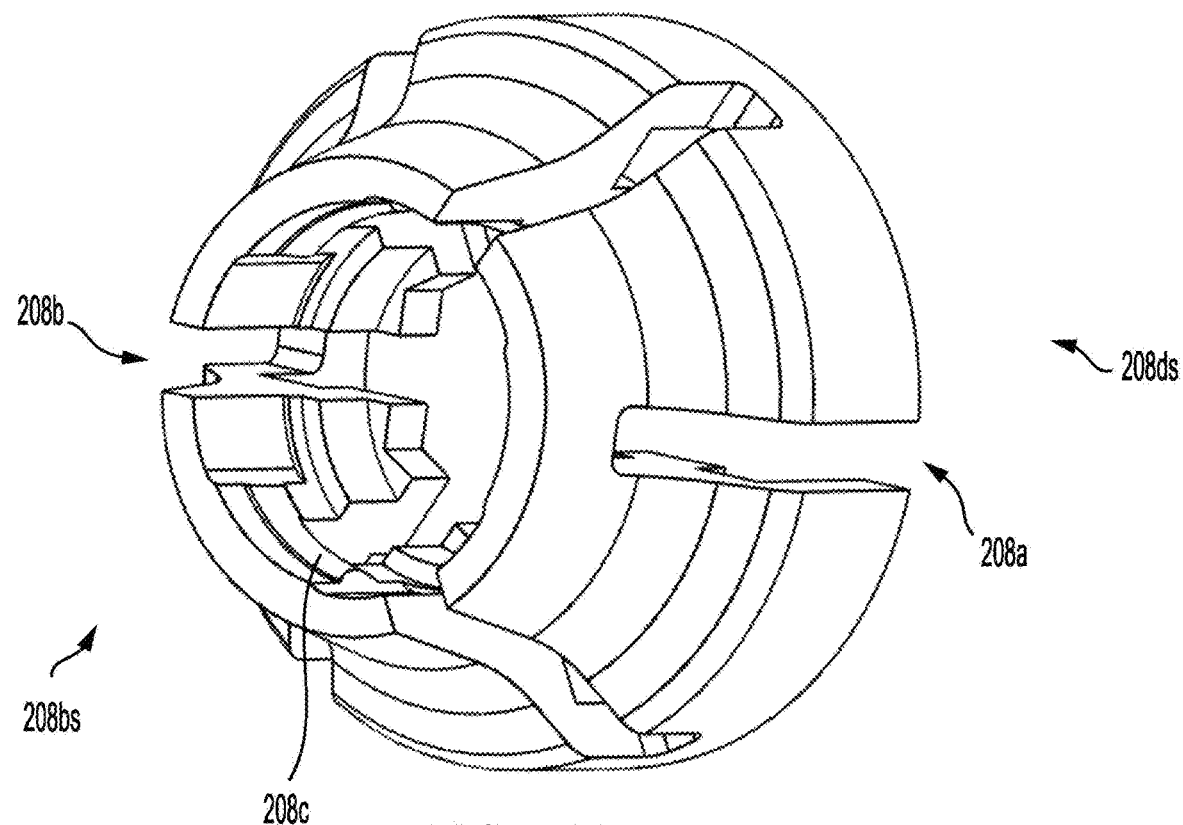
FIG. 24B is a perspective view of a retaining cap viewed from a bone screw retaining side in accordance with the principles of the present disclosure.
Figure 25:
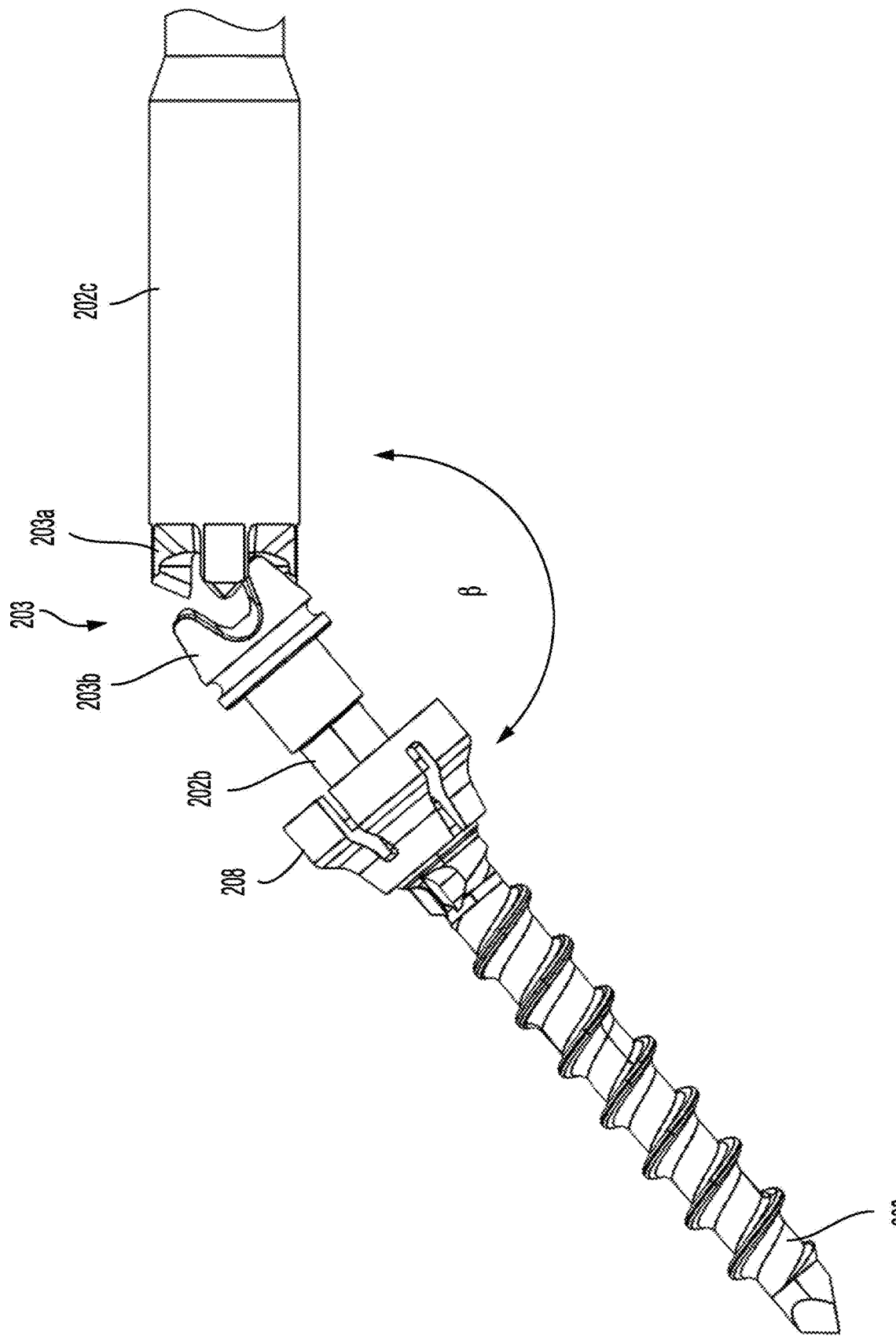
FIG. 25 is a side view of a gear mechanism in accordance with the principles of the present disclosure.
Figure 26A:
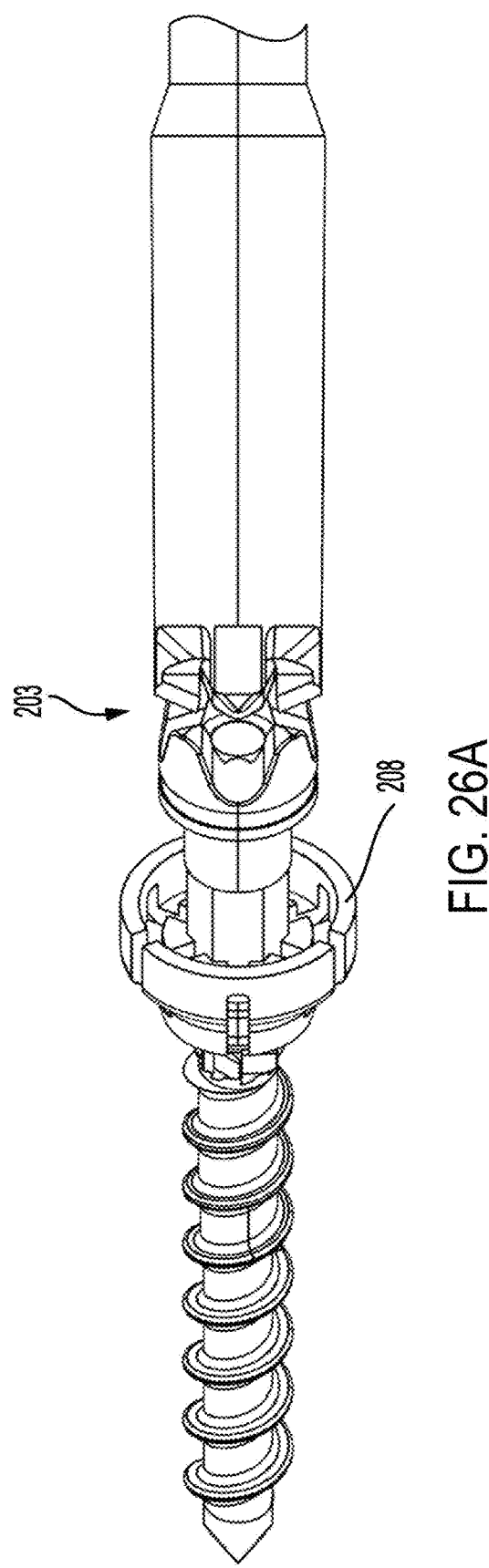
FIG. 26A is a top view of a gear mechanism in accordance with the principles of the present disclosure.
Figure 26B:
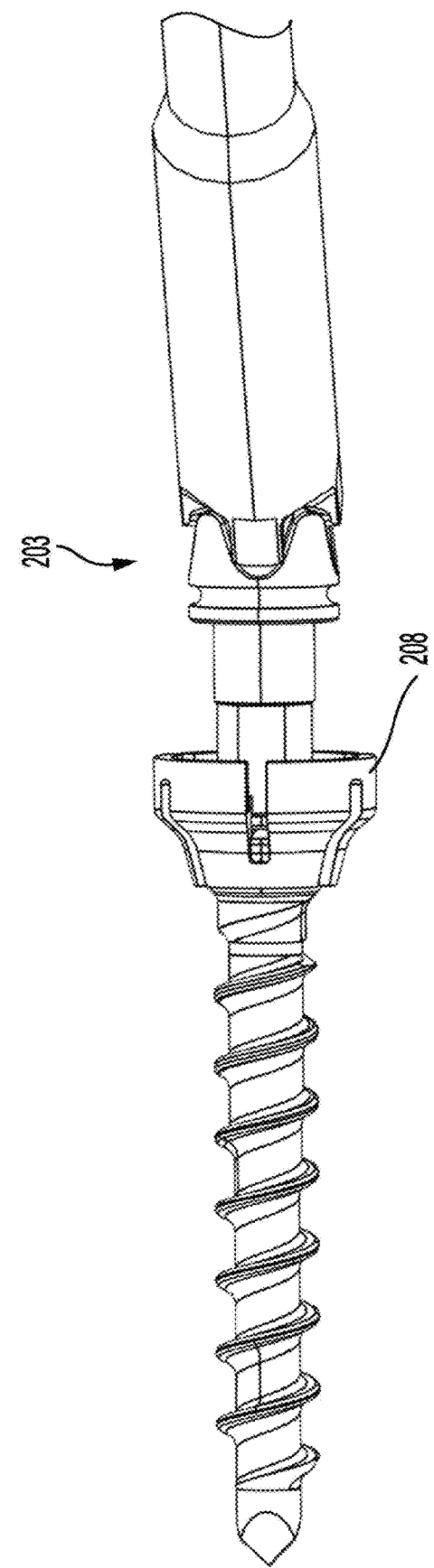
FIG. 26B is a bottom view of a gear mechanism in accordance with the principles of the present disclosure.

FIG. 22 is a perspective view of an example bone screw 300 coupled to and retained by an example retaining cap 208 in accordance with the principles of the present disclosure. FIGS. 23A and 23B are perspective views of retaining cap 208 viewed from a drive shaft connecting side 208ds in accordance with the principles of the present disclosure and FIGS. 24A and 25B are perspective views of retaining cap 208 viewed from a bone screw connecting side 208bs in accordance with the principles of the present disclosure. Retaining cap 208 may be composed of elastomeric materials, thermoplastic materials, metallic materials, and various combinations thereof. In one embodiment, retaining cap 208 is composed of metallic material, e.g., stainless steel and/or titanium. In another embodiment, retaining cap 208 is composed of elastomeric material, e.g., rubber and/or high-density rubber. In another embodiment, retaining cap 208 is composed of thermoplastic material, e.g., Polyether ether ketone (PEEK) and/or other organic thermoplastic polymers in, e.g., the polyaryletherketone (PAEK) family. In another embodiment, retaining cap 208 is composed of polyphenylsulfone (PPSU), also referred to as Radel by those with skill in the art.

In the example embodiment, the drive shaft connecting side 208ds includes a plurality of first aperture channels 208a and the bone screw connecting side 208bs includes a plurality of second aperture channels 208b. In some embodiments, a circumference of the drive shaft connecting side 208ds may be greater than a circumference of the bone screw connecting side 208bs. First aperture channels 208a may take the shape of a slit or narrow void extending from the drive shaft connecting side 208ds towards the bone screw connecting side 208bs. Second aperture channels 208b may take the shape of a slit or narrow void extending from the drive shaft connecting side 208ds towards the bone screw connecting side 208bs. In the example embodiment, three (3) first aperture channels 208a and three (3) second aperture channels 208b are illustrated, although retaining cap 208 may have any number of aperture channels 208a, 208b. For example, other embodiments may include two aperture channels 208a, 208b, four aperture channels 208a, 208b, or five aperture channels 208a, 208b, for example. In the disclosed embodiment, first aperture channels 208a are spaced apart symmetrically from one another around the circumference of the drive shaft connecting side 208ds. Similarly, second aperture channels 208b are spaced apart symmetrically from one another around the circumference of the bone screw connecting side 208bs. Furthermore, each first aperture channel 208a may be spaced between two immediately adjacent second aperture channels 208b at a midpoint distance between the two immediately adjacent second aperture channels 208b Similarly, each second aperture channel 208b may be spaced between two immediately adjacent first aperture channels 208a at a midpoint distance between the two immediately adjacent first aperture channels 208a. For example, as illustrated the aperture channels 208a, 208b are symmetrically disposed around the retaining cap 208 on opposite sides thereof with respect to one another. Additionally, each aperture channel may extend from about 10%-95% of the length of retaining cap 208 and the length and width of each aperture channel may be adjusted to increase or decrease the desired flexibility of retaining cap 208.

Additionally, retaining cap 208 may include a plurality of bumps 208c at a bone screw connecting side 208bs. Bumps 208c may be inset from an outermost surface of the bone screw connecting side 208bs on an interior thereof. Bumps 208c may extend along the internal surface of retaining cap 208 at the bone screw connecting side 208bs. In the disclosed embodiment, three bumps 208c are illustrated although there may be more or less, for example two bumps 208c, four bumps 208c, or five bumps 208c. In the disclosed embodiment, the number of bumps 208c may correspond to the number of aperture channels 208b. For example, in the disclosed embodiment there may be three aperture channels 208b and three bumps 208c where each bump is disposed symmetrically between adjacent aperture channels 208b. Furthermore, a curved distance along the interior circumference of bone screw connecting side 208bs between adjacent aperture channels 208b may be greater than a curved distance (length) of bumps 208c. For example, in some embodiments, a circumferential length of bumps 208c may range from about 25%-75% of the circumferential distance between adjacent aperture channels 208b. Additionally, when viewed in cross section, bump 208c may be shaped like an arc of a circle or cylinder. However, in other embodiments, bump 208c may have alternate shapes such as prismoidal, polygonal, conical, etc. In the disclosed embodiment, bump 208c may have a cross sectional shape generally corresponding to indent 310. Accordingly, those with skill in the art will recognize that bump 208c and indent 310 may take any shape and that it in some embodiments it may be advantageous that their shapes correspond with one another.

At least one advantage of the geometrical arrangement of aperture channels 208a, 208b is that they may allow the retaining cap 208 to deform, at least partly, to couple/uncouple with the head of a bone screw 300 and/or drive end 202b. For example, a bone screw 300 may be inserted into the retaining cap 208 and clipped or retained by the retaining cap 208 by inserting the head of the bone screw 300 into the retaining cap 208 with a sufficient force, i.e., a clipping force. When inserting the head of the bone screw 300 into the retaining cap 208, the retaining cap 208 may deform, at least partly, consistent with the above disclosure when clipping the bone screw 300. In some embodiments, a clipping force may be about 1 N-6 N (Newtons), more particularly about 2 N-4 N, and even more particularly about 2.5 N Similarly, the retaining cap 208 may be attached to drive end 202b. For example, retaining cap 208 may be attached to drive end 202b with an attachment force of about 10 N-40 N, more particularly about 15 N-30 N, and even more particularly about 20 N. In this way, retaining cap 208 may be considered elastic although not necessarily composed of an elastomeric material.

A particular advantage of a flexible retaining cap 208 as described herein is that it may (1) retain a bone screw 300 therein with a clipping force and (2) automatically release the bone screw 300 when it is sufficiently installed or anchored. For example, during an installation or driving procedure, a bone screw 300 may be retained in the retaining cap 208 until the bone screw 300 is sufficiently installed in a target object or surgical site such that a sufficient extraction force pulls the bone screw 300 from the retaining cap 208, i.e., the extraction force exceeds the clipping or retaining force. For example, when driving the bone screw 300 into the target object or surgical site, the retaining cap 208 may deform, at least partly, consistent with the above disclosure when releasing the bone screw 300. In some embodiments, an extraction force may be about 2 N-30 N, more particularly about 10 N-20 N, and even more particularly about 15 N. In some embodiments, a ratio of the clipping force to the extraction force may about 1:15, more particularly about 1:10, and even more particularly about 1:6. For example, in at least one embodiment the retaining cap 208 is composed of a PEEK material and the clipping force is about 2.5 N and the extraction force is about 15 N.

Referring generally to FIGS. 25-27B, an example gear mechanism 203 may be provided. Gear mechanism 203 may include worm gears, beveled gears, miter gears, planetary gears, sliding gears, helical or spiral gears, gear coupling parts, pawls, having teeth of various sizing and shapes for directing a rotation of the drive shaft 202 to drive end 202b. For example, applying a rotation force at drive portion 202a may apply an equal or substantially equal rotation force at drive end 202b because the gear mechanism 203 may redirect the rotation force. As illustrated, gear mechanism 203 may include a first group of teeth 203a that are meshed with a second group of teeth 203b. In the example embodiment, the first group of teeth 203a includes fourth teeth and the second group of teeth 203b includes four teeth although the total number of teeth may be more or less. Those with skill in the art will readily appreciate that the particular geometry and number of teeth 203a, 203b may be modified to accommodate any particular angle β (see FIG. 25). Additionally, in some embodiments, gear mechanism 203 may be designed to provide a mechanical advantage, such increasing or lowering the speed of rotation. For example, when a ratio of teeth sizing of teeth 203a, 203b is inferior or superior with respect to the other.

Figure 27A:
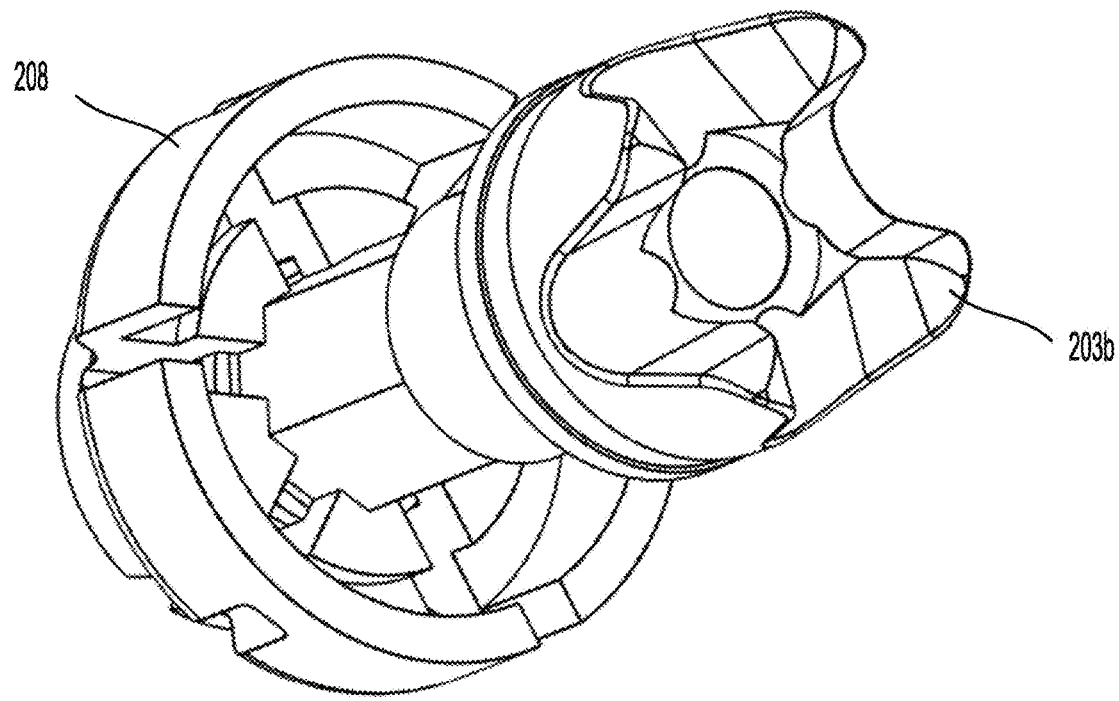
FIG. 27A is a perspective view of a first portion of a gear mechanism and a retaining cap in accordance with the principles of the present disclosure.
Figure 27B:
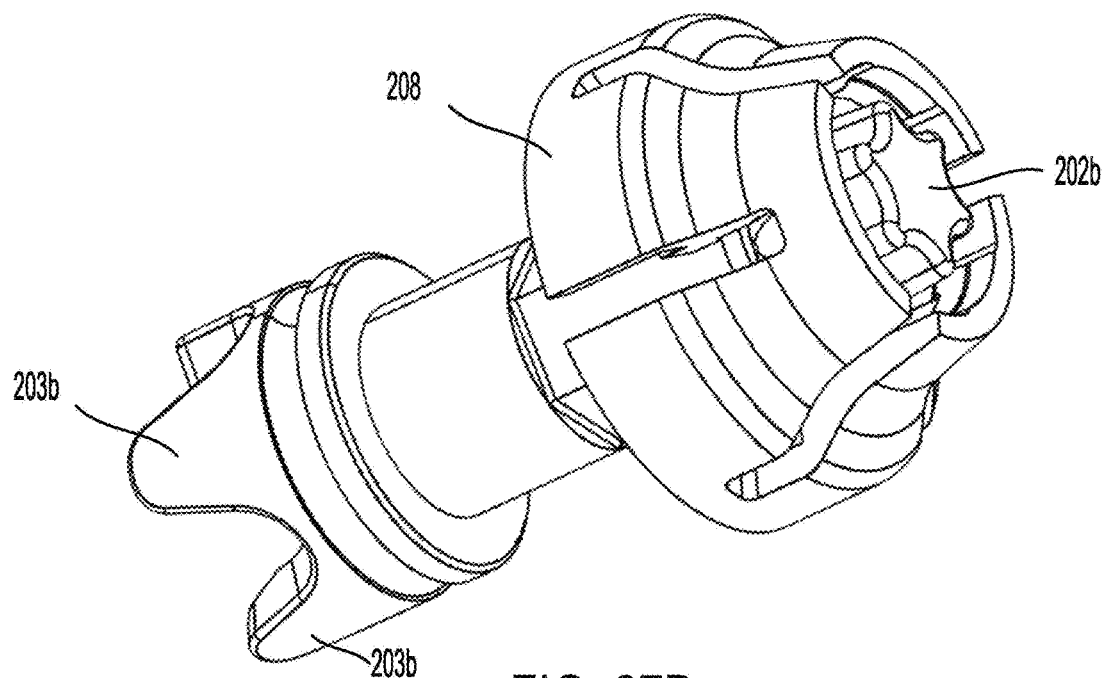
FIG. 27B is a perspective view of a first portion of a gear mechanism and a retaining cap in accordance with the principles of the present disclosure.

As illustrated best in FIG. 27B, drive end 202b may disposed in an internal cavity of retaining cap 208 such that it may mate with a head of a corresponding bone screw 300. Additionally, the retaining cap 208 may be coupled to drive end 202b in such a way that it will also rotate when drive end 202b rotates. In the illustrated embodiment, drive end 202b includes a torx head driver configuration, although other designs are contemplated, including star or hexalobular configurations. For example, the drive end 202b may resemble the geometry of the tip of a torx driver, hex driver, phillips driver, square head driver, hexalobular driver, polygonal driver, or the like. In at least one embodiment, a Torx T20 size driver may be used.

Figure 28:
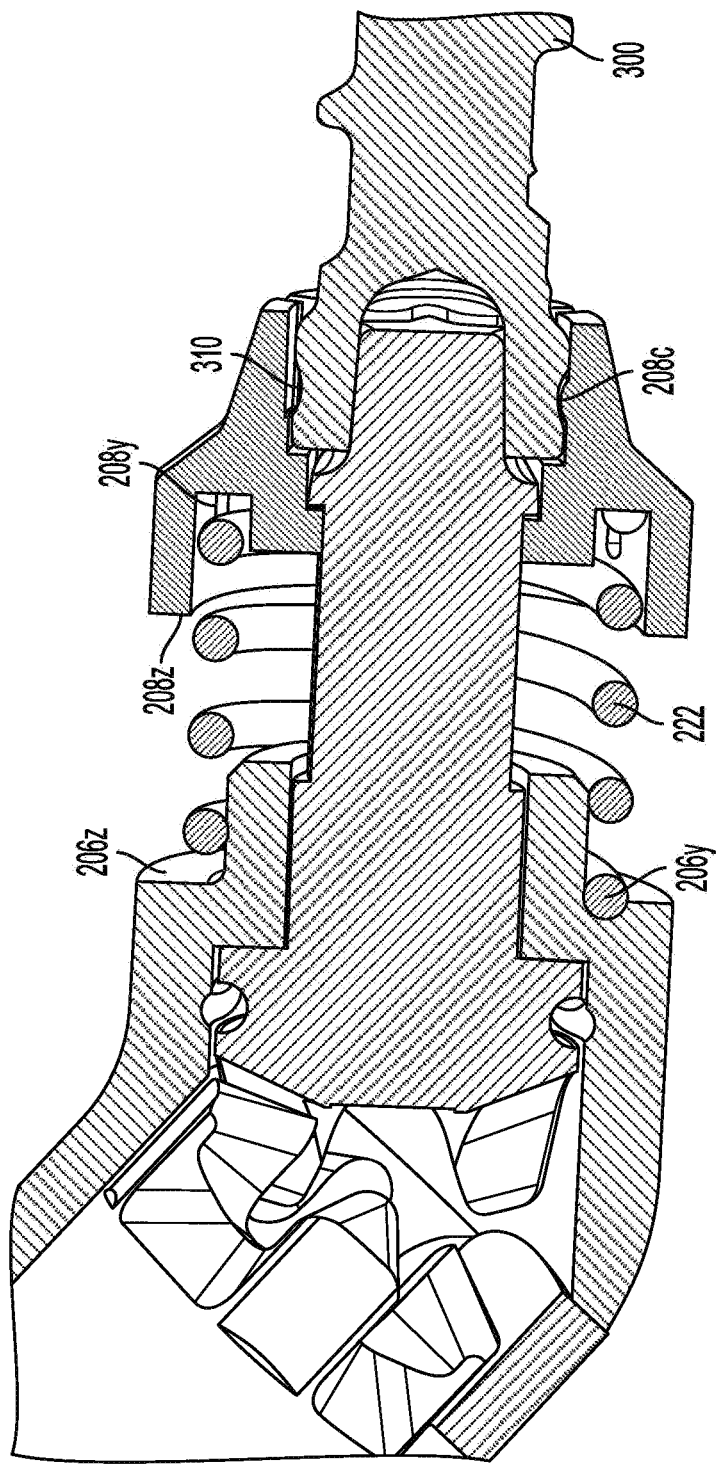
FIG. 28 is a cross section view of a tip portion of an example screwdriver in accordance with the principles of the present disclosure.
Figure 29:
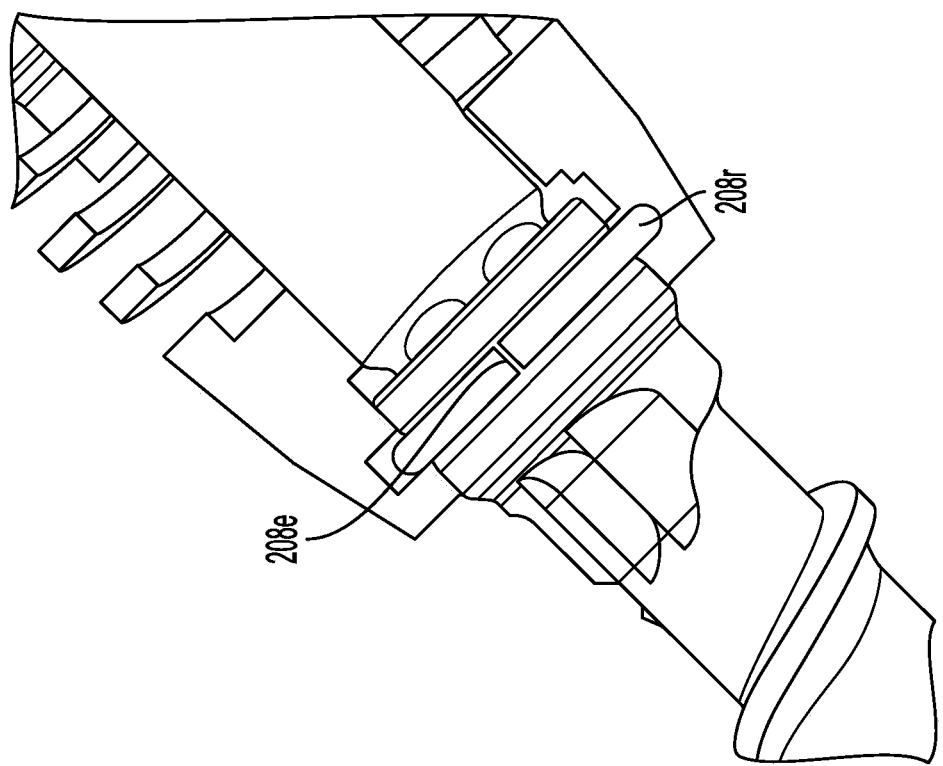
FIG. 29 is a removed parts view of a tip portion of an example screwdriver in accordance with the principles of the present disclosure.
Figure 30:
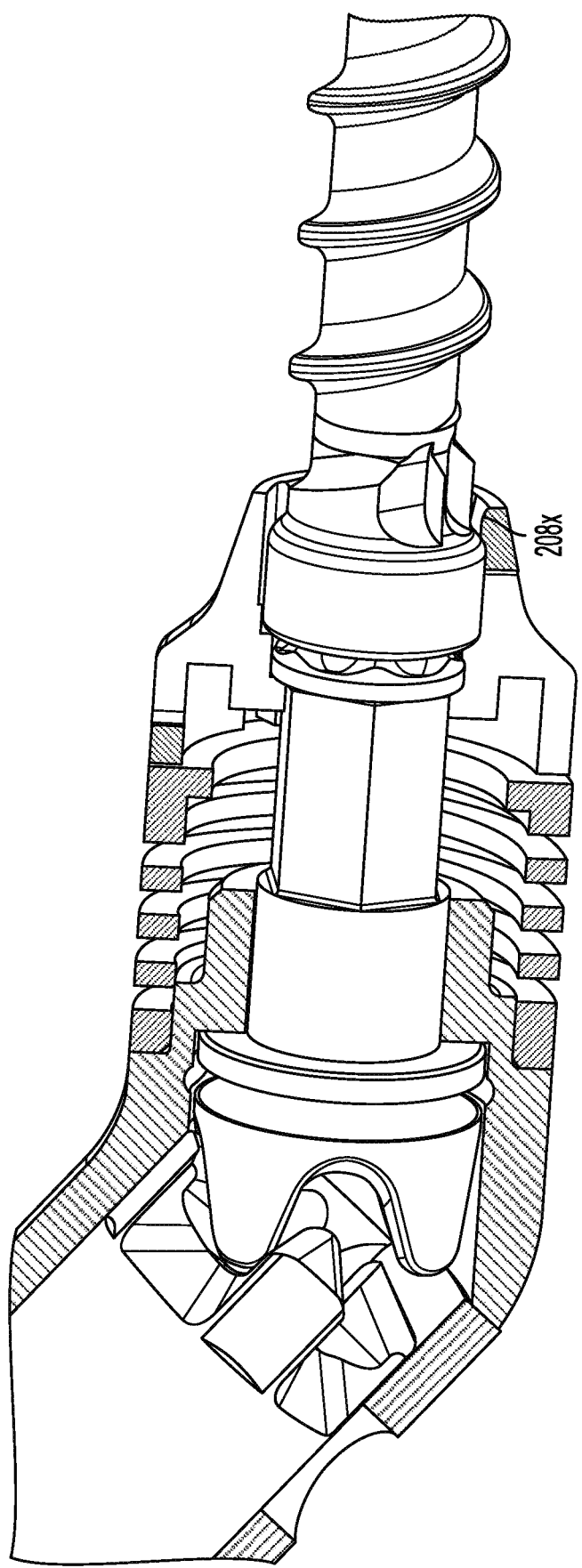
FIG. 30 is a removed parts view of an example gear mechanism in accordance with the principles of the present disclosure.
Figure 31:
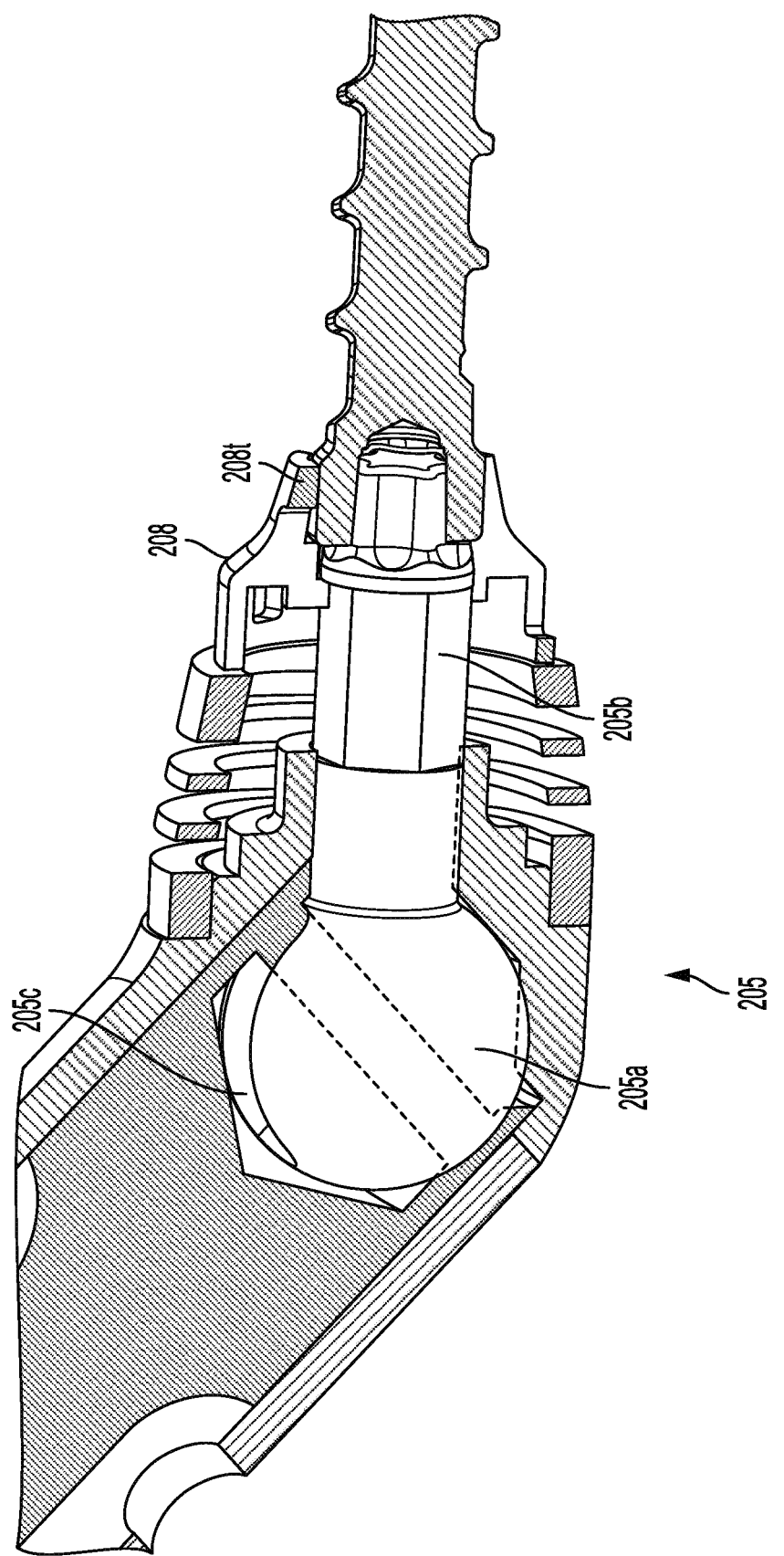
FIG. 31 is a removed parts view of an alternate example gear mechanism in accordance with the principles of the present disclosure.
Figure 32A:
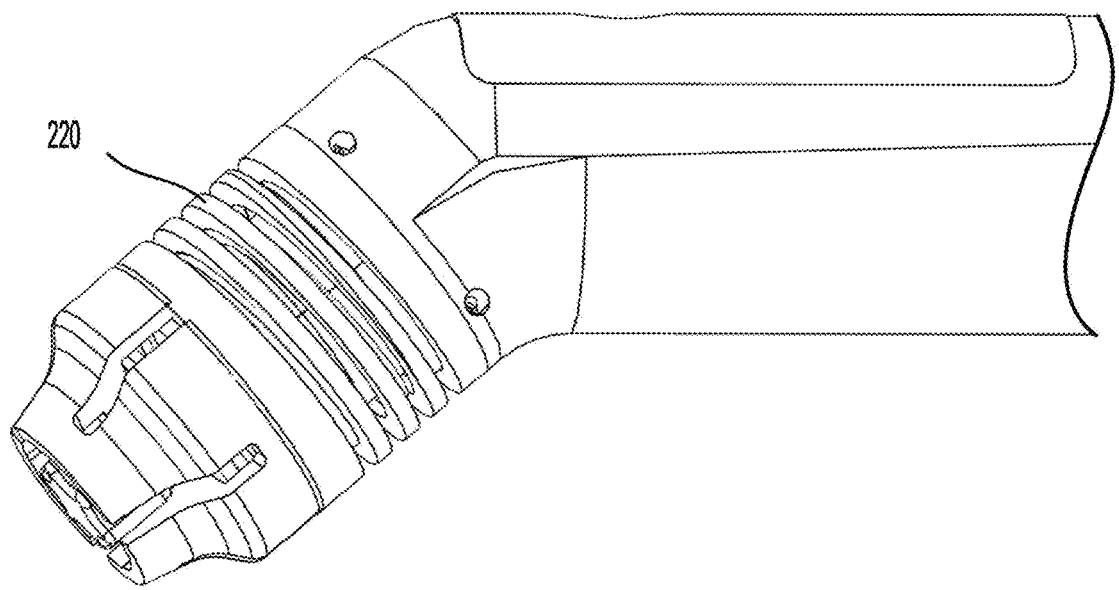
FIG. 32A is a side view of a tip portion of an example screwdriver in accordance with the principles of the present disclosure.
Figure 32B:
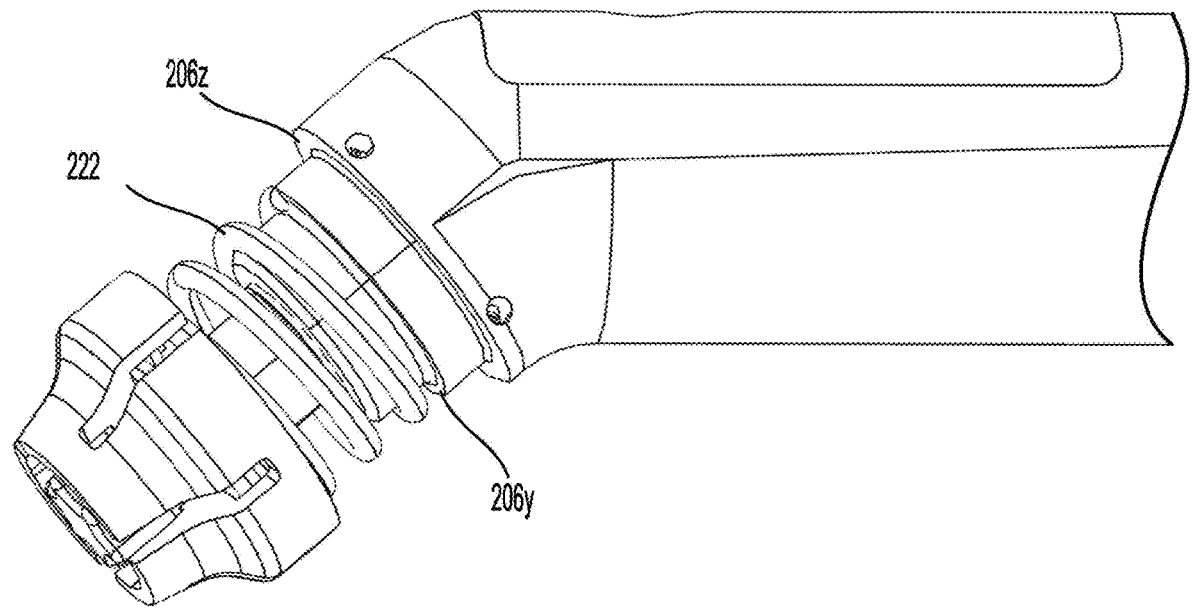
FIG. 32B is a side view of a tip portion of an example screwdriver with compression spring in accordance with the principles of the present disclosure.

Referring generally to FIGS. 28-32B a tip portion 206 of an example screwdriver 200 may be illustrated. FIG. 28 is a cross section view of a tip portion 206 and FIG. 29 is a removed parts view of a tip portion 206 of an example screwdriver 200 in accordance with the principles of the present disclosure. FIG. 30 is a removed parts view of an example gear mechanism 203 in accordance with the principles of the present disclosure and FIG. 31 is a removed parts view of an alternate example gear mechanism 203 in accordance with the principles of the present disclosure. FIG. 32A is a side view of an example tip portion 206 in a fully assembled condition and FIG. 32B is a side view of an example tip portion 206 in accordance with the principles of the present disclosure.

In some embodiments, retaining cap 208 may include at least one retaining feature such as bump 208c, for example. Additionally, some example bone screws 300 may include an indent 210. In a head on view, the indent 210 may be defined by a radius of a circle that is slightly less than a radius defining a tip portion of the head of bone screw 300. The retaining bump 208c may have a curved surface profile including a width and depth that corresponds to the width and depth of the indent 210. Additionally, when viewed in a cross sectional view, retaining bump 208c may be seated within indent 210. In disclosed embodiments, tip portion 206 may include a first spring 220 and a second spring 222. However, in some embodiments, only one of first spring 220 or second spring 222 may be provided. Example springs 220, 222 may be referred to as industrial compression springs, machined springs, coil springs, and/or helical springs. First spring 220 may have outside surfaces that are flush with the adjacent surfaces, i.e., outside surfaces of retaining cap 208 and tip portion 206 (see FIG. 32A). For example, first spring 220 may act against a bearing surface 208z of retaining cap 208 and a bearing surface 206z of tip portion 206 (see FIG. 28 and FIGS. 32A-32B). Second spring 222 may be disposed within a central cavity of first spring 220, i.e., second spring 222 may be surrounded by first spring 220. For example, second spring 222 may act against corresponding inset radial surfaces of retaining cap 208 and tip portion 206 that are disposed and inset radially from the surfaces that first spring 220 acts against. For example, second spring 222 may act against channel 208y of retaining cap 208 and bearing surface 206y of tip portion 206. In some embodiments, channel 208y may extend circumferentially around an interior of retaining cap 208 that is radially inset from the outside surface of retaining cap 208. Additionally, second spring 122 may act against a portion of bearing surface 206y that is radially inset from the portion of bearing surface 206z that contacts first spring 220 (see FIG. 28). Stated another way, first spring 220 may act against a radially outset surface and second spring 222 may act against a radially inset surface, at least with respect to one another. Each of springs 220, 222 may have a relative stiffness of about 1 N/mm-6 N/mm, more particularly about 2 N/mm-4 N/mm, and even more particularly about 3.35 N/mm. In some embodiments, only the second spring 222 contributes a significant portion of the relative stiffness ranges provided above and the first spring 220 may have a negligible contribution. In other embodiments, only the first spring 220 contributes a significant portion of the relative stiffness ranges provided above and the second spring 222 may have a negligible contribution. In other embodiments still, the sum of the stiffness of the first and second springs 220, 222 may be additive such that the combined stiffness of the first and second springs 220, 222 may be within the stiffness ranges provided above. At least one advantage of the first and/or second springs 220, 222 is that they may facilitate the clipping of a bone screw 300 to retaining cap 208 and the extraction of the bone screw 300 from the retaining cap 208 in a progressive manner. For example, when driving a bone screw 300 into a target site, the first and/or second springs 220, 222 may compress when the bone screw 300 nears a fully anchored position helping to moderate the extraction force required to remove the bone screw 300 in a precise or controlled way, or at least a relatively more precise or controlled way relative to conventional screw drivers. For example still, the first and/or second springs 220, 222 may allow the retaining cap 208 to progressively release a bone screw 300 when it is inserted and installed into a cavity or target location in a similar way.

FIG. 29 illustrates an alternate embodiment showing the retaining cap 208 including a retaining ring 208r. Retaining ring 208r may be formed of the same or similar materials as previously disclosed with respect to retaining cap 208. In at least one embodiment, retaining ring 208r is formed of a metallic material and retaining cap 208 is formed of PEEK. Retaining ring 208r may have a generally toroidal shape or torus shape. The retaining ring 208r may have at least one expansion joint 208e that divides the retaining ring into separable spaced apart regions. The expansion joint 208e may allow the retaining ring 208r to expand radially when a bone screw 300 is insert into the retaining cap 208. For example, the retaining ring 208r may have an internal radius and an external radius and the internal radius may correspond to the radius of a head of a bone screw 300. In the disclosed embodiment, the internal radius of the retaining ring 208r may be slightly less than the radius of a head of a bone screw 300 and may expand radially when a bone screw 300 is insert therein. In the disclosed embodiment, bone screw 300 includes an indent 310 (see FIGS. 19-22). In a head on view, the indent 310 may be defined by a radius of a circle that is slightly less than a radius defining a tip portion of the head of bone screw 300. The retaining ring 208r may have an internal radius that corresponds to the radius of the indent 310. Additionally, when viewed in a cross sectional view, retaining ring 208r may have a diameter that corresponds to a depth of indent 310 and the retaining ring 208r may be half-seated within the indent 310. For example, when the retaining ring 208r is seated in the indent 310, about half of the retaining ring 208r extends above the indent 310 and the other half of retaining ring 208r is within indent 310. However, in other embodiments the retaining ring 208r may be fully seated or partially seated in indent 310, e.g., 100% seated, 75% seated, or 25% seated.

FIG. 16 illustrates an alternate embodiment where retaining cap 208 includes a protrusion 208x (or a lip portion). Protrusion 208x may be a rounded or arcuate protrusion that extends circumferentially around the inside of retaining cap 208. For example, when viewed in cross section, protrusion 208x may be defined by a radius that is relatively smaller than a radius of the head of bone screw 300. At least one advantage of protrusion 208x is that it may assist in retaining bone screw 300 inside of retaining cap 208. Furthermore, in some embodiments, protrusion 208x may serve a similar function and/or have similar functionality as bump 208c. At least one advantage to protrusion 208x is that conventional bone screws that do not include indent 310 may be safely retained and controllably released by retaining cap 208 similarly as explained above with respect to bump 208c. In some embodiments, retaining cap 208 may combine both bump 208c and protrusion 208x.

FIG. 31 illustrates an alternate embodiment including a joint mechanism 205 in lieu of gear mechanism 203. Joint mechanism 205 may be operable/drivable via drive shaft 202 in the same, similar, or substantially the same way as gear mechanism 203 as explained above. As illustrated in FIG. 31, joint mechanism 205 may include a spherical portion 205a that is rotatably seated in a spherical housing area of tip portion 206. Spherical portion 205a may be fixedly coupled to drive portion 205b and drive portion 205b may include an end portion configured for driving bone screw 300 in the same, similar, or substantially the same way as drive end 202b explained above. In the example embodiment, spherical portion 205a includes an aperture 205c such as a drilled out portion or slotted portion configured to receive drive shaft 202 therein, for example. Drive shaft 202 may extend into aperture 205c and couple with spherical portion 205a and/or drive portion 205b to transmit rotational movement from drive shaft 202 to bone screw 300. For example drive shaft 202 may extend into aperture 205c and couple with spherical portion 205a and/or drive portion 205b via a pin connection. At least one advantage of this structural arrangement is that the joint mechanism 205 may be configured such that it is adjustable to accommodate a range of various angles of inclination β of tip portion 206 with respect to housing 110. For example, joint mechanism 205 may enable a user selectable and greater operating range of various angles of inclination β. For example still, joint mechanism 205 may enable tip portion 206 to be adjustably inclined within a range of about 20°-60°, and more particularly about 30°-50 with respect to a longitudinal direction of housing 110. However, it shall be understood that in some embodiments the angle of inclination β may be fixed.

FIG. 31 also illustrates an alternate embodiment of retaining cap 208. In the disclosed embodiment, retaining cap 208 may include a tapered portion 208t. For example, the bone screw connecting side 208bs of retaining cap 208 may taper conically. For example still, when viewed in cross-section, a radius of tapered portion 208t may progressively decrease along retaining cap 208 to an outermost end thereof. It shall be understood that retaining cap 208 may include bump 208c, protrusion 208x, and/or tapered portion 208t and any combination thereof. Additionally, any of bump 208c, protrusion 208x, and/or tapered portion 208t may be referred to as a retaining contour or retaining feature in some embodiments.

Example screwdriver 200 may be operably coupled to a manual hand driver 401 and/or powered driver 400 as explained above with respect to drill 100. Hand driver 401 may selectively couple and uncouple with drive portion 202a of drive shaft 202, for example Hand driver may be of a fixed type or a ratcheting type. At least one example of a manual hand driver 401 may be the commercially available Medtronic QC handle. Example screwdriver 200 may also be operably coupled to a powered driver 400 in accordance with the principles of the present disclosure. Powered driver 400 may be powered by any means, e.g., electrically operated or pneumatically operated as explained above with respect to drill 100.

Figure 33:
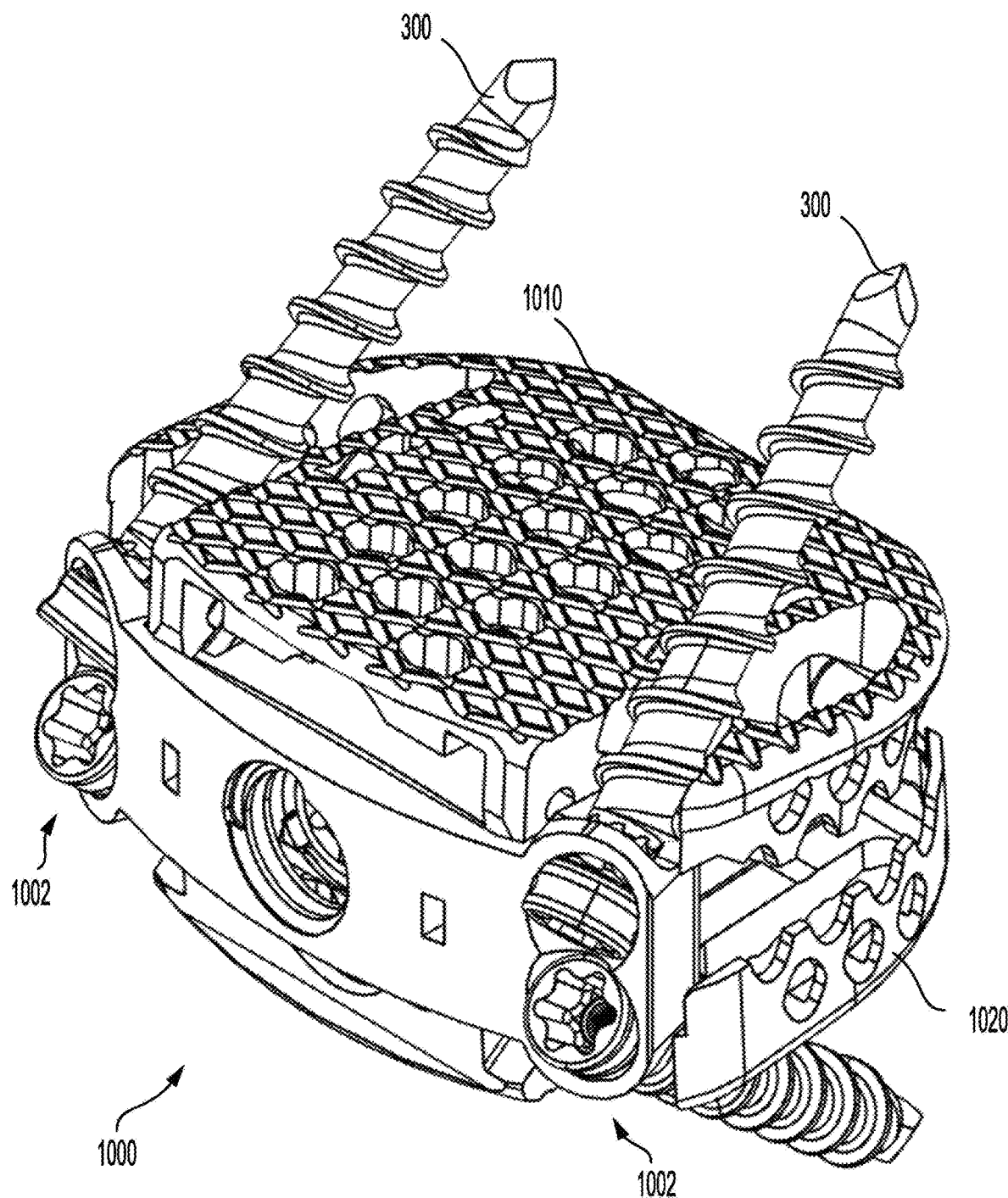

FIG. 33 is a perspective view of an example medical device 1000 that includes a plurality of inclined bone screw apertures 1001. Consistent with the principles of the disclosure, various example screwdrivers 200 may include a tip portion 206 that is angled at a degree β with respect to a longitudinal direction of housing 110. In some embodiments, tip portion 206 may be angled such that the degree β corresponds to the desired inclination of bone screw 300 and/or bone screw apertures 1001. Additionally, tip portion 206 may be angled at a degree β that accounts for both (1) the desired inclination of bone screw 300 and/or bone screw apertures 1001; and (2) the particular type of surgery (anterior, lateral, oblique, etc.) and surgical access opening available to a surgeon.

What is claimed is:

1. A drill extending from a distal end to a proximal end, comprising:
    a housing extending in a longitudinal direction, the housing including a plurality of channels extending along the housing, each channel circumscribing the housing and having a plurality of detents therein;
    a rotatable drive shaft including a first drive end disposed at the proximal end of the drill and being configured for coupling to a driver, the rotatable drive shaft having a main shaft portion extending in the longitudinal direction through the housing between the first drive end and a second drive end;
    an angled tip region defining the distal end of the drill, the angled tip region comprising a drill bit coupler configured to receive a drill bit and orient the drill bit in an angled direction with respect to the longitudinal direction thereby defining a drilling axis of the drill bit;
    an angled gear mechanism comprising a plurality of teeth, the angled gear mechanism being configured to transfer a rotational force applied to the first drive end through the second drive end and drill bit coupler;
    a movable handle mechanism coupled to and disposed at a medial portion of the housing, the movable handle mechanism comprising a positioning handle extending in a direction away from the longitudinal direction; and
    a sleeve radially disposed at a distal end of the angled tip region and configured to radially surround at least a first portion of the drill bit when received in the drill bit coupler,
    wherein the movable handle mechanism is configured to: (a) securely couple to the housing via one channel of the plurality of channels and one detent of the plurality of detents, (b) move forward and backward along the housing in the longitudinal direction between any one of the plurality of channels, and (c) rotate clockwise and counterclockwise around the housing between any one of the plurality of detents.

2. The drill of claim 1, wherein: the movable handle mechanism further comprises a positioning ball having a size and shape corresponding to a size and shape of a detent of the plurality of detents, the positioning ball being configured to securely couple the movable handle mechanism via one detent of the plurality of detents.

3. The drill of claim 1, wherein:
the movable handle mechanism is configured to move forward and backward in a longitudinal direction along the housing between a proximal stop ring and a distal stop ring.

4. The drill of claim 1, wherein:
the angled tip region further comprises a compressible spring contacting the sleeve and configured to bias the sleeve in the angled direction, and
the compressible spring is configured to surround at least a second portion of the drill bit when received in the drill bit coupler.

5. The drill of claim 4, wherein:
in a first mode of operation where the spring is in a neutral position, the sleeve and compressible spring are configured to surround lateral sidewalls of the drill bit when received in the drill bit coupler, and
in a second mode of operation, the compressible spring is configured to compress in a direction parallel to the angled direction towards the mechanism.

6. An angled driver, comprising:
a housing extending in a longitudinal direction, the housing including a plurality of sequential channels extending along the housing in the longitudinal direction, each channel circumscribes the housing and includes a plurality of detents therein;
a rotatable drive shaft including a first drive end disposed at a proximal end of the driver, the rotatable drive shaft having a main shaft portion extending in the longitudinal direction through the housing between the first drive end and an angled second drive end;
an angled tip region defining a distal end of the driver, the angled tip region comprising a drill bit coupler including a drill bit aperture configured to receive a drill bit and orient the drill bit in an angled direction with respect to the longitudinal direction;
a mechanism being configured to transfer a rotational force applied to the first drive end through the second drive end and the drill bit coupler;
a movable handle mechanism coupled to and disposed at a medial portion of the housing, the movable handle mechanism comprising a positioning handle extending in a direction away from the longitudinal direction; and
a sleeve radially disposed at a distal end of the angled tip region and configured to radially surround at least a first portion of the drill bit when received in the drill bit coupler,
wherein the movable handle mechanism is configured to:
(a) securely couple to the housing via one channel of the plurality of channels and one detent of the plurality of detents, (b) move forward and backward along the housing in the longitudinal direction between any one of the plurality of sequential channels, and (c) rotate clockwise and counterclockwise around the housing between any one of the plurality of detents.

7. The drill of claim 6, wherein:
the angled tip region further comprises a compressible spring contacting the sleeve and configured to bias the sleeve in the angled direction, and
the compressible spring is configured to surround at least a second portion of the drill bit when received in the drill bit coupler.

8. The drill of claim 6, wherein the mechanism is a gear mechanism that comprises a first plurality of teeth and a second plurality of teeth, the second plurality of teeth being angled with respect to the first plurality of teeth.

9. The drill of claim 6, wherein the mechanism is a socket joint mechanism that comprises a spherical socket joint including a spherical end having at least one aperture configured to receive a portion of the rotatable drive shaft.

10. A drill extending from a distal end to a proximal end, comprising:
a housing extending in a longitudinal direction, the housing including a plurality of channels extending along the housing, each channel circumscribing the housing and having a plurality of detents therein;
a rotatable drive shaft including a first drive end disposed at the proximal end of the drill and being configured for coupling to a driver, the rotatable drive shaft having a main shaft portion extending in the longitudinal direction through the housing between the first drive end and a second drive end;
an angled tip region defining the distal end of the drill, the angled tip region comprising a drill bit coupler configured to receive a drill bit and orient the drill bit in an angled direction with respect to the longitudinal direction thereby defining a drilling axis of the drill bit;
a socket joint mechanism that comprises a spherical socket joint including a spherical end having at least one aperture configured to receive a portion of the rotatable drive shaft, the socket joint mechanism being configured to transfer a rotational force applied to the first drive end through the second drive end and drill bit coupler;
a movable handle mechanism coupled to and disposed at a medial portion of the housing, the movable handle mechanism comprising a positioning handle extending in a direction away from the longitudinal direction; and
a sleeve radially disposed at a distal end of the angled tip region and configured to radially surround at least a first portion of the drill bit when received in the drill bit coupler,
wherein the movable handle mechanism is configured to:
(a) securely couple to the housing via one channel of the plurality of channels and one detent of the plurality of detents, (b) move forward and backward along the housing in the longitudinal direction between any one of the plurality of channels, and (c) rotate clockwise and counterclockwise around the housing between any one of the plurality of detents.

* * * * *